(12) United States Patent
Yokel et al.

(10) Patent No.: US 9,139,456 B2
(45) Date of Patent: Sep. 22, 2015

(54) CHELATING COMPOUNDS AND IMMOBILIZED TETHERED CHELATORS

(75) Inventors: Robert A. Yokel, Lexington, KY (US); Wesley R. Harris, St. Louis, MO (US); Christopher D. Spilling, St. Louis, MO (US); Robert Joseph Kuhn, Nicholasville, KY (US); Surendra Dawadi, St. Louis, MO (US)

(73) Assignee: The Curators of the University of Missouri, Columbia, MO (US)

( * ) Notice: Subject to any disclaimer, the term of this patent is extended or adjusted under 35 U.S.C. 154(b) by 959 days.

(21) Appl. No.: 13/278,498

(22) Filed: Oct. 21, 2011

(65) Prior Publication Data

US 2012/0061325 A1     Mar. 15, 2012

Related U.S. Application Data

(60) Continuation-in-part of application No. 13/052,477, filed on Mar. 21, 2011, now Pat. No. 8,066,883, which is a division of application No. 12/104,066, filed on Apr. 16, 2008, now Pat. No. 7,932,326.

(51) Int. Cl.

| | |
|---|---|
| C02F 1/68 | (2006.01) |
| B01J 20/32 | (2006.01) |
| B01J 45/00 | (2006.01) |
| C07C 217/28 | (2006.01) |
| C07C 255/13 | (2006.01) |
| C07C 259/06 | (2006.01) |
| C07C 311/17 | (2006.01) |
| C02F 101/20 | (2006.01) |
| B01D 15/38 | (2006.01) |

(52) U.S. Cl.
CPC ............ *C02F 1/683* (2013.01); *B01J 20/3251* (2013.01); *B01J 20/3253* (2013.01); *B01J 20/3255* (2013.01); *B01J 45/00* (2013.01); *C07C 217/28* (2013.01); *C07C 255/13* (2013.01); *C07C 259/06* (2013.01); *C07C 311/17* (2013.01); *B01D 15/3828* (2013.01); *C02F 2101/20* (2013.01)

(58) Field of Classification Search
None
See application file for complete search history.

(56) References Cited

U.S. PATENT DOCUMENTS

| | | |
|---|---|---|
| 4,599,361 A | 7/1986 | Dickens et al. |
| 4,654,299 A | 3/1987 | Lentfer |
| 4,666,927 A | 5/1987 | Hider et al. |
| 4,671,901 A | 6/1987 | Green |
| 4,684,482 A | 8/1987 | Green |
| 5,089,644 A | 2/1992 | Quay et al. |
| 5,104,865 A | 4/1992 | Hider et al. |
| 5,254,724 A | 10/1993 | Bergeron, Jr. |

(Continued)

FOREIGN PATENT DOCUMENTS

| | | |
|---|---|---|
| CN | 1413773 | 4/2003 |
| WO | WO 93/00327 | 1/1993 |

OTHER PUBLICATIONS

Ouchetto, H., "A new route to trihydroxyamate-containing artificial siderophores and synthesis of a new fluorescent probe," Bioorganic and Medicinal Chemistry, 13 (2005) 1799-1803.*

(Continued)

*Primary Examiner* — Chester Barry
(74) *Attorney, Agent, or Firm* — King & Schickli PLLC

(57) ABSTRACT

Novel compounds useful as chelators, intermediates for their production and methods for removing trivalent and tetravalent metal ions from solution are presented.

5 Claims, 14 Drawing Sheets

(56) References Cited

U.S. PATENT DOCUMENTS

| | | | |
|---|---|---|---|
| 5,312,730 | A | 5/1994 | Piran et al. |
| 5,332,679 | A | 7/1994 | Simons et al. |
| 5,424,219 | A | 6/1995 | Jirikowski |
| 5,663,201 | A | 9/1997 | Lowther et al. |
| 5,728,681 | A | 3/1998 | Kido et al. |
| 5,739,167 | A | 4/1998 | Lowther et al. |
| 5,756,825 | A | 5/1998 | Safavy et al. |
| 6,022,865 | A | 2/2000 | Deutsch |
| 6,071,412 | A | 6/2000 | Ambrus et al. |
| 6,132,750 | A | 10/2000 | Perrier et al. |
| 6,391,980 | B1 | 5/2002 | Clark |
| 6,693,173 | B2 | 2/2004 | Mamidi et al. |
| 6,858,414 | B2 | 2/2005 | Keri et al. |
| 7,932,326 | B2 | 4/2011 | Yokel et al. |
| 8,066,883 | B2 | 11/2011 | Yokel et al. |
| 2005/0276862 | A1 | 12/2005 | Bringley et al. |
| 2005/0277752 | A1 | 12/2005 | Bringley et al. |
| 2012/0061325 | A1* | 3/2012 | Yokel et al. ............. 210/681 |

OTHER PUBLICATIONS

Liu, et al., Synthesis and Coordination Behaviour of Hydroxamate Resin with Varying Spacer Groups, Polyhedron vol. 11, No. 5, pp. 551-558, 1992, Great Britain.

Vernon, Frederick, Chelating Ion Exchangers—The Synthesis and Uses of Poly(hydroxamic Acid) Resins, Pure and Appl. Chem., vol. 54, No. 11, pp. 2151-2158, 1982, Great Britain.

Crumbliss, et al., Synthesis and Characterization of Iron(III) Chelating Analogues of Siderophores on Organic Solid Supports, Inorganica Chemica Acta, 133 (1987) 281-287, Switzerland.

Hutchinson, et al., Solid phase extraction of metal ions using immobilised chelating calixarene tetrahydroxamates, Analytica Chimica Acta 291 (1994 269-275, Elsevier Science B.V.

Lu, et al., Kinetic studies of aluminum and zinc speciation in river water and snow, Analytica Chimica Acta 293 (1994) 95-108, Elsevier Science B.V.

Philips et al., Extraction of Metal Ions by N-Phenyl-, N-Methyl-, and N-Unsubstituted Hydroxamic Acid Resins, Analytical Chimica Acta, 139 (1982) 237-249, Elsevier Scientific Publishing Company, Amsterdam.

Evers et al., Similarities Between Al(3) and Fe3, Evers et al. Inorg. Chem. 1989, 28: 2189.

MBA Tech Connection, Intellectual Property Overview Report, Aluminum Chelator Concept, undated, pp. 1-26.

Dr. Yokel, Reduction of Toxicity in the Premature Neonate Associated with Aluminum as a Contaminant of Total Parenteral Nutrition Solutions, Thrasher Research Fund Award, No. 02818-1. 2004, pp. 1-5.

Dr. Robert A. Yokel, Reduction of Toxicity in the Premature Neonate Associated with Aluminum as a Contaminant of Total Parenteral Nutrition Solutions. Thrasher Research Fund, Award No. 02818-1, Twelve Month Research Progress Report.

Dr. Robert A. Yokel, Reduction of Toxicity in the Premature Neonate Associated with Aluminum as a Contaminant of Total Parenteral Nutrition Solutions. Thrasher Research Fund, Award No. 02818-1. Eighteen Month Research Progress Report (undated), pp. 1-4.

Dr. Robert A. Yokel, Semiannual Progress Report, Thrasher Research Fund, Feb. 14, 2006, Reporting Period Mar. 1, 2005 to Aug. 31, 2005. Award No. 02818-1. pp. 1-4.

Dr, Robert A. Yokel, Reduction of Toxicity in the Premature Neonate Associated with Aluminum as a Contaminant of Total Perenteral Nutrition Solutions. Thrasher Research Project. Scientific Abstract; Award 02818-1. (undated); pp. 4-17.

Chen & Zhan, Computational Modeling of Aluminum (III)- Ligand Binding. University of Kentucky; Jan. 18, 2006; pp. 1-3.

Dr. Robert A. Yokel et al. Reduction of Toxicity in the Premature Neonate Associated with Aluminum as a Contaminant of Total Parenteral Nutrition Solutions. Pharmacy College, University of Kentucky. (undated).

* cited by examiner

CHELATING COMPOUNDS AND IMMOBILIZED TETHERED CHELATORS

This application is a continuation-in-part of U.S. patent application Ser. No. 13/052,477, filed 21 Mar. 2011, now U.S. Pat. No. 8,066,883, which is a divisional of U.S. patent application Ser. No. 12/104,066, filed 16 Apr. 2008, now U.S. Pat. No. 7,932,326, the entire disclosures of which are incorporated herein by reference.

TECHNICAL FIELD AND INDUSTRIAL APPLICABILITY OF THE INVENTION

The present invention relates generally to the chemical field and, more particularly, to novel chelating agents, useful intermediates for synthesizing those chelating agents, the immobilization of those agents on a solid support resin, and the use of those chelating resins to remove metal ions from aqueous solutions.

BACKGROUND OF THE INVENTION

A chelator or chelating agent is a polydentate ligand that bonds to more than one coordination site of a metal ion. Chelating agents have long been known in the art to be useful in chemical analysis, in environmental remediation and in medicine. In chelation therapy, a chelating agent is employed to bind a poisonous metal agent such as mercury, arsenic, iron, lead or aluminum in order to displace the ion from biological ligands such as proteins and convert the metal ion into a less toxic form that can be excreted without further interaction with the body.

The present invention relates to (1) novel chelating agents or compounds, (2) novel immobilized, tethered chelators comprising the novel chelating compounds linked to immobilized supports and (3) methods of employing the novel compounds and chelators to remove trivalent and tetravalent metal ion such as $Al^{3+}$ and $Pu^{4+}$ from aqueous systems in situ, in vivo and in vitro.

There have been previous studies of tripodal, trihydroxamic acids. Most of these ligands are based on tripodal platforms of tris(2-aminethyl)amine (tren) (Matsumoto et al., Chem. Commun. 2001, 978-979; Matsumoto et al., Inorg. Chem., 2001, 40: 190-191; Matsumoto et al., Inorg. Chem. 2004, 43: 8538-8546; Ng et al., Inorg. Chem. 1989, 28: 2062-2066), tris(3-aminopropyl)amine (Matsumoto et al., Eur. J. Inorg. Chem. 2001, 2481-2484); or nitrilotriacetic acid (nta) (Lee et al, J. Med. Chem. 1985, 28: 317-323; Hara et al., Inorg. Chem. 2000, 39: 5074-5082). These studies teach that such ligands form $Fe^{3+}$ complexes with binding constants in the range of $10^{28}$ to $10^{33}$, so long as there are five or six atoms connecting the bridgehead atom of the platform and the first atom of the hydroxamate functional group on the sidearm (Matsumoto et al., Eur. J. Inorg. Chem. 2001, 2481-2484; Matsumoto et al., Inorg. Chem. 2001, 40: 190-191; Ng et al., Inorg. Chem. 1989, 28: 2062-2066). These ligands include amide functional groups in the sidearms, and the iron complexes appear to be stabilized by intramolecular hydrogen bonding between the amide functional groups (Matsumoto et al., Inorg. Chem. 2001, 40:190-191).

The common feature of all the above ligands is that the bridgehead atom is a tertiary nitrogen. To attach these ligands to a solid support via this nitrogen would require the formation of a quaternary ammonium group. This is expected to have an adverse effect on the chelating ability of the ligand. It will introduce a permanent positive charge on the ligand, resulting in electrostatic repulsion of the target metal ion. In some cases, it will also require a change in the conformation of the metal complex.

A few tripodal tris(hydroxamate) ligands have been prepared in which the bridgehead atom is a carbon, rather than a nitrogen. These ligands are built on tripodal bases of either 1,1,1-tris(hydroxymethyl)ethane (Motekaitis et al., Inorg. Chem. 1991, 30: 1554-1556) or 1,1,1-tris(hydroxymethyl) propane (Dayan et al., Inorg. Chem. 1993, 32: 1467-1475). Hydroxamate groups were added to these tripodal bases through ether linkages. These studies teach that one needs 4 or 5 atoms between the bridgehead carbon and the first atom of the hydroxamate functional group for strong metal binding. The $Fe^{3+}$ complexes of these ligands have binding constants of $10^{26}$ to $10^{28}$. However, it is not possible to link these ligands to a polymeric support through the quaternary carbon bridgehead atom.

The current invention is based in the use of hydroxyalkylaminomethanes, especially the common buffer tris(1,1,1-tris (hydroxymethyl)aminomethane), as the tripodal base. The use of hydroxylalkylaminomethanes allows us to construct tripodal chelating functional groups that will mimic the high metal binding affinities of the ligands already in the literature, but it also provides a free amine group that can be used to easily attach the ligands to a variety of solid supports.

In issued U.S. Pat. No. 7,932,326, all of the hydroxamate ligands are derived from tris[tris(hydroxymethyl)aminomethane]. The oxygen atoms of tris are alkylated with alkyl groups of various lengths terminating in hydroxamic acids. The amine of the tris is linked to a polymer support via sulfonamide, carboxamide or urea groups amongst others, to give the resin supported ligands. This document relates to an extension of that work.

SUMMARY OF THE INVENTION

In accordance with the purposes of the present invention as described herein, novel di- and tripodal compounds are disclosed for use as chelating agents. Such compounds include, but are not limited to, novel tripodal trihydroxamate chelating agents having a tris(hydroxylalky)aminomethane platform, such chelating agents bonded to a polymeric resin, useful intermediates for making such chelating agents and to a method of removing a trivalent metal such as aluminum from a solution using such chelating agents.

In the following description there is shown and described several different embodiments of the invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings, incorporated herein and forming a part of the specification, illustrate several aspects of the present invention and together with the description serve to explain certain principles of the invention. In the drawings.

The data points are: 1-3 represent the 1:1, 1:2, and 1:3 complexes with acetohydroxamic acid. Points 4-7 represent a series of linear dihydroxamates, in which the hydroxamate groups are separated by 4, 5, 6, or 7 methylene groups. Points 8 and 9 are the binding constants of the desferrioxamine (DFO) complex and the protonated complex of DFO. Point 10 is mesitylenetrihydroxamic acid. The filled triangles represent compounds from the current invention. Point 11 represents the complexes of Ligand 1, point 12 represents the protonated complexes of Ligand 1, and point 13 represents the complexes of Ligand 7.

Figure 1:
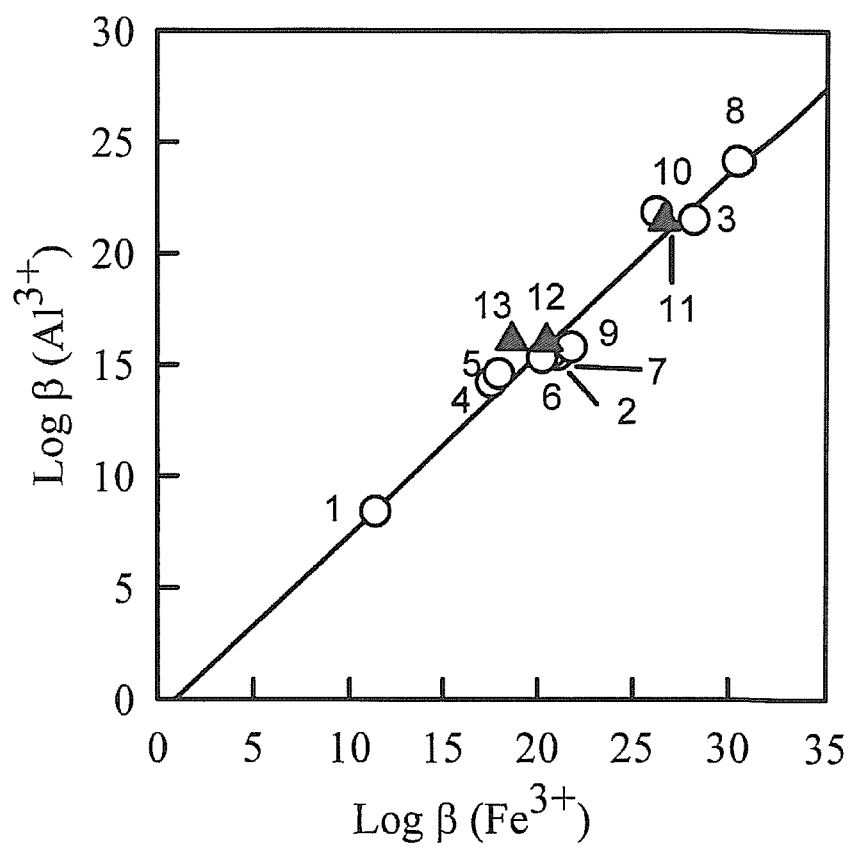
FIG. 1 is a linear free energy relationship showing the correlation between the binding affinities of $Fe^{3+}$ and $Al^{3+}$ with hydroxamate ligands. Each data point represents a ligand, with the log β value for $Fe^{3+}$ as the x-coordinate and the log β value for $Al^{3+}$ as the y-coordinate. The open symbols represent reference compounds described in the literature.
Figure 2:
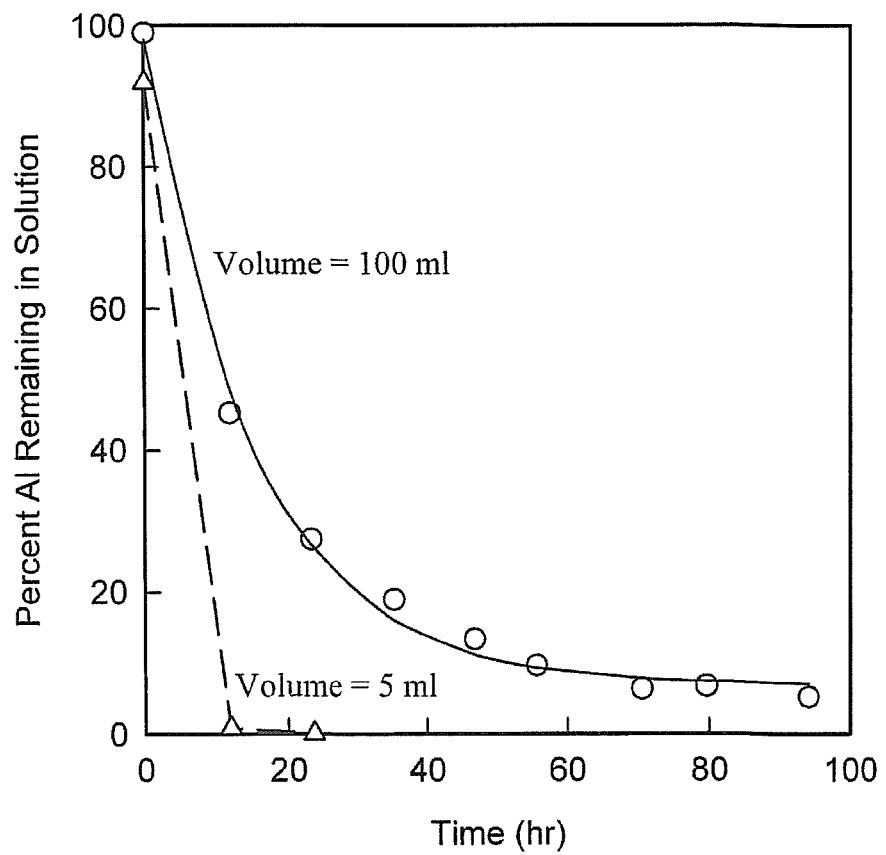

FIG. 2 is a graph demonstrating the binding of $Al^{3+}$ to 50 mg Resin 1 in which the concentration of free $Al^{3+}$ remaining in solution after the addition of 50 mcg Al at time 0 to either 100 ml or 5 ml of 4-morpholineethanesulfonic acid (MES) buffer at pH 5 has been determined by electrothermal atomic absorption spectroscopy (ETAAS).

Figure 3:
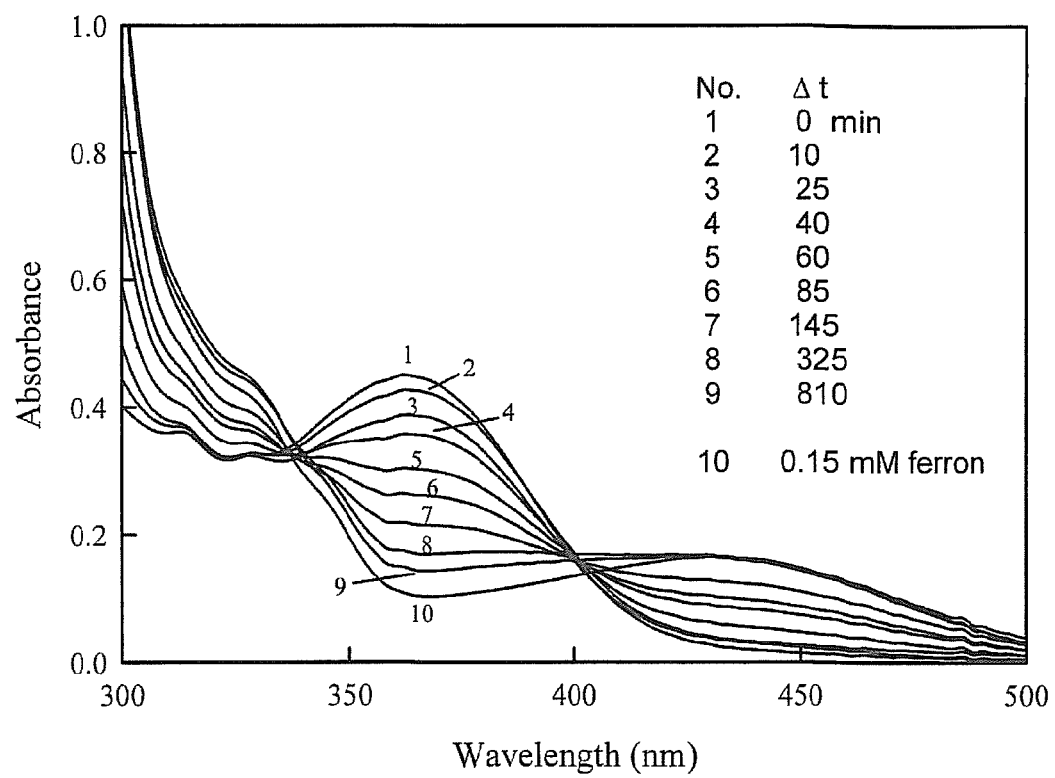

FIG. 3 is a spectrophotometric assay showing the binding of $Al^{3+}$ to Resin 1 following addition of 22.8 mg of Resin 1 to 3 ml of 0.15 mM Al-ferron at pH 5. Spectra show the decrease in the absorbance of Al-ferron at 364 nm and the increase in the absorbance of free ferron at 434 nm. Spectrum 10 shows the reference spectrum for 0.15 mM ferron.

Figure 4:
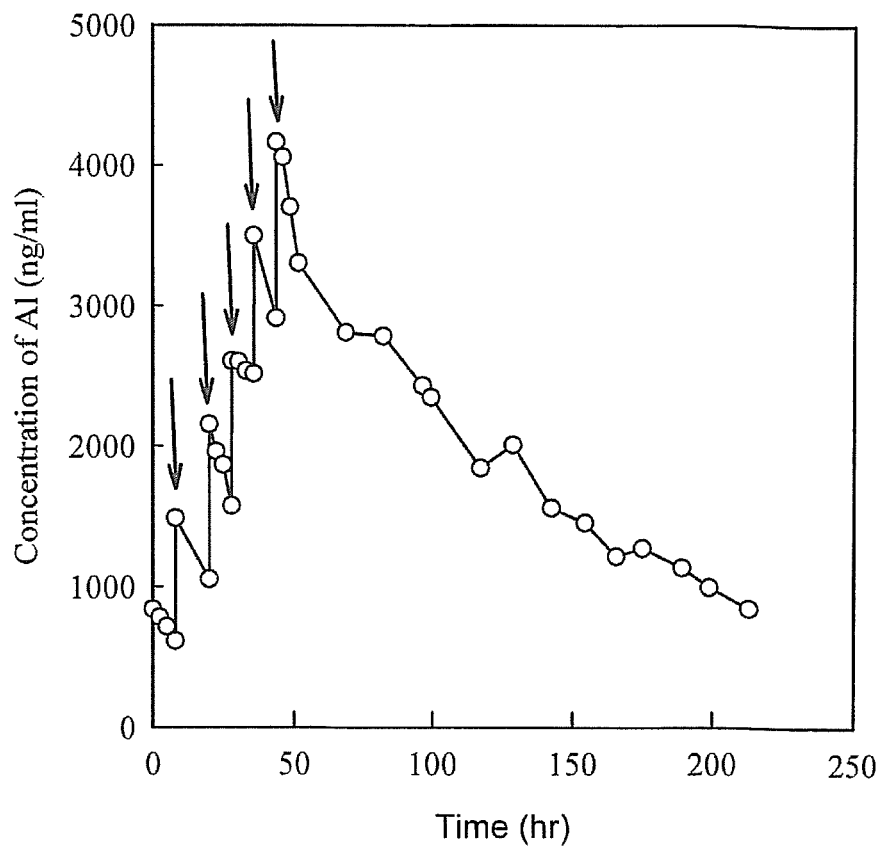
Figure 5:
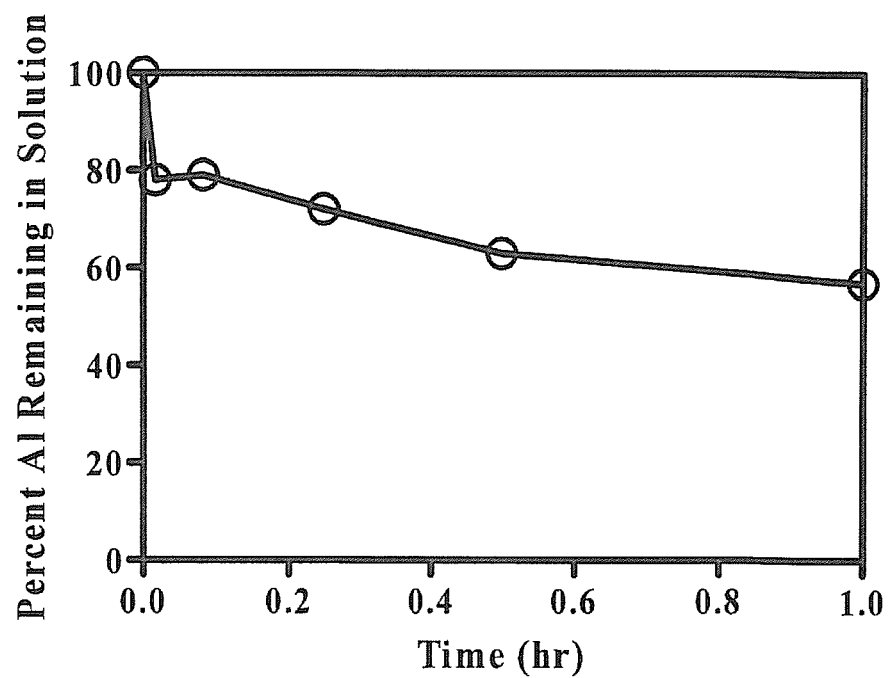

FIG. 4 is a graph illustrating the binding of $Al^{3+}$ to Resin 1 following the sequential addition of six aliquots of 100 mcg of Al to 50 mg of Resin 1 suspended in 100 ml of pH 5 MES buffer. The first aliquot of Al was added at time=0. Five subsequent additions were made at 12 hr intervals at the time indicated by the arrows on the graph. The free Al concentration was determined by ETAAS; and FIG. 5 is a graph illustrating the binding of $Al^{3+}$ to Resin 1 following the addition of 250 mg of Resin 1 to 0.5 ml of 0.23M calcium gluconate containing ~9000 ng Al/ml. The free Al concentration was determined by ETAAS.

Figure 6:
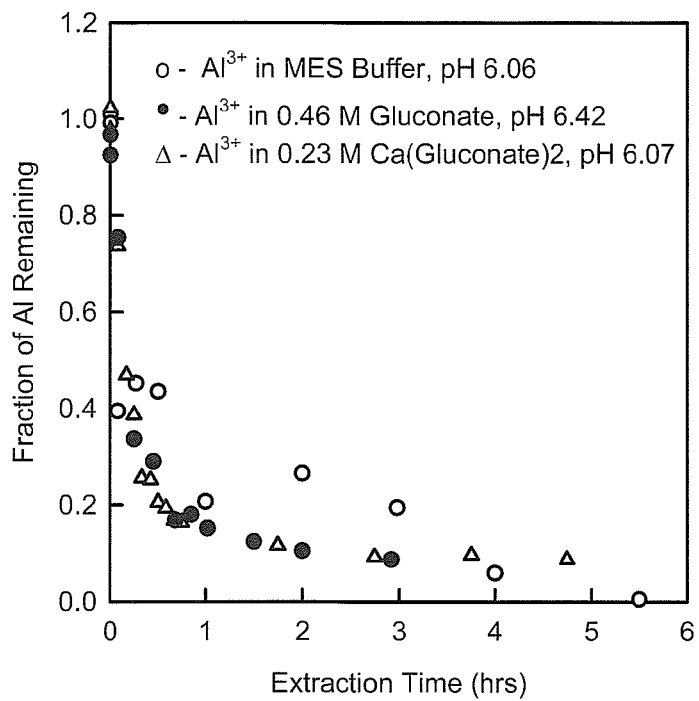

FIG. 6 is a plot of the fraction of Al remaining in solution as a function of time during the extraction of $Al^{3+}$ by resin 9. Three solutions were extracted: a 0.1 M MES buffer at pH 6.06, which had been spiked with 6.3 ppm Al; a solution of 0.46 M gluconate containing 3.4 ppm Al, which had been adjusted to pH 6.4 by the addition of tetramethylammonium hydroxide; and a commercial sample of 0.23 M calcium $(gluconate)_2$, which contained 5.9 ppm Al and had a pH of 6.07. In each experiment, approximately 240 mg of resin 9 was added to 10 ml of solution. The mixtures were stirred by a magnetic overhead stirrer during the extraction. At periodic times, a 100 μL aliquot was removed from the sample and analyzed by inductively coupled plasma-mass spectrometry to determine the Al concentration.

Figure 7:
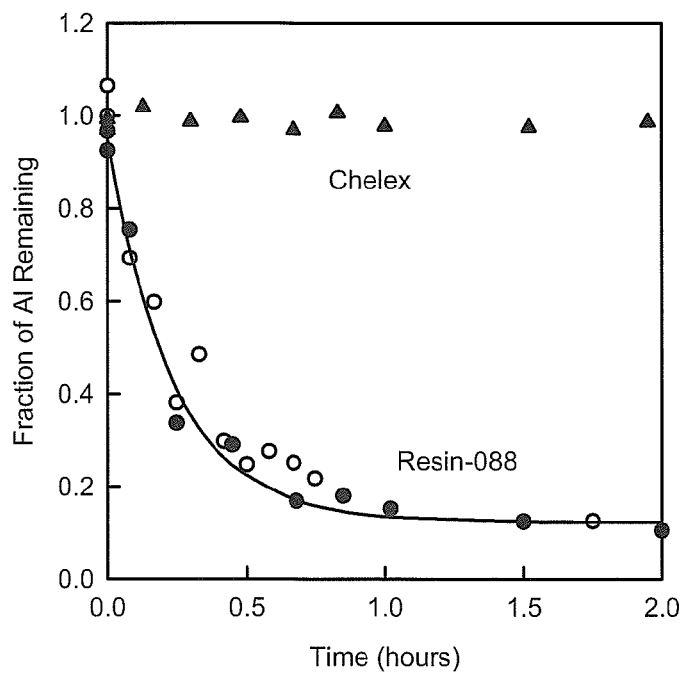

FIG. 7 is a plot of the fraction of Al remaining in a solution of commercial calcium(gluconate), during the extraction of $Al^{3+}$ by resin 9 (filled and open circles) and by the commercial chelating resin Chelex (filled triangles). In each experiment, approximately 240 mg of resin was added to 10 ml of solution. The mixtures were stirred by a magnetic overhead stirrer during the extraction. At periodic times, a 100 μL aliquot was removed from the sample and analyzed by inductively coupled plasma-mass spectrometry to determine the Al concentration.

Figure 8A:
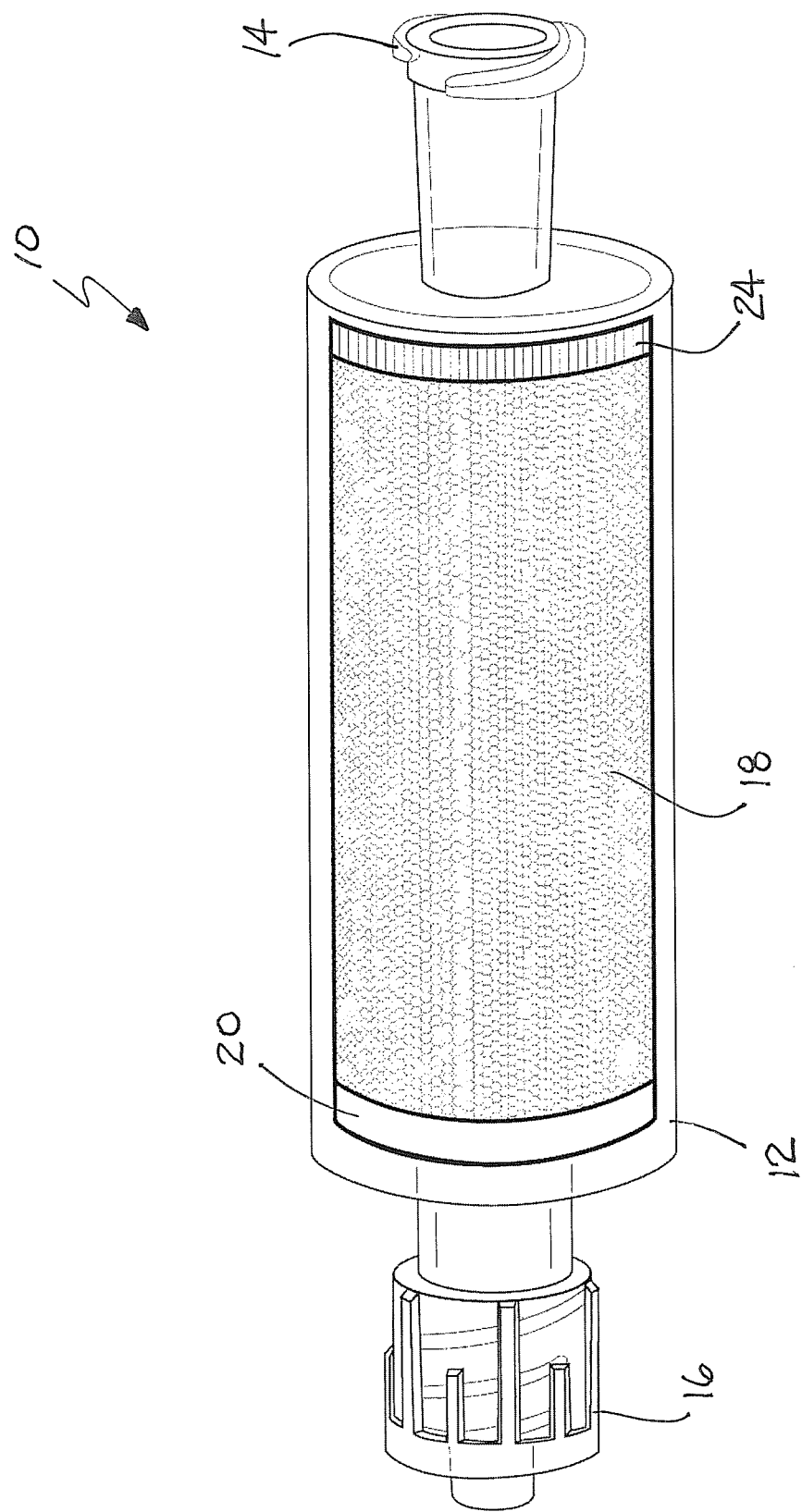
Figure 8B:
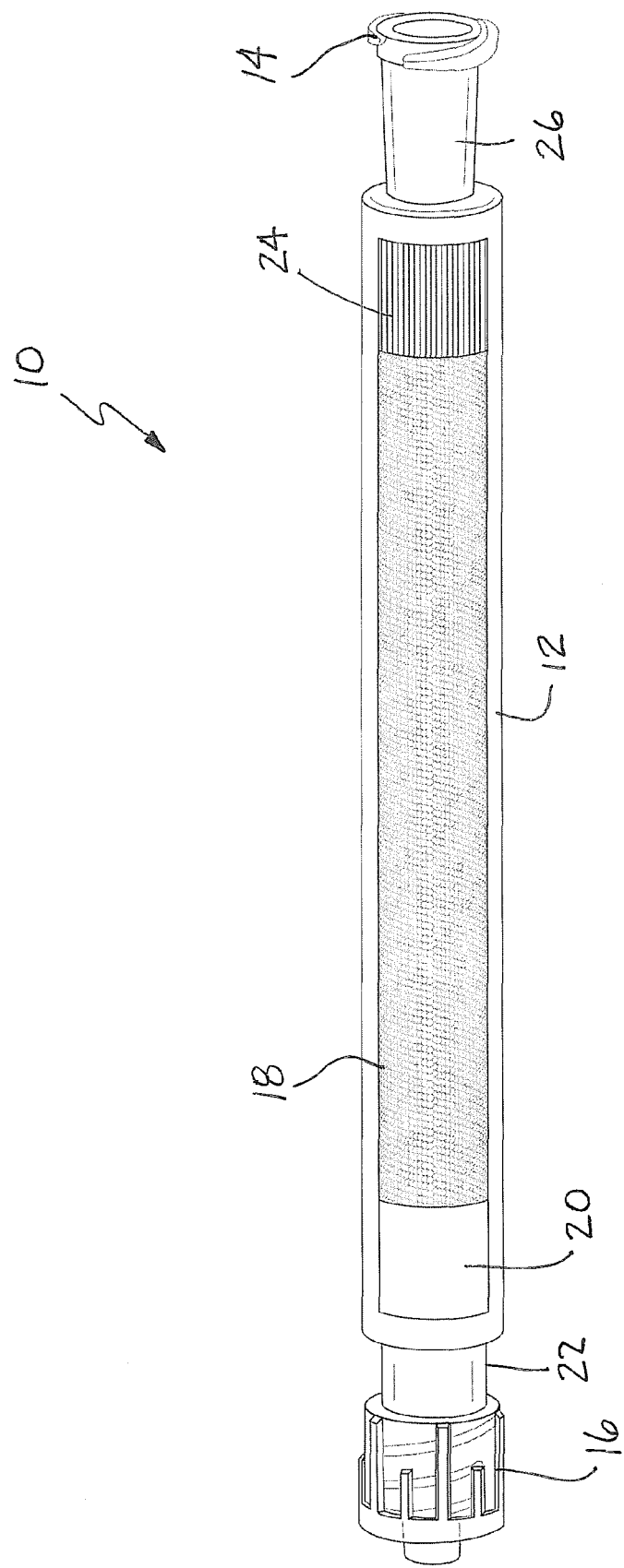
Figure 8C:
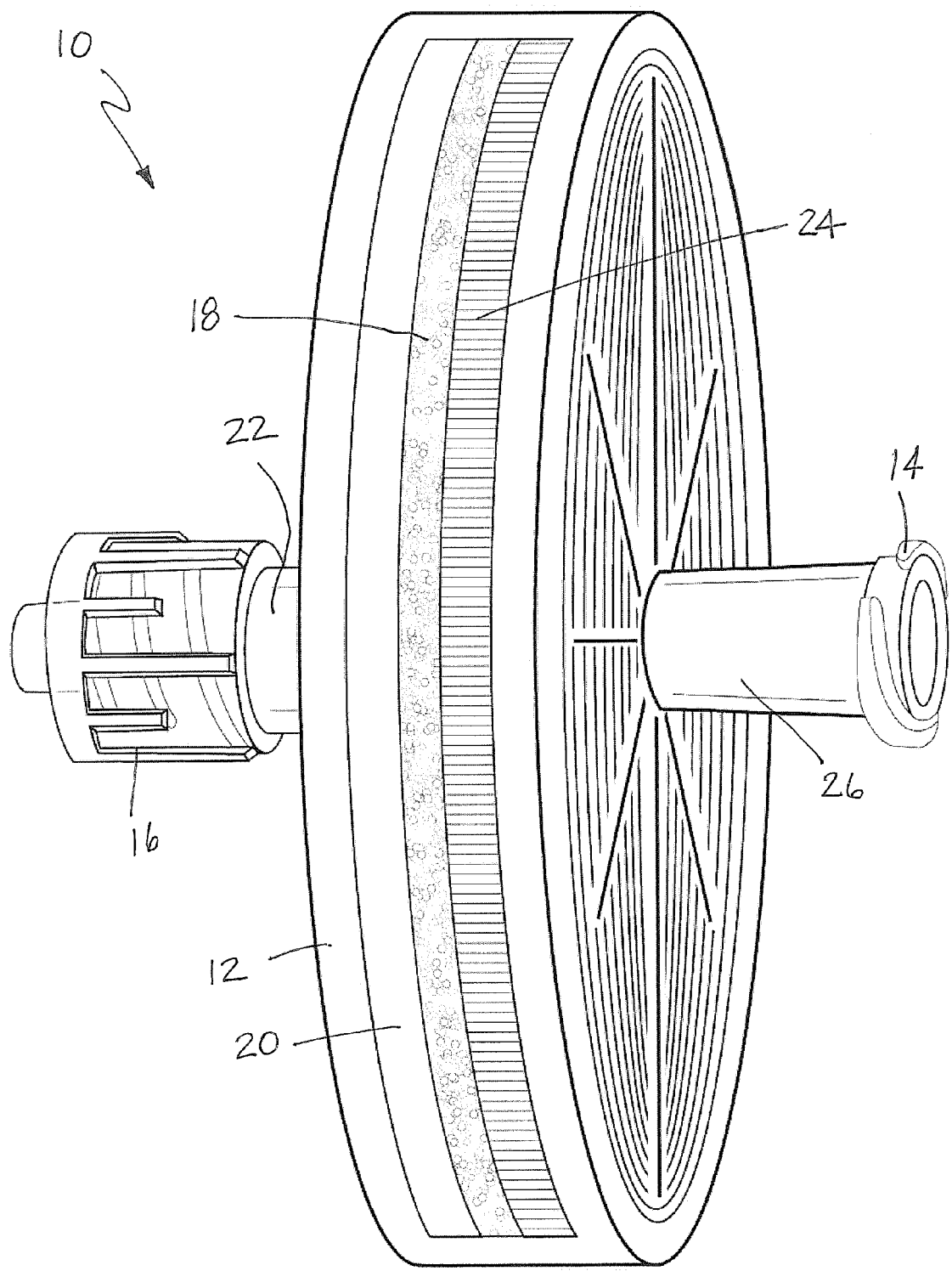

FIGS. 8a-8c illustrate three different embodiments of cartridges that may be filled with the immobilized chelating agents described herein.

Figure 8D:
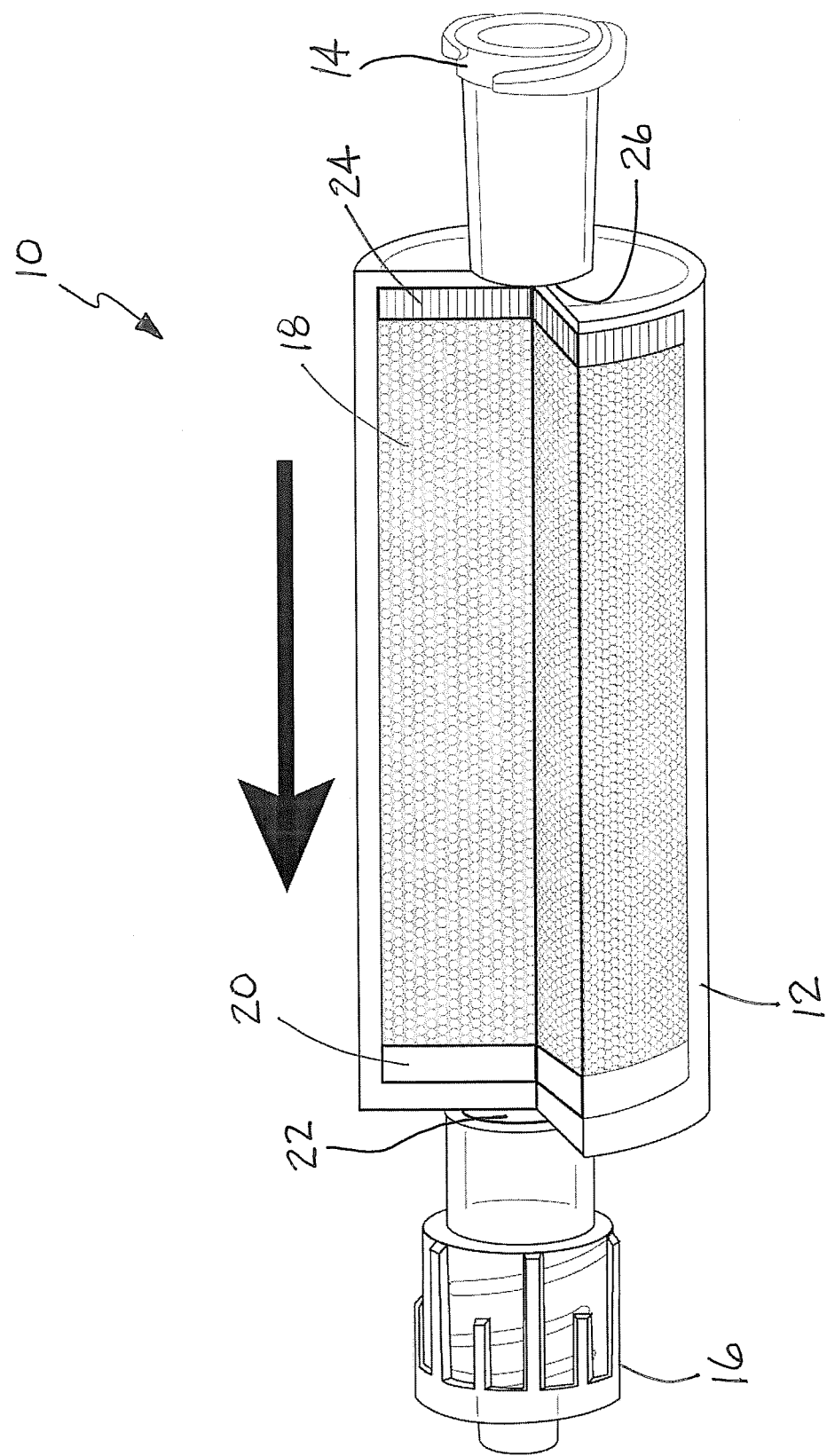

FIG. 8d is a partially cross sectional view of the cartridge illustrated in FIG. 8a.

Figure 9A:
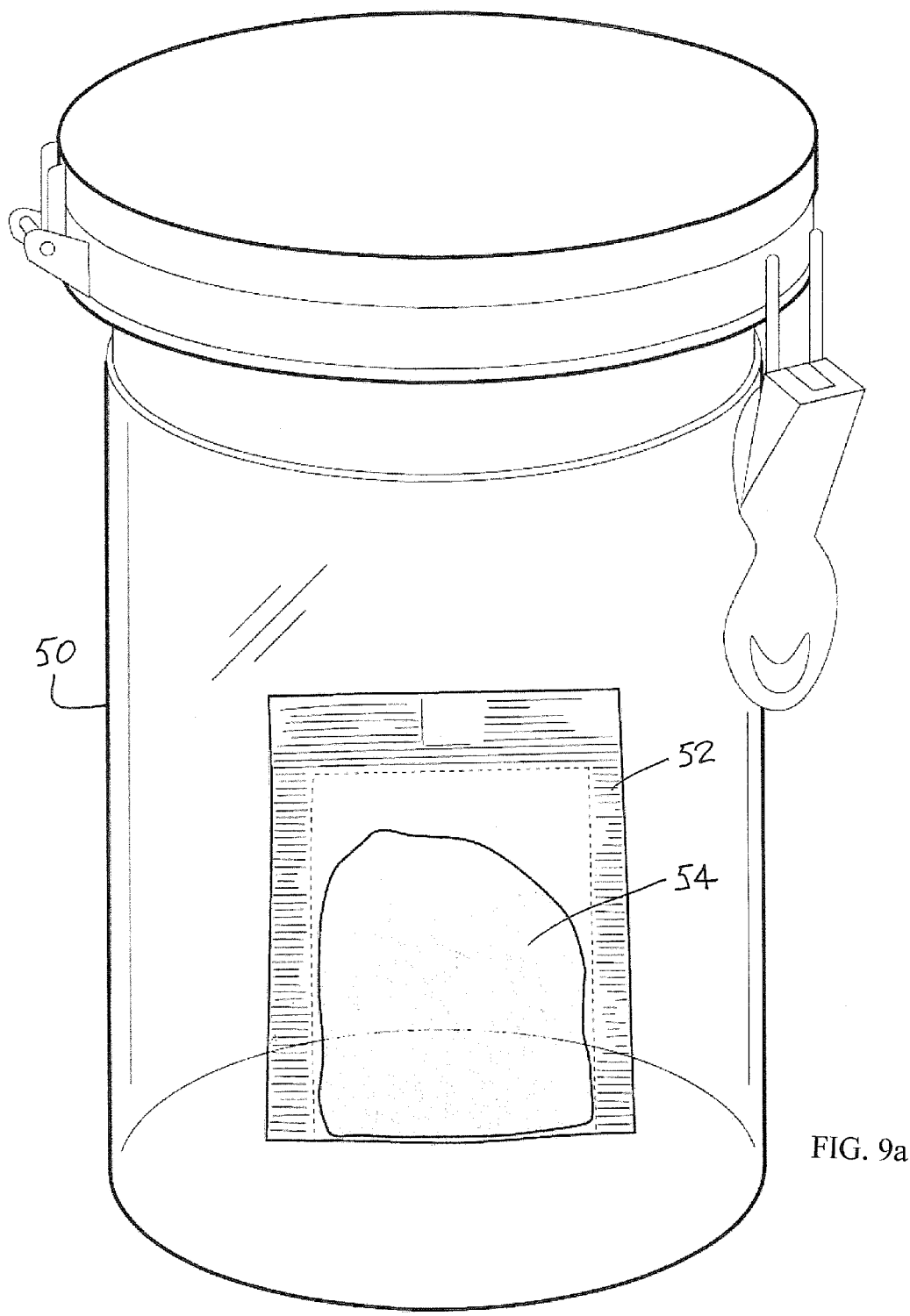
Figure 9B:
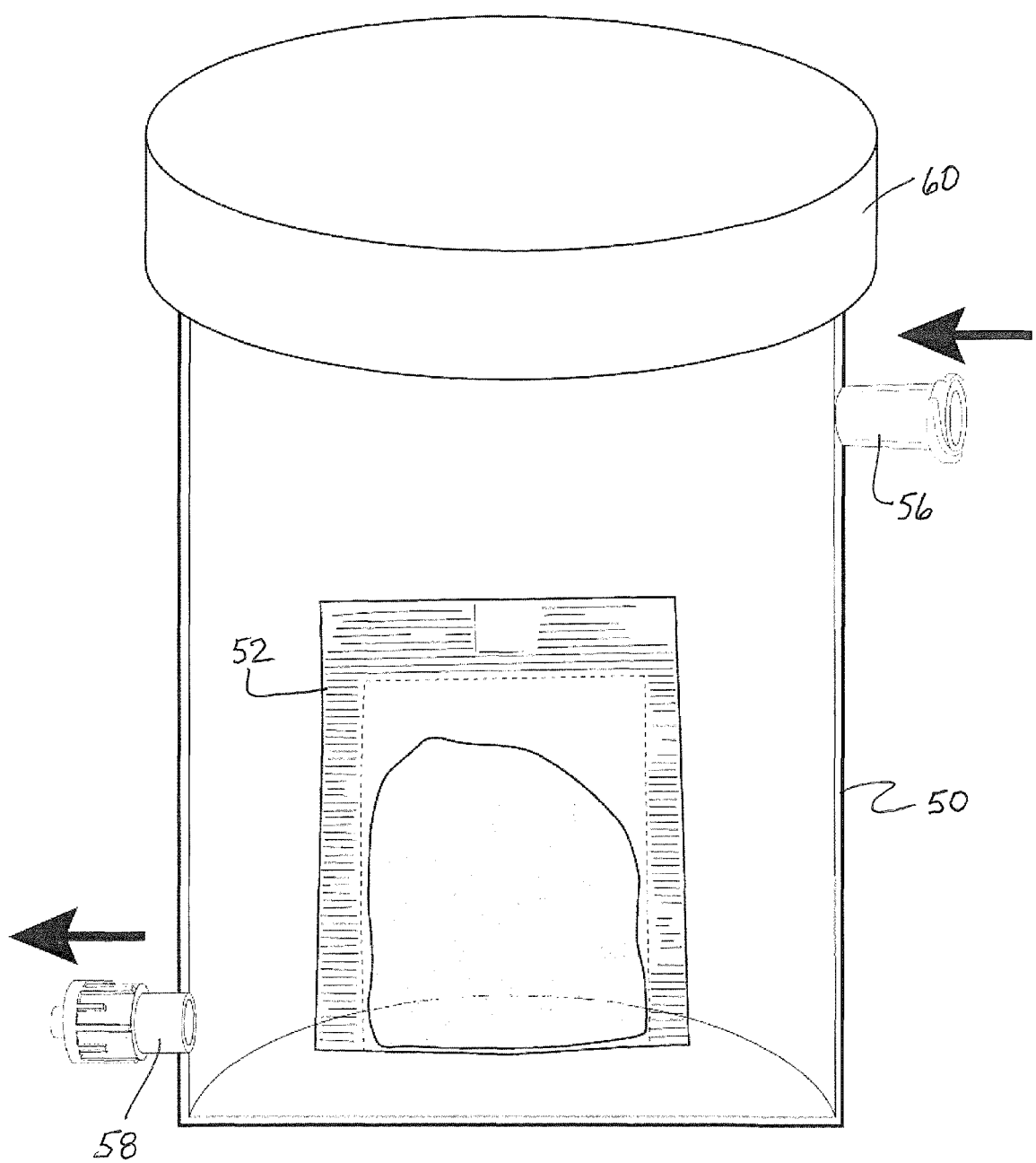
Figure 9C:
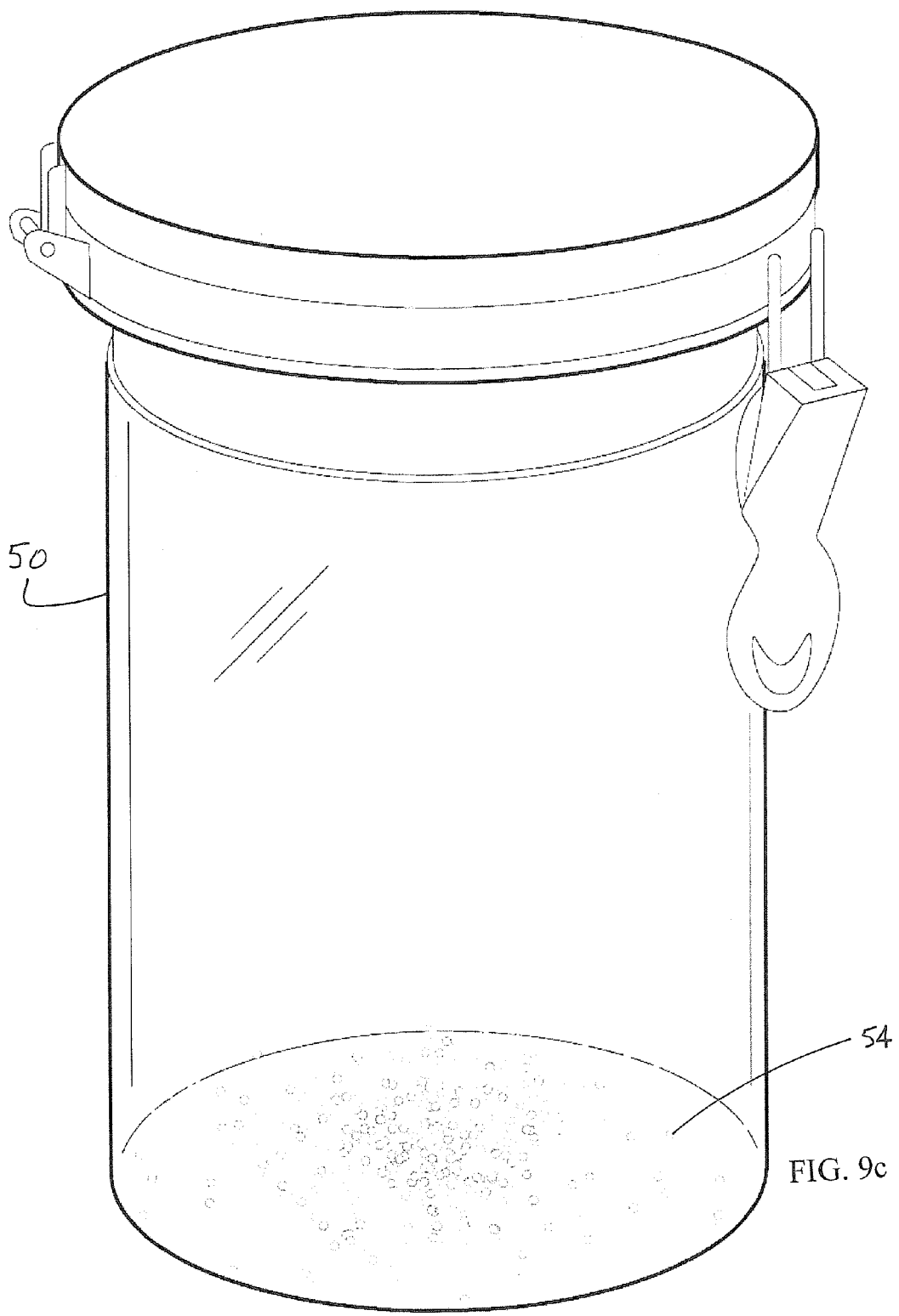

FIGS. 9a-9c illustrate three different embodiments, the first two of a vessel holding a flow-through packet containing the immobilized chelating agents described herein, and the third holding free immobilized chelating agents as described herein.

Figure 10:
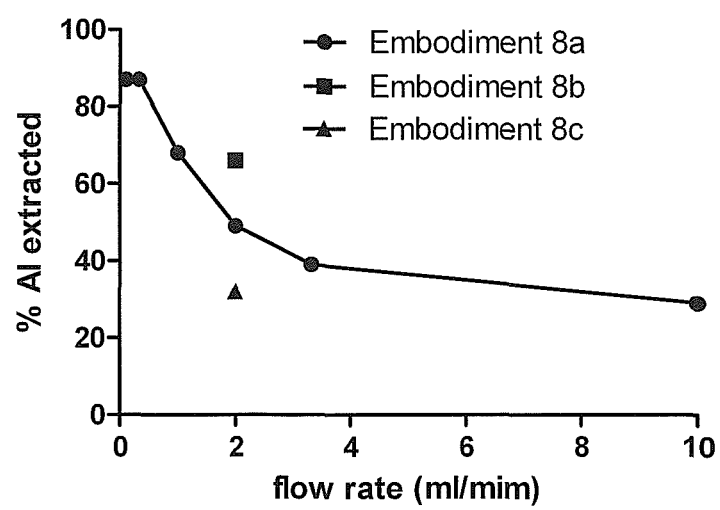

FIG. 10 is a plot of percent removal of Al versus flow rate using the device illustrated in FIG. 8a filled with resin 9.

DETAILED DESCRIPTION OF THE PREFERRED EMBODIMENTS OF THE INVENTION

The present invention relates generally to novel chelating compounds having a general formula of

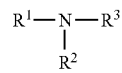

wherein $R^1$=hydrogen or tosylate, $R^2$=hydrogen, methyl, ethyl, n-propyl or isopropyl and
and $R^3$=

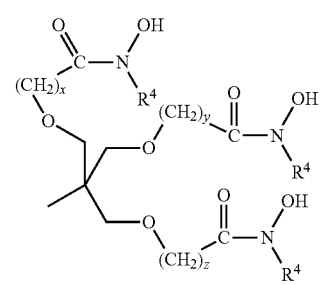

a.)

wherein x, y, and z vary independently from 2 to 4, and $R^4$=hydrogen or $C_1$-$C_{10}$ straight or branched alkyl;

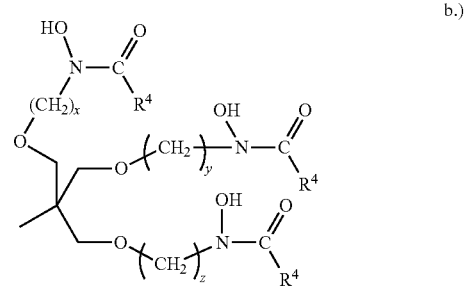

b.)

wherein x, y, and z vary independently from 2 to 4 and $R^4$=hydrogen or $C_1$-$C_{10}$ straight or branched alkyl;

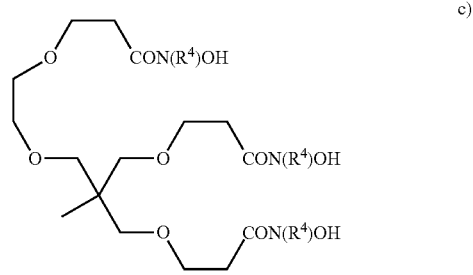

c)

wherein $R^4$=hydrogen or $C_1$-$C_{10}$ straight or branched alkyl;

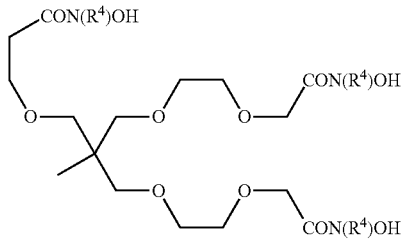
d.)

wherein $R^4$=hydrogen or $C_1$-$C_{10}$ straight or branched alkyl;

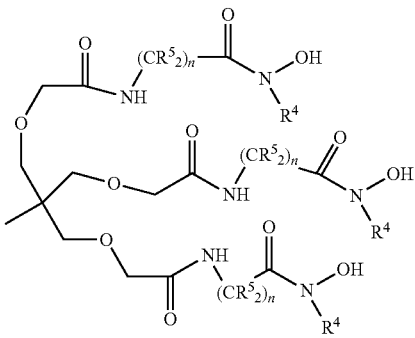
e.)

wherein n=2 or 3, $R^5$=hydrogen or methyl, and $R^4$=hydrogen or $C_1$-$C_{10}$ straight or branched alkyl;

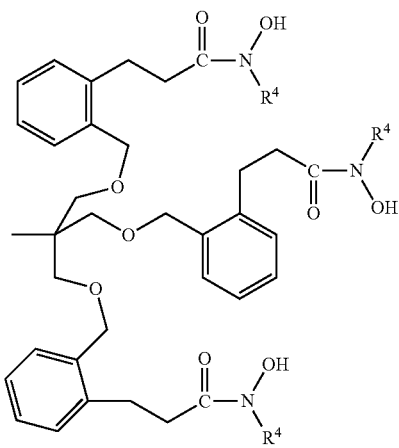
f.)

wherein $R^4$=hydrogen or $C_1$-$C_{10}$ straight or branched alkyl;

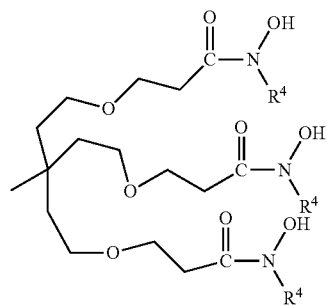
g)

wherein $R^4$=hydrogen or $C_1$-$C_{10}$ straight or branched alkyl; or

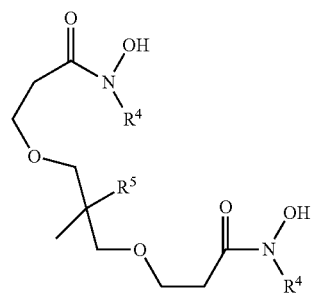
h.)

wherein $R^5$=hydrogen or methyl and $R^4$=hydrogen or $C_1$-$C_{10}$ straight or branched alkyl.

The novel compounds of the present invention are particularly useful as chelators or chelating agents. One preferred use of the free ligands would be in vivo chelation therapy to remove metal ions such as $Fe^{3+}$ and $Al^{3+}$ from the body.

The compounds include an amine functional group that allows the ligands to be easily linked to an insoluble matrix via a sulfonamide linkage, an amide linkage or a urea linkage to provide immobilized, tethered chelators. Typically, the insoluble matrix comprises a resin support. The resin support may take the form of a macro-porous polystyrene such as commercially available under the trademark XAD-4 sold by Rohm and Haas. Other polymer resins useful in the present invention include but are not limited to, polyacrylate, sepharose and silica gel.

The overall process of adding a chelating compound of the present invention to a polystyrene resin via a sulfonamide bond is shown in Scheme 1, where $NR^2H$-Ligand in this and subsequent schemes refers to the free amine form ($R^1$=H; $R^2$=hydrogen, methyl, ethyl, n-propyl or isopropyl) of any of the free ligands represented by $R^3$=a through h.

Scheme 1

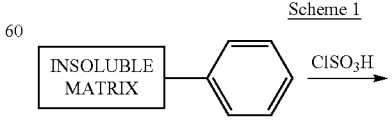

macroporous polystyrene resin, e.g. XAD-4

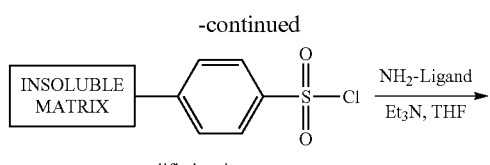

modified resin

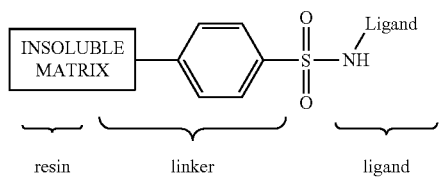

The overall process of adding a chelating compound of the present invention to a resin support by means of an amide linkage is shown in Scheme 2.

Scheme 2

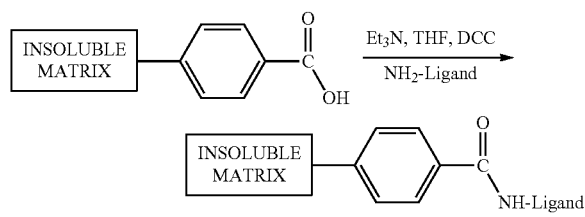

The overall process of adding a chelating compound of the present invention to a resin support by means of a urea linkage is shown in Scheme 3.

Scheme 3

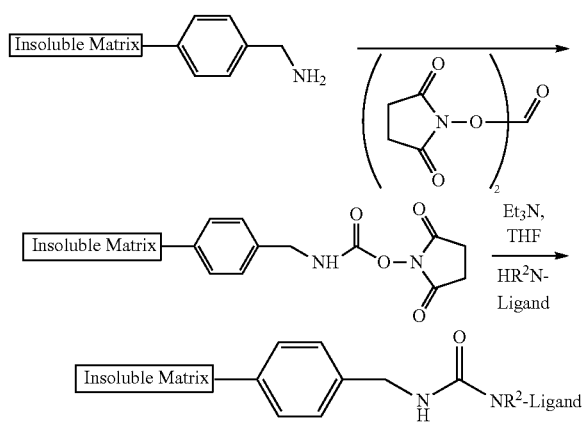

For certain applications it may be desirable to elongate the linker by adding polyethylene glycol units between the resin support and the ligand in order to increase the rate of metal binding to the resin-hound ligand. These elongated linkers are added using commercially available amine capped polyethylene glycols of variable length, with the use of a urea functional group to covalently bind the ligand and linker moieties.

The elongation process is illustrated in Scheme 4 using the linker 3-oxa-1,5-pentanediamine as a specific example.

Scheme 4

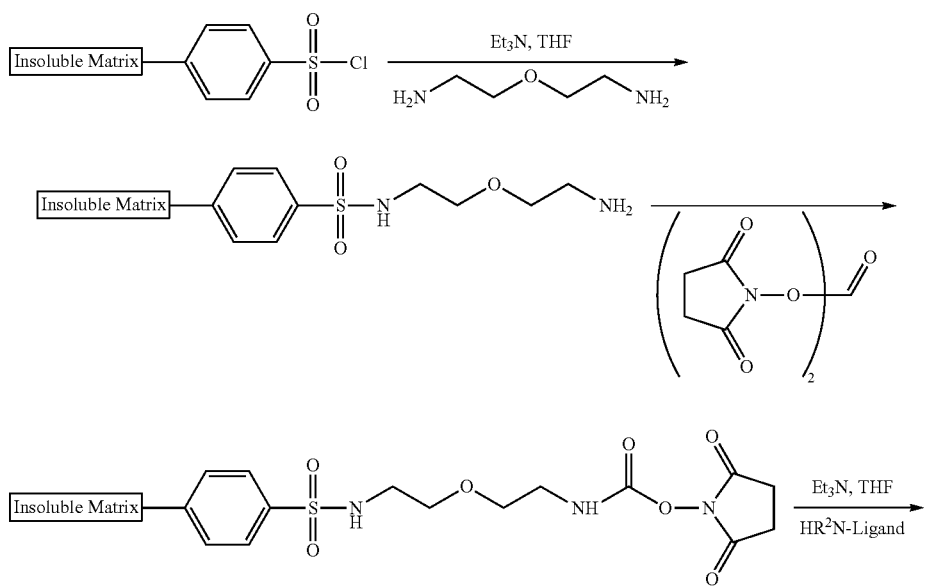

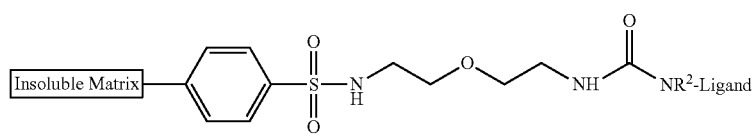

Other commercially available amine-capped polyethyleneglycols include the compounds

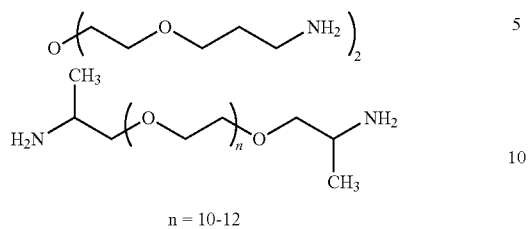

which give chelating resins with the structures shown below

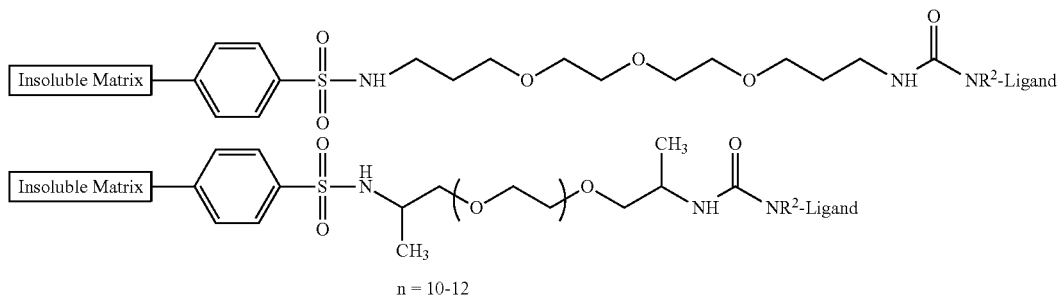

The immobilized, tethered chelators of the present invention comprise the chelating compounds identified above bound to a resin support through an appropriate linkage. The immobilized, tethered chelators of the present invention may be generally described as having the following formula:

wherein $R^6=$

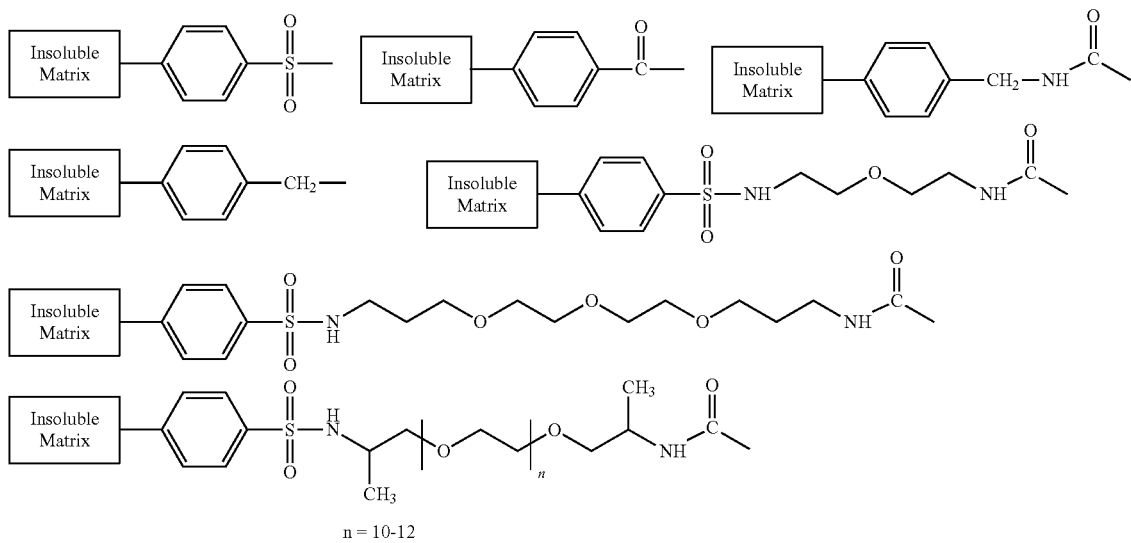

$R^2$=hydrogen, methyl, ethyl; n-propyl or isopropyl and
$R^3$= a.)
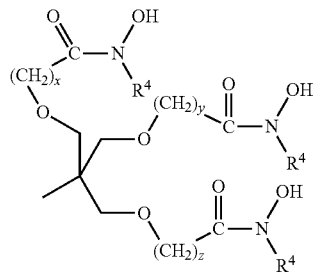

wherein x, y, and z vary independently from 2 to 4 and $R^4$=hydrogen or $C_1$-$C_{10}$ straight or branched alkyl;

b.)
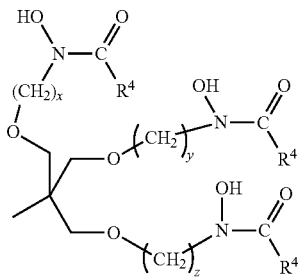

wherein x, y, and z vary independently from 2 to 4, and $R^4$=hydrogen or $C_1$-$C_{10}$ straight or branched alkyl;

c.)
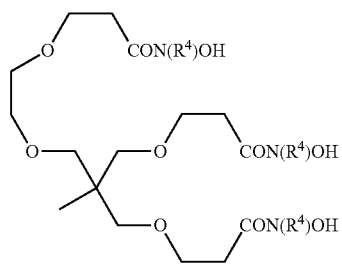

wherein $R^4$=hydrogen or $C_1$-$C_{10}$ straight or branched alkyl;

d.)
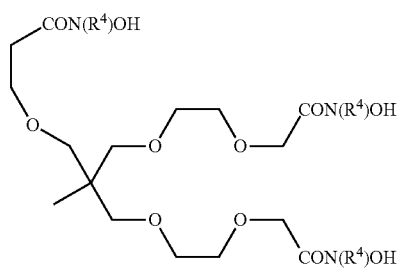

wherein $R^4$=hydrogen or $C_1$-$C_{10}$ straight or branched alkyl;

e.)
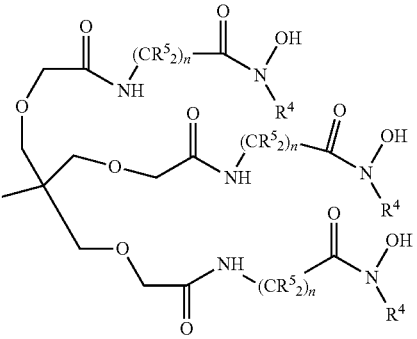

wherein n=2 or 3, $R^5$=hydrogen or methyl, and $R^4$=hydrogen or $C_1$-$C_{10}$ straight or branched alkyl;

f.)
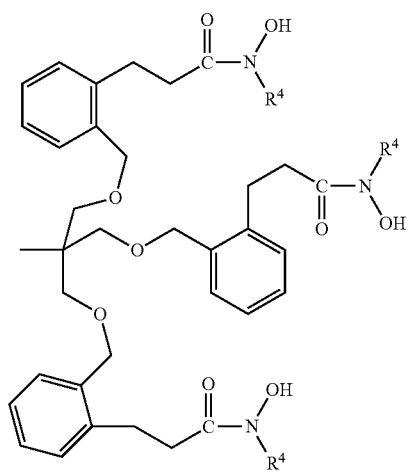

wherein $R^4$=hydrogen or $C_1$-$C_{10}$ straight or branched alkyl;

g)
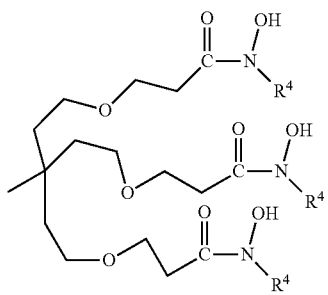

wherein $R^4$=hydrogen or $C_1$-$C_{10}$ straight or branched alkyl; and

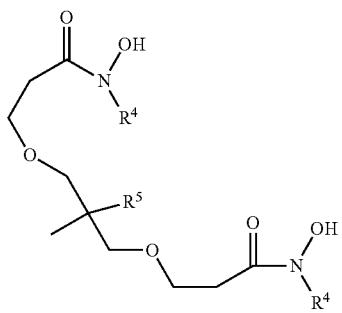

wherein $R^5$=hydrogen or methyl and $R^4$=hydrogen or $C_1$-$C_{10}$ straight or branched alkyl.

Preparation of Compounds of this Invention

Selected chelating agents and chelating resins from this invention are listed in Table 1.

TABLE 1

Partial list of chelating agents and chelating resins included in this invention

| Ligand | $R^3$ | x | y | z | $R^2$ | $R^5$ |
|---|---|---|---|---|---|---|
| Free Ligands ($R^1$ = Tosyl, $R^4$ = H) | | | | | | |
| Ligand 1 | a | 2 | 2 | 2 | H | |
| Ligand 2 | a | 3 | 3 | 3 | H | |
| Ligand 3 | a | 4 | 4 | 4 | H | |
| Ligand 4 | a | 4 | 4 | 2 | H | |
| Ligand 5 | c | | | | H | |
| Ligand 6 | d | | | | H | |
| Ligand 7 | h | | | | | Methyl |
| Ligand 8 | a | 3 | 3 | 2 | H | |
| Ligand 9 | g | | | | | |
| Resins ($R^6$ = polystyrenesulfonate, $R^4$ = H) | | | | | | |
| Resin 1 | a | 2 | 2 | 2 | H | |
| Resin 2 | h | | | | | Methyl |

Example 1

Synthesis of Ligand 1

The overall synthesis of Ligand 1 is shown in Scheme 5. The aminotriol (1. Tris buffer) was reacted with acrylonitrile in the presence of a catalytic amount of base to give the trinitrile (Intermediate 1) (Newkome, G. R. and X. Lin, *Symmetrical, four-directional, poly(ether-amide) cascade polymers*. Macromolecules. 1991, 24(6): 1443-1444). Reaction of Intermediate 1 in refluxing methanolic HCl gave the tris(methyl ester) (Intermediate 2). Reaction of Intermediate 2 with tosyl chloride gave the sulfonamide tris ester (Intermediate 3). This ester was converted to the trihydroxamic acid (Ligand 1) by reaction with O-trimethylsilyl hydroxylamine ($NH_2OTMS$) in methanol.

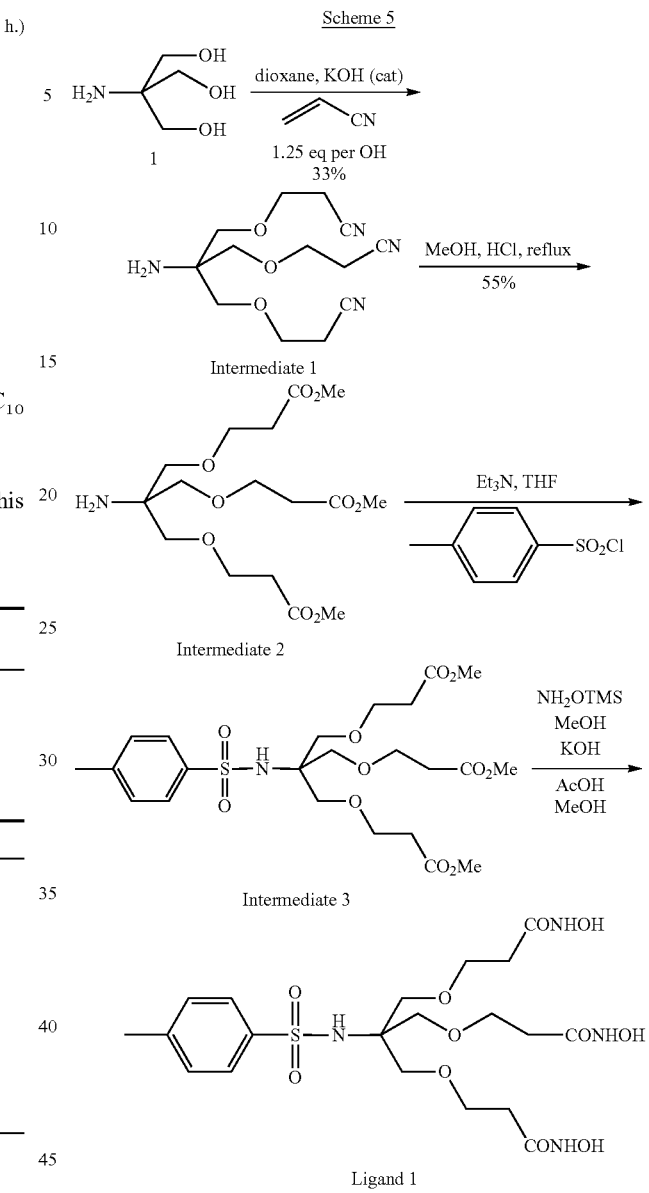

Scheme 5

Synthesis of Intermediate 1

To a stirred solution of tris(hydroxymethyl)aminomethane (50.0 g, 412.0 mmol) and KOH (2.3 g, 4.5% of the weight of alcohol) in 1,4-dioxane (150 mL) was added acrylonitrile (71.17 g, 1342.4 mmol) drop wise over a period of 1 h, after which a clear solution was obtained. After stirring at room temperature for 24 h, the mixture was made acidic (~pH=2) by the addition of dil. HCl. After extraction with $CH_2Cl_2$ (3×100 mL) the combined organic layers were dried over sodium sulfate and evaporated to give tris[(cyanoethoxy)methyl]aminomethane (Intermediate 1), 43.2 g (33.5%). IR (neat) 3588, 3368, 2251 $cm^{-1}$; $^1H$ NMR ($CDCl_3$) δ 3.68 (t, J=6.0 Hz, 6H), 3.44 (s, 6H), 2.61 (t, J=6.0 Hz), 1.68 (br s, 2H); $^{13}C$ NMR ($CDCl_3$) δ 118.2, 72.7, 65.9, 56.3, 19.0; HRMS (EI, $MH^+$) calcd for $C_{13}H_{21}N_4O_3$: 281.16147. found: 281.16138. (Newkome, G. R. and X. Lin, *Symmetrical, four-directional, poly(ether-amide) cascade polymers*. Macromolecules, 1991. 24(6): p. 1443-1444.

Synthesis of Intermediate 2

Dry HCl gas was passed through a solution of intermediate 1 (52.6 g, 187.0 mmol) in dry methanol (150 mL) until the solution was saturated with HCl. The mixture was refluxed overnight. After the solution was cooled, $NH_4Cl$ was removed by filtration, and the filtrate was concentrated to give a gum. The gum was taken up in THF, filtered, and the filtrate was concentrated to get the tris ester (Intermediate 2) 37.0 g (55.0%). IR (neat) 3394, 1735 $cm^{-1}$; $^1H$ NMR ($CDCl_3$) δ 3.69 (t, $^2J_{h-h}$=6.31 Hz, 6H), $^{13}C$ NMR ($CDCl_3$) δ 172.4, 69.0, 67.1, 59.6, 52.0, 34.7; HRMS (EI, $MH^+$) calcd for $C_{16}H_{30}NO_9$: 380.19217. found: 380.19205. (Nierengarten, J. F.; Habicher, T.; Kessinger, R.; Cardullo, F., Diuederich, F.; Gramlich, V.; Gisselbrecht, J. P.; Boudon, D.; Gross, M., *Macrocylization on the fullerene core. Direct regio-and diasterioselective multi-functionalization of [60]ffullerene, and synthesis of fullerene-dendrimer derivatives*. Helv. Chim. Acta, 1997, 80: 2238-2276).

Synthesis of Intermediate 3

To a stirred solution of tosyl chloride (10.0 g, 52.4 mmol) and the tris ester (Intermediate 2) (19.90 g, 52.4 mmol) in $CH_2Cl_2$ was added $NEt_3$ (6.37 g, 62.9 mmol) and the mixture was heated at reflux overnight. The solvent was removed in vacuo, and the residue was redissolved in $CH_2Cl_2$ (200 mL) and washed with water (3×100 mL). The organic layer was dried over $Na_2SO_4$ and concentrated to give a gum. Column chromatography using silica gel with 50% ethyl acetate in hexane yielded a gummy solid of Intermediate 3 (20.4 g, 73%), which later crystallized on storing at room temperature. Finally it was characterized by X-ray crystallography. IR (neat) 3610, 3287, 1736 $cm^{-1}$; $^1H$ NMR ($CDCl_3$) δ 7.78, 7.76, 7.27, 7.24 (s each, 4H), 3.68 (s, 9H), 3.51 (s, 6H), 3.51 (t, $^2J_{h-h}$=6.5 Hz, 6H), 2.41 (t, $^2J_{h-h}$=6.5 Hz, 6H) 2.41 (s, 3H); $^{13}C$ NMR ($CDCl_3$) δ 172.1, 142.8, 140.5, 129.2, 127.0, 69.9, 66.7, 62.4, 51.9, 34.7, 21.6; HRMS (EI, $MH^+$) calcd for $C_{23}H_{36}NO_{11}S$: 534.20095. found: 534.20093.

Synthesis of Ligand 1

To a stirred solution of the tris(ester) (Intermediate 3) (8.23 g, 15.4 mmol) in methanol (100 mL) was added $NH_2TMS$ (9.74 g, 92.5 mmol) followed by KOH (2.60 g, 46.0 mmol). After 6 h at room temperature, the reaction mixture was treated with 20 g of prewashed Amberlyst-15 and swirled for 1 h. The resin was filtered off and the filtrate was evaporated to give a gum. Recrystallization from acetone:hexane (1:1) yielded the tris hydroxamate (Ligand 1), 5.02 g, (61%) which was characterized by X-ray crystallography. IR (neat) 3184, 1631 $cm^{-1}$; $^1H$ NMR ($CDCl_3$) δ 7.76, 7.73, 7.42, 7.39 (s each, 4H), 3.46 (t, J=5.8 Hz, 6H), 3.40 (s, 6H), 3.31 (s, 3H, MeOH), 2.40 (s, 3H), 2.30 (t, J=5.8 Hz, 6H); $^{13}C$ NMR ($CDCl_3$) δ 171.1, 145.0, 139.0, 130.1, 127.0, 69.2, 67.0, 63.0, 49.2 ($CH_3OH$), 33.3, 21.0 HRMS (EI, $MH^+$) calcd for $C_{20}H_{33}N_4O_{11}S$: 537.18677. found: 537.18665.

Example 2

Synthesis of Ligand 2

The overall synthesis of Ligand 2 is shown in Scheme 6. The trimethyl orthoester of 4-iodo-1-butyric acid (3), in which the vulnerable $sp^2$ carbon has been protected, is known to alkylate alkoxides (Srivastava, R. P., Hajda, J. *Stereospecific synthesis of ether phospholipids. Preparation of 1-O-(3'-carboxypropyl)-glycero-3-phosphoserine from glyceric acid*. Tetrahedron Lett. 1991, 32, 6525-6528) (Method A). Thus treatment of the BOC-protected triol (2) with sodium hydride and the trimethyl ortho ester (3) in DMF, followed by deprotection with anhydrous methanolic HCl gives the triester (Intermediate 4). Alternatively, reductive alkylation of the trimethylsilylated triol (BSA, reflux) with 3-cyanopropionaldehyde (Iwanami, K., Kentaro Y., Takeshi, O. *An Efficient and Convenient Method for the Direct Conversion of Alkyl Silyl Ethers into Corresponding Alkyl Ethers Catalyzed by Iron (III) Chloride*. Synthesis 2005, 2669-2672) (Method B), followed by treatment with anhydrous HCl in refluxing methanol should also yield intermediate 4. Intermediate 4 is tosylated to give Intermediate 5, which is then converted to the corresponding hydroxamic acid (Ligand 2) by treatment with O-(trimethylsilyl)hydroxylamine.

Scheme 6

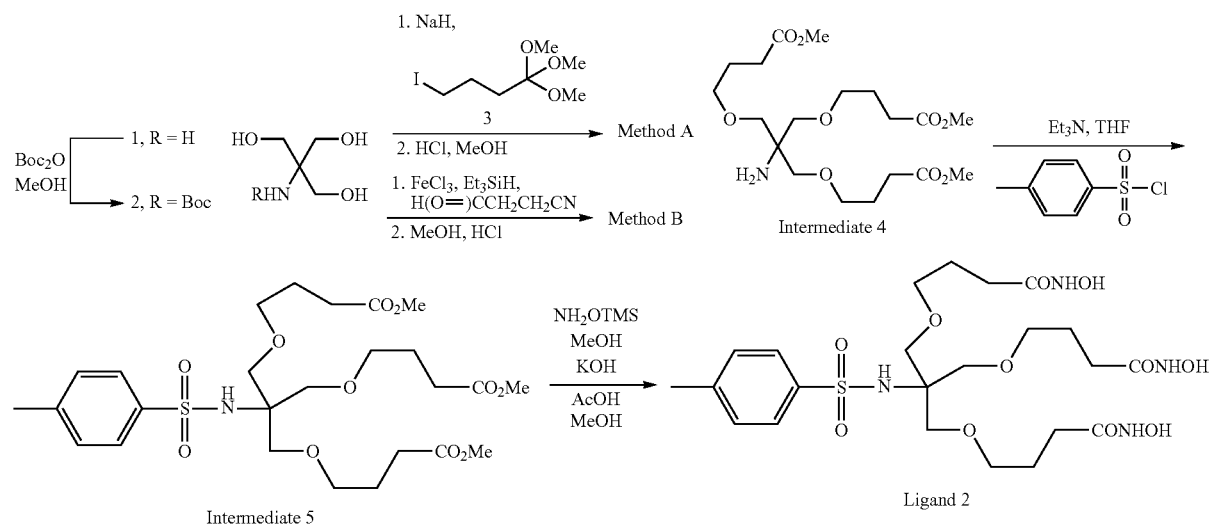

Example 3

Synthesis of Ligand 3

The overall synthesis of Ligand 3 is shown in Scheme 7. Treatment of the BOC-protected triol (2) with sodium hydride and the trimethyl ortho ester or 5-iodo-1-pentanoic acid (4) in DMF, followed by deprotection with anhydrous methanolic HCl gives the triester (Intermediate 6). Alternatively, reductive alkylation of the trimethylsilylated triol (Bis silylacetamide, reflux) with 4-cyanobutryoaldehyde (Iwanami, K., Kentaro Y., Takeshi, O. *An Efficient and Convenient Method for the Direct Conversion of Alkyl Silyl Ethers into Corresponding Alkyl Ethers Catalyzed by Iron (III)Chloride*. Synthesis 2005, 2669-2672) (Method B), followed by treatment with anhydrous HCl in refluxing methanol should also yield intermediate 6. Intermediate 6 is tosylated to give Intermediate 7, which is then converted to the corresponding hydroxamic acid (Ligand 3) by treatment with O-(trimethylsilyl)hydroxylamine).

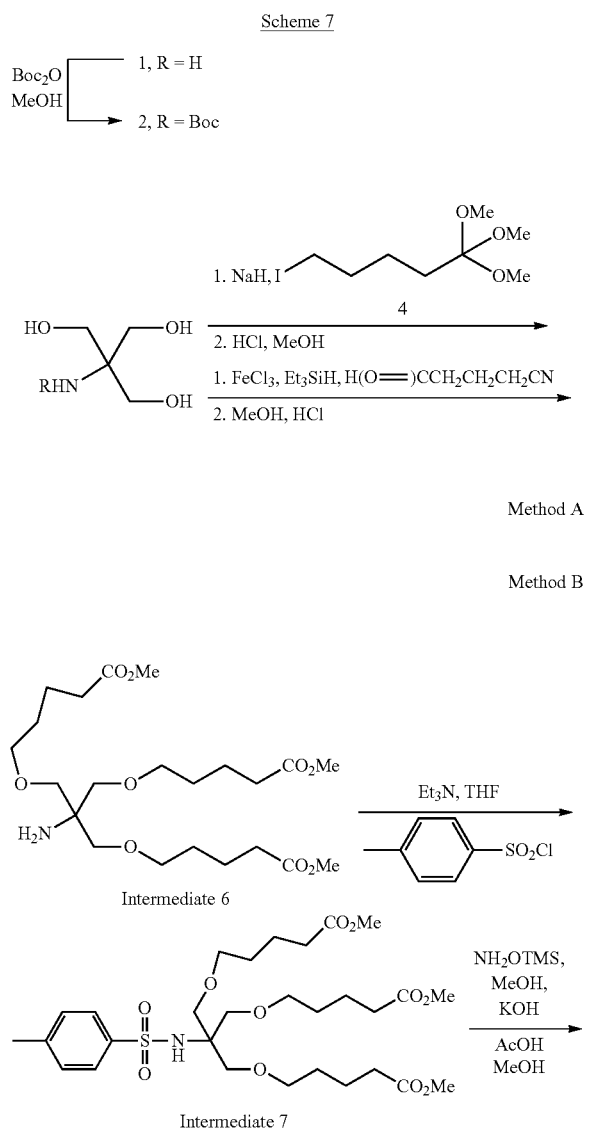

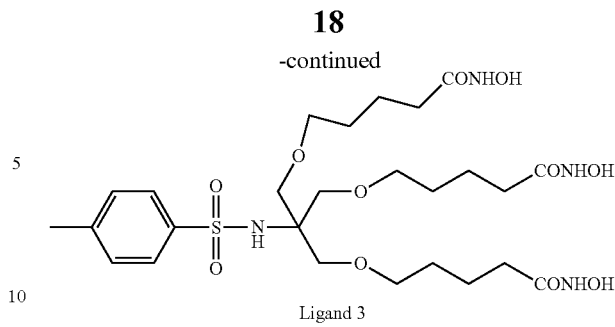

Ligand 3

Example 4

Synthesis of Ligand 4. The binding constants for Ligand 1 (see below) indicate that two arms of the ligand bind to metal ions very strongly, but that steric hindrance weakens the binding of the third arm. In the heteropodal Ligand 4, the length of two of the ligand arms have been extended to relieve this internal strain. The synthesis of ligand 4 is shown in Scheme 8. To prepare heteropodal trihydroxamic ligands, two of the hydroxyls on the aminotriol (tris) are first blocked by a protecting group. The aminotriol (1) is converted to the known cyclic acetal (5) using a published 2 step, 1 pot procedure (Ooi, H., Ishibashi, N., Iwabuchi, U., Ishihara, J., Hatakeyama, S. *A concise Route to (+)-Lactacystin*. J. Org. Chem. 2004, 69, 7765-7768). Alternatively, the diol can be protected as the benzylidene (6a) (Balakumar, V., *A highly regio-and chemoselective reductive cleavage of benzylidene acetals with EtAlCl₂-Et₃SiH*, Synlet, 2004, 647-650; Low, J. N., B. F. Milne, J.-N. Ross, and J. L. Wardell, *Derivatives of N,N'-bis[2-Hydroxy-1,1-bis(hydroxymethyl)ethyl]ethanediamide*. Journal of the Brazilian Chemical Society, 2002, 13: 207-217) using similar reaction conditions, which results in additional options for deprotection later in the synthetic sequence. Addition of the remaining free alcohol to acrylonitrile yields the mononitrile (7) (Newkome, G. R., Lin, X. *Symmetrical, four-directional, poly(ether-amide) cascade polymers*. Macromolecules. 1991, 24, 1443-1444). Simultaneous deprotection of the acetal and methanolysis of the nitrile with a refluxing solution of methanolic HCl yields the monoester-diol (8). The diol is then alkylated by the addition of the trimethyl ortho ester of 5-iodopentanoic acid to form the triester (Intermediate 8). An additional complication in the alkylation of the monoester diol is base-catalyzed beta elimination of the alkoxy group beta to the ester. Intermediate 8 is tosylated to give Intermediate 9, which is converted to the corresponding trihydroxamate (Ligand 4) by the addition of O-(trimethylsilyl)hydroxylamine.

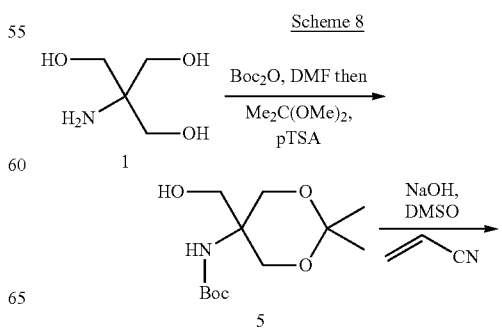

Scheme 8

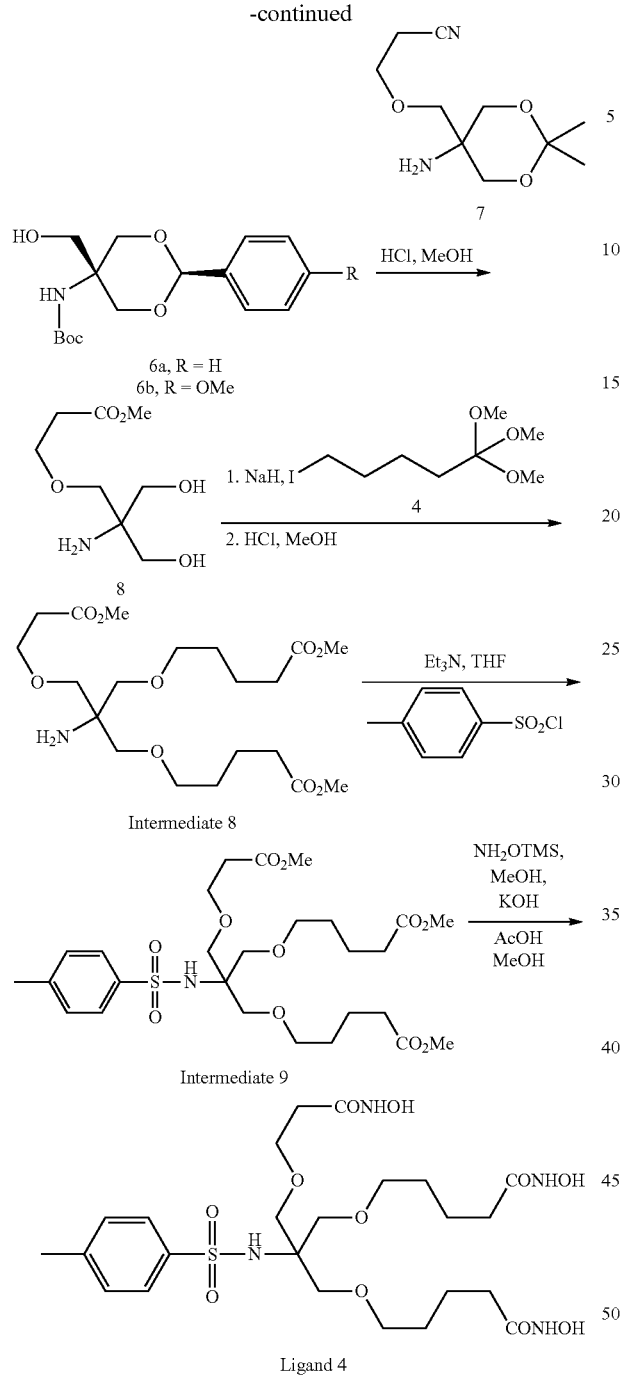
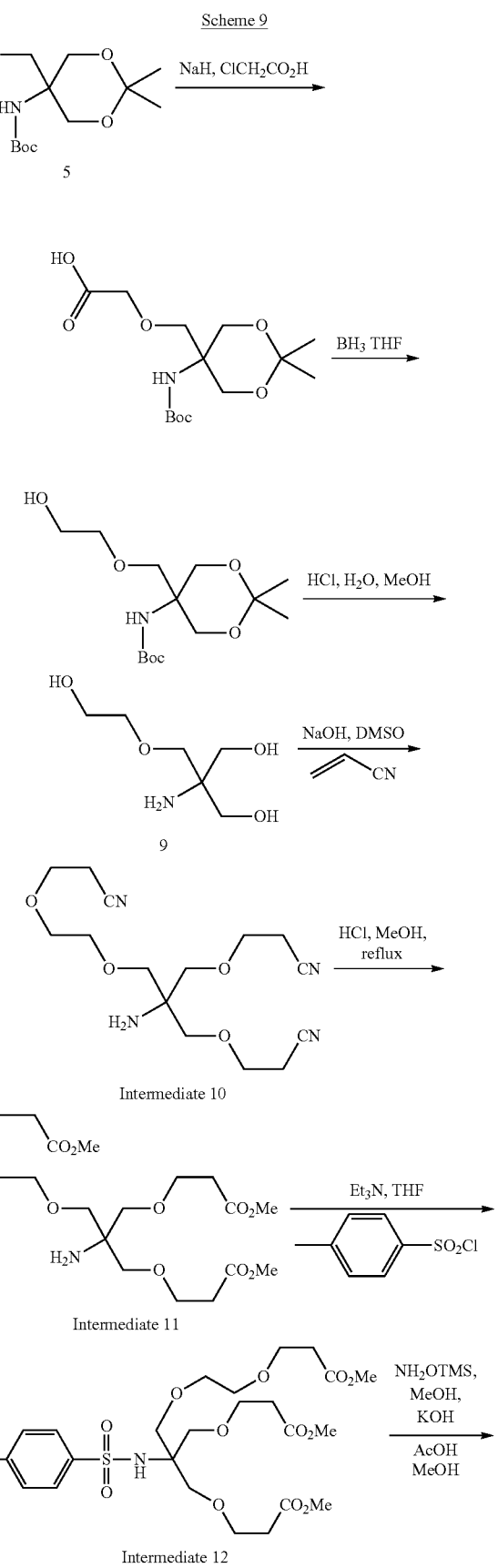

Example 5

Synthesis of Ligand 5. The synthesis of the heteropodal Ligand 5 is described in Scheme 9. The extension of one arm of the ligand is achieved by the reaction of the acetal protected aminotriol (5) with chloroacetic acid, followed by selective reduction of the carboxylic acid and deprotection of the cyclic acetal to give the unsymmetric triol (9). Adding the triol to acrylonitrile gives the trinitrile Intermediate 10, and methanolysis of the nitrile gives the tris(ester) (Intermediate 11). This compound is tosylated to give Intermediate 12. The addition of O-(trimethylsilyl)hydroxylamine to Intermediate 12 gives the heteropodal Ligand 5.

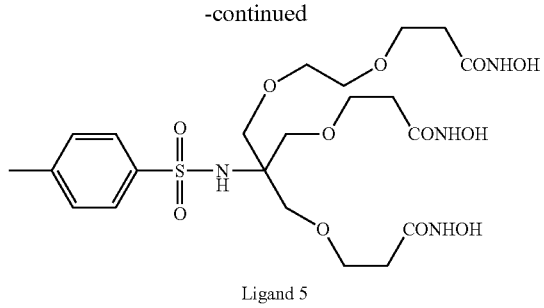

Ligand 5

Example 6

Synthesis of Ligand 6

The synthesis of Ligand 6 is shown in Scheme 10. The diol (8) from Scheme 8 is reprotected at the amine with a Boc group to give (10). The remaining hydroxyls are reductively alkylated with aldehyde (11) followed by methanolysis to yield the triester (Intermediate 13). The aldehyde (11) is easily prepared in two steps from glycol. Although synthesis of the ester (12) would provide a more direct approach, the reaction would be complicated by competing, rapid lactonization to lactone (13). Intermediate 13 is tosylated to give intermediate 14. This compound is treated with O-(trimethylsilyl)hydroxylamine to give the heteropodal trihydroxamic acid Ligand 6.

Scheme 10

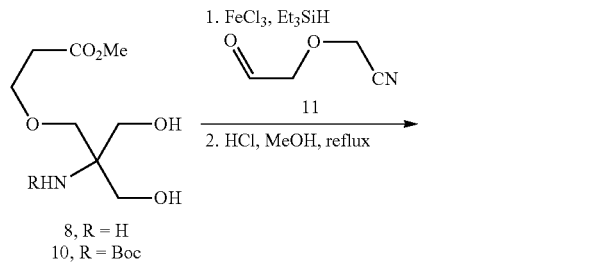

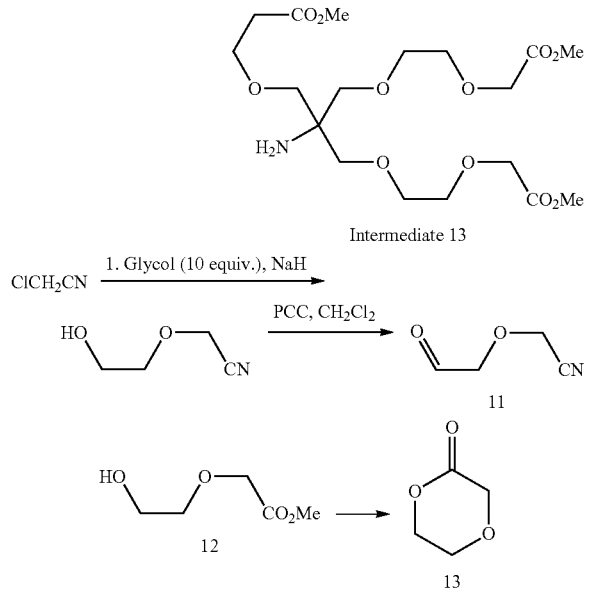

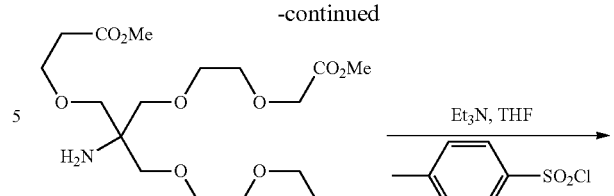

Intermediate 13

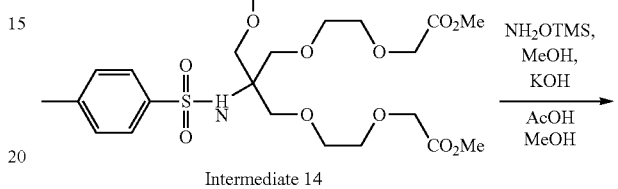

Intermediate 14

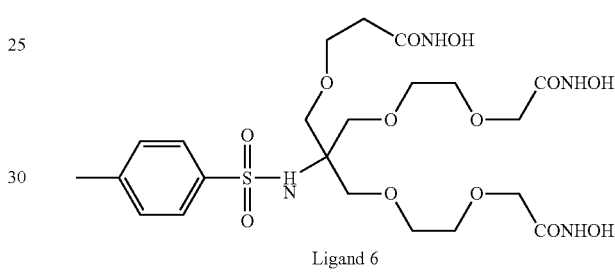

Ligand 6

Example 7

Synthesis of Ligand 7. The overall synthesis of Ligand 7 is shown in Scheme 11.

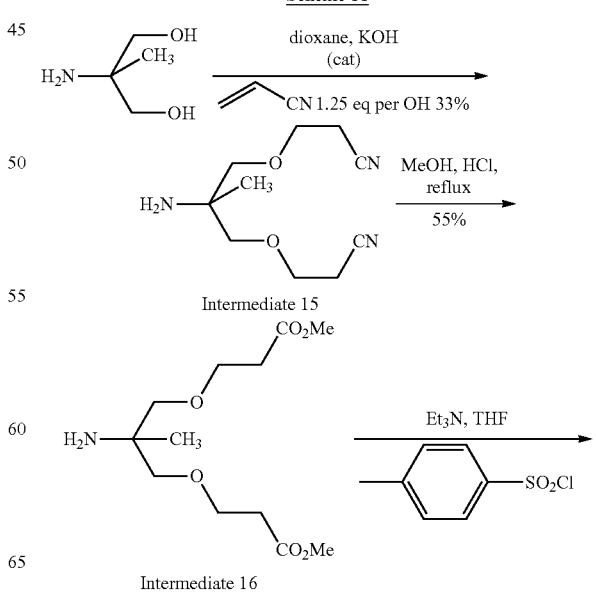

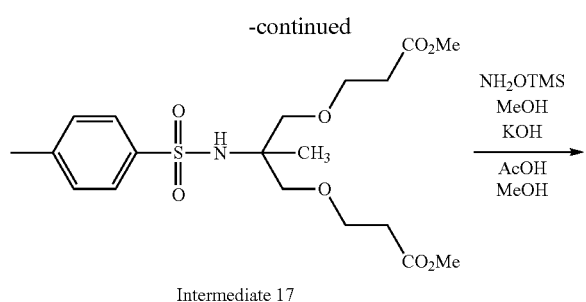

Intermediate 17

Synthesis of Intermediate 15

To a stirred solution of 2-amino-2-methyl-1,3-propanediol (50.0 g, 475.5 mmol) and KOH (1.0 g, 2% of the weight of diol) in 1,4-dioxane (100 mL) was added acrylonitrile (56.7 g, 1070.0 mmol) dropwise over a period of 1 h, after which a clear solution was obtained. After stirring at room temperature for 24 h, 200 mL of $CH_2Cl_2$ was added to the mixture. The mixture was extracted with water and the organic layer was dried over sodium sulfate. The solvent was evaporated to yield a thick oil. Distillation under reduced pressure (160□ C/10 mm Hg) yielded Intermediate 15, 39.5 g (39%). IR (neat) 3517, 3360, 2250 cm$^{-1}$; $^1$H NMR (CDCl$_3$) δ 3.68 (t, J=6.1 Hz, 4H), 3.33 (Abq, Δv=14.2 Hz, J=8.5 Hz, 4H), 2.60 (t, J=6.1 Hz, 4H), 1.44 (br s, 2H), 1.06 (s, 3H; $^{13}$C NMR (CDCl$_3$) δ 118.2, 76.5, 65.8, 52.8, 22.6, 19.0 HRMS (EI, MH$^+$) calcd for $C_{10}H_{18}N_3O$: 212.14002. found: 212.13989.

Synthesis of Intermediate 16

Dry HCl gas was passed through a solution of Intermediate 16 (39.48 g, 186.1 mmol) in dry methanol (150 mL) until the solution was saturated with HCl. The mixture was refluxed overnight. After cooling, NH$_4$Cl was removed by filtration, and the filtrate was concentrated to give a gum. The gum was redissolved in THF, filtered, and the filtrate was concentrated to get the diester (Intermediate 16) 30.0 g (57.0%). IR (neat) 3409, 1727 cm$^{-1}$; $^1$H NMR (CDCl$_3$) δ 3.79 (t, J=6.1 Hz, 2H), 3.70 (2, 6H), 3.62 (s, 4H), 2.64 (t, J=6.1 Hz, 4H), 1.42 (s, 3H); $^{13}$C NMR (CDCl$_3$) δ 172.6, 71.7, 67.2, 58.0, 52.1, 34.8, 18.4; HRMS (EI, MH$^+$) calcd for $C_{12}H_{24}NO_6$: 278.16047. found: 278.16037.

Synthesis of Intermediate 17

To a stirred solution of tosyl chloride (10.0 g, 52.4 mmol) and Intermediate 16 (14.54 g, 52.4 mmol) in $CH_2Cl_2$ was added NEt$_3$ (6.37 g, 62.9 mmol) and the mixture was heated at reflux overnight. The solvent was removed in vacuo, and the residue was redissolved in $CH_2Cl_2$ (200 mL) and washed with water (3×100 mL). The organic layer was dried over Na$_2$SO$_4$ and concentrated to give a gum. Column chromatography using silica gel with 40% ethyl acetate in hexane yielded a gummy solid of Intermediate 17, (16.9 g, 74%). IR (neat) 3604, 1736, 1735 cm$^{-1}$; $^1$H NMR (CDCl$_3$) δ 7.82, 7.55, 7.29, 7.26 (s each, 4H), 3.70 (s, 6H), 3.65 (t, J=6.2 Hz, 4H), 3.33 (Abq, Δv=47.0 Hz, J=9.1 Hz, 4H), 2.53 (t, J=6.2 Hz, 4H), 2.41 (s, 3H), 1.10 (s, 3H); $^{13}$C NMR (CDCl$_3$) δ 172.2, 143.1, 140.7, 129.6, 127.0, 73.7, 66.8, 58.9, 51.9, 34.9, 21.7, 18.2; HRMS (EI, MH$^+$) calcd for $C_{19}H_{30}NO_8S$: 432.16931. found: 432.16922.

Synthesis of Ligand 7

To a stirred solution of the ester (Intermediate 17) (3.61 g, 8.3 mmol) in methanol (50 mL) was added NH$_2$OTMs (3.52 g, 33.4 mmol) followed by KOH (0.94 g, 16.7 mmol). After 6 h at room temperature, the mixture was treated with 7.0 g of prewashed Amberlyst-15 and swirled for 1 h. The resin was filtered off and the filtrate was evaporated to give a gum. Recrystallization from $CH_2Cl_2$:ether (1:1) yielded Ligand 7, 2.46 g, (68%). IR (neat) 3233, 1633 cm$^{-1}$; $^1$H NMR (CDCl$_3$) δ 7.76, 7.68, 7.42, 7.39 (s each, 4H), 3.54 (m, 4H), 3.35 (s, 4H), 3.30 (Abq, Δv=22.6 Hz, J=10.0 Hz, 4H), 2.40 (s, 3H), 2.34 (t, J=5.8 Hz, 6H), 1.08 (s, 3H); $^{13}$C NMR (CDCl$_3$) δ 171.1, 145.0, 139.0, 130.2, 127.0, 73.5, 67.0, 59.5, 49.3, 21.0, 18.8; HRMS (EI, MH$^+$) calcd for $C_{17}H_{28}N_3O_8S$: 434.15983. found: 434.15970.

Example 8

Synthesis of Resin 1. Resin 1 was prepared by synthesizing the chelating functional group ($R^3$=a) of Ligand 1 on the surface of a polystyrene resin. The synthesis of Resin 1 is shown in Scheme 12. Macro-porous polystyrene beads (14, Amberlite XAD-4) were reacted with chlorosulfonic acid to give the polymeric sulfonyl chloride (15) (Emerson, D. W., Emerson, R. R., Joshi, S. C., Sorensen, E. M., Turek, J. E. *Polymer-bound sulfonylhydrazine functionality. Preparation, characterization, and reactions of copoly(styrene-divinylbenzenesulfonylhydrazine)*. J. Org. Chem. 1979, 44: 4634-4640; Hu, J.-B., Zhao, G., Ding, Z.-D. *Enantioselective reduction of ketones catalyzed by polymer-supported sulfonamide using NaBH4/Me3SiCl (or BF3\*OEt2) as reducing agent*. Angewandte Chemie, International Edition 2001, 40: 1109-1111). The procedures in Scheme 5 were used to prepare the methyl ester of the free amine form of ligand 1 (Intermediate 2). Addition of Intermediate 2 to the sulfonyl chloride form of the resin (15) gave the sulfonamide triester (Intermediate 18). The ester functional groups were converted to hydroxamic acids by reaction with O-trimethylsilyl hydroxylamine in methanol to give Resin 1. The successful conversion of the esters to hydroxamic acids was judged from the IR spectra. The number of ligand molecules on the surface of the resin was calculated from the S and N combustion analysis of the resin to be 0.3 mmoles ligand per gram of resin.

Scheme 12

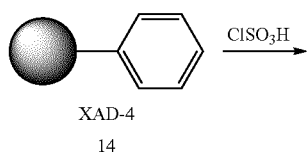

XAD-4
14

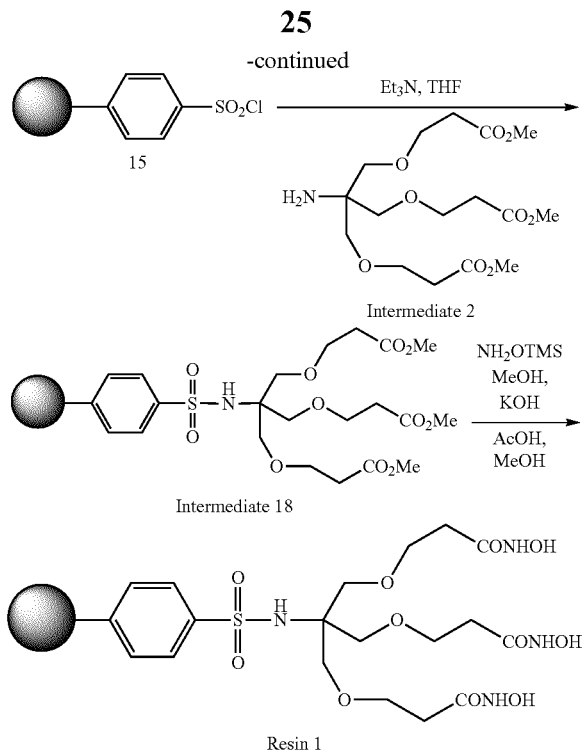

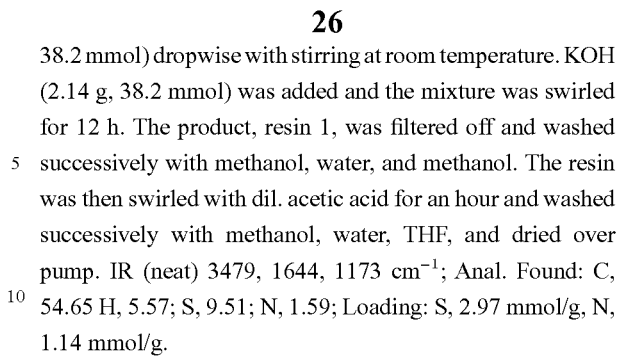

38.2 mmol) dropwise with stirring at room temperature. KOH (2.14 g, 38.2 mmol) was added and the mixture was swirled for 12 h. The product, resin 1, was filtered off and washed successively with methanol, water, and methanol. The resin was then swirled with dil. acetic acid for an hour and washed successively with methanol, water, THF, and dried over pump. IR (neat) 3479, 1644, 1173 cm$^{-1}$; Anal. Found: C, 54.65 H, 5.57; S, 9.51; N, 1.59; Loading: S, 2.97 mmol/g, N, 1.14 mmol/g.

Example 9

Synthesis of Resin 2. The overall synthesis of Resin 2 is shown in Scheme 13.

Scheme 13.

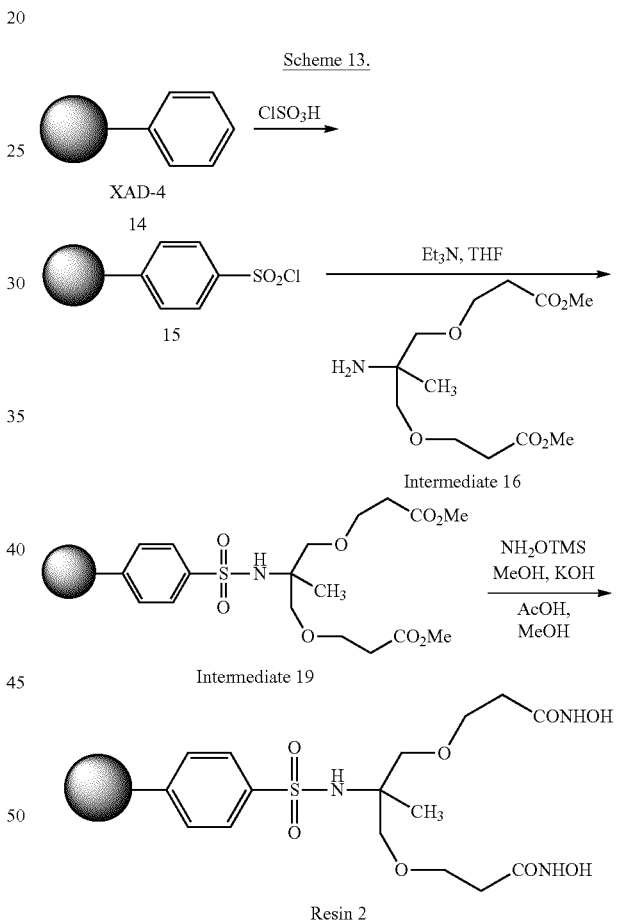

Synthesis of Sulfonyl Chloride Resin

To 35 g of macroporous styrene-divinylbenzene copolymer (20-60 mesh, avg. pore diameter: 40 Å, Amberlite XAD-4) in 100 mL of 1,2-dichloroethane was added 160 g (1.37 mol) of technical grade chlorosulfonic acid with occasional swirling. The mixture was kept at room temperature for 12 h. The product was filtered using a glass frit and was washed successively with two portions of dichloromethane (DCM), two portions of DCM-THF mixture, two portions of THF, and a final wash with DCM. The vacuum dried polymer was ready to use and was stored under argon at low temperature. IR (neat) 3521, 1369, 1171 cm$^{-1}$; Anal. Found: C, 57.17; H, 5.50; S, 10.23; Cl, 8.49; calculated loading S, 3.22 mmol/g, Cl, 2.39 mmol/g.

Synthesis of Intermediate 18

To polymeric sulfonyl chloride (15) (2.0 g, 5.0 mmol) in THF (50 mL) was added a solution of the tris ester of the free ligand (Intermediate 2) (7.58 g, 20.0 mmol) in THF (30 mL) followed by triethylamine (2.0 g, 20.0 mmol) and the mixture was swirled for four days at room temperature. The polymer was then filtered off and washed successively with THF, water, THF, DCM and dried in vacuo. IR (neat) 3494, 1732, 1169 cm$^{-1}$; Anal. Found: C, 58.96; H, 6.81; S, 8.22; N, 2.66; calculated loading: S, 2.57 mmol/g, N, 1.90 mmol/g.

Synthesis of Resin 1

To the resin-bound triester (Intermediate 18) (1.7 g, 4.25 mmol) in methanol (40 mL) was added NH$_2$OTMs (4.02 g, Synthesis of Intermediate 19. The synthesis of the chlorosulfonated polystyrene resin (15) is described in Scheme 12. To this polymeric sulfonyl chloride (5.2 g, 13.0 mmol) in THF (80 mL) was added a solution containing Intermediate 16 from Scheme 11, (14.4 g, 52.0 mmol) in THF (50 mL) followed by triethylamine (5.26 g, 52.0 mmol). The suspension was swirled for four days at room temperature. The product, Intermediate 19, was then filtered off and washed successively with THF, water, THF, DCM and dried over pump. IR (neat) 3492, 1735, 1170 cm$^{-1}$; Anal. Found: C, 60.28; H, 7.04; S, 8.42; N, 2.61; calculated loading: S, 2.63 mmol/g, N, 1.86 mmol/g.

Synthesis of Resin 2

To the resin-bound diester (Intermediate 19) (5.27 g, 13.17 mmol) in methanol (60 mL) was added NH$_2$OTMs (11.08 g, 105.3 mmol) dropwise with stirring at room temperature to give Resin 2. KOH (2.95 g, 52.6 mmol) was added and the mixture was swirled for 12 h. The resin was filtered off and washed successively with methanol, water, and methanol. The resin was then swirled with dilute acetic acid for an hour and washed successively with methanol, water, THF, and dried over pump. IR (neat) 3468, 1643, 1176 cm$^{-1}$; Anal. Found: C, 53.09; H, 5.59; S, 8.82; N, 1.95; Loading: S, 2.75 mmol/g, N, 1.39 mmol/g.

Example 10

Ligands Immobilized Via an Amide Linkage

The triester intermediate of each ligand containing a free amine group (R$^1$=H) is coupled to a resin bearing a carboxylic acid using a coupling reagent such as dicyclohexylcarbodiimide (DCC) or N-ethyl-N'-(3-dimethylaminopropyl) carbodiimide (EDC) with a tertiary amine base in THF solution. The esters are then converted to the hydroxamic acid as described above for the sulfonamide linked system. This process is described in Scheme 14 using Intermediate 2 as an example.

Scheme 14

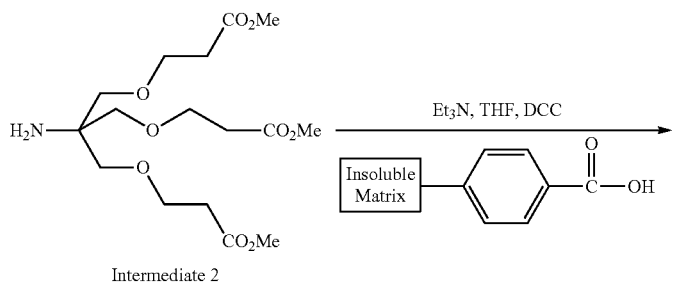

Intermediate 2

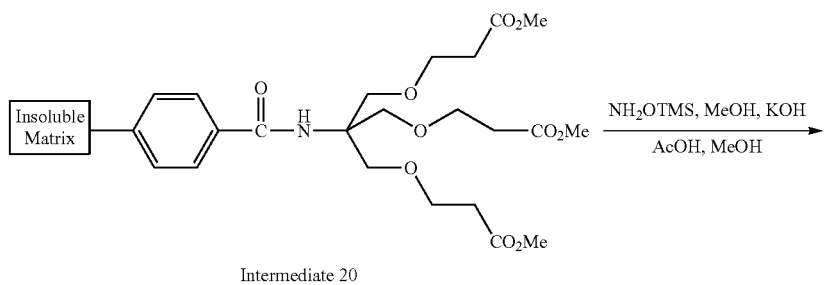

Intermediate 20

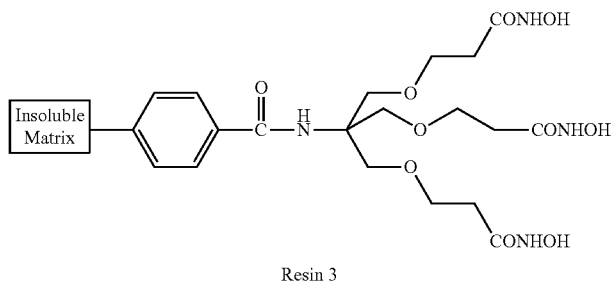

Resin 3

Example 11

Ligands Immobilized Via a Urea Linker

The amine of a triester intermediate is coupled to a resin bearing an amine via a urethane linkage using a reagent such as N,N-disuccinimidyl carbonate (16), carbonyl diimidazole or triphosgene with a tertiary amine base in THF solution. The esters are then converted to the hydroxamic acid as described above for the sulfonamide linked system. This process is shown in Scheme 15 using Intermediate 2 as an example.

Example 12

Extension of the Linker Group. In Paragraph [0032] and [0036] we showed three options for longer linkers that might be used to connect the chelating agent to the polymer resin. These linkers insert polyethylene glycol units between the aromatic ring of the resin and the amine group attached to the bridgehead carbon of the chelating agent.

The invention includes the use of three amine capped polyethylene glycol (PEG) based linkers, 3-oxa-1,5-diaminopen

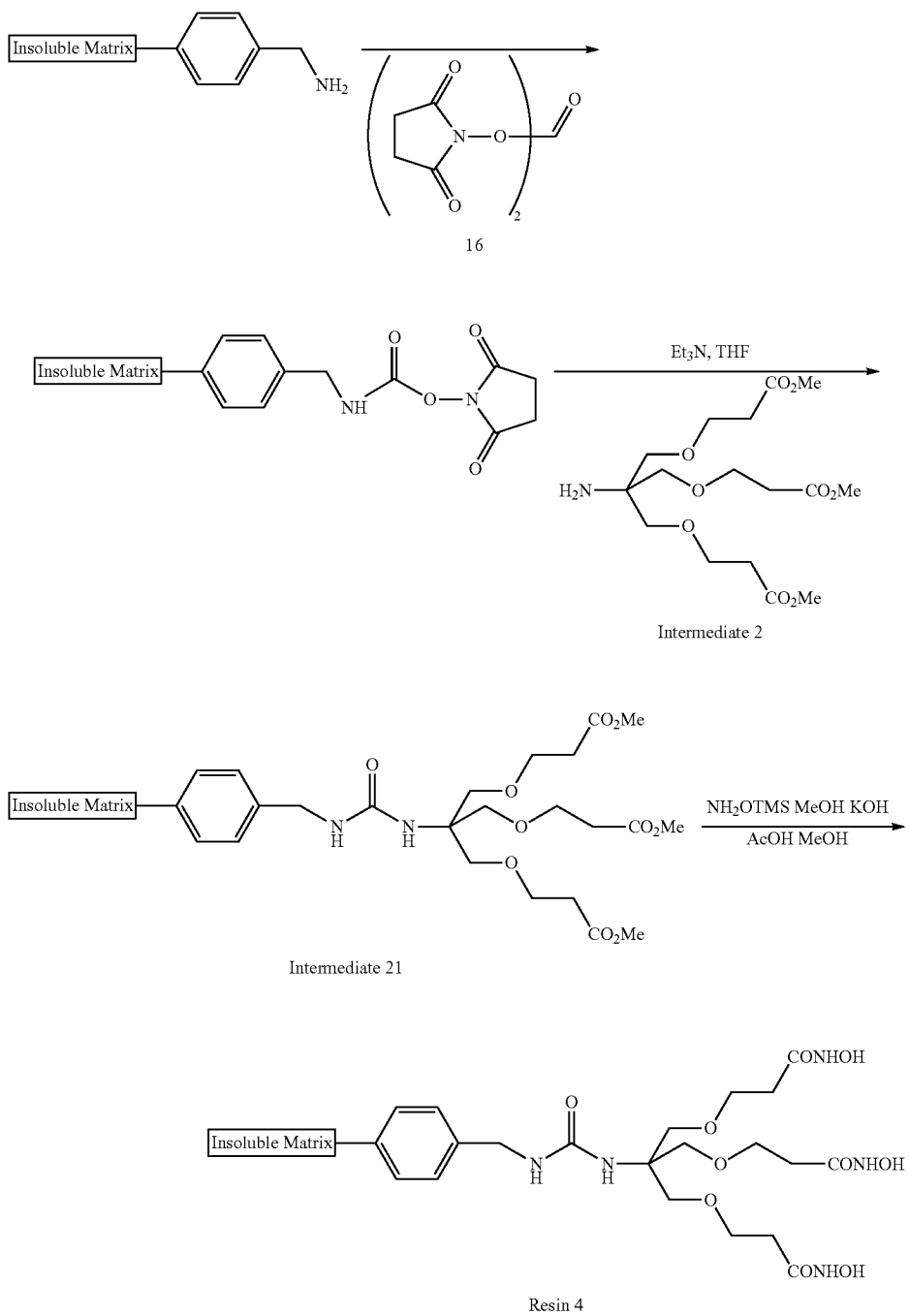

tane (17), 4,7,10-trioxa-1,13-tridecanediamine (18), and the 2-aminopropane capped polyethylene glycol with 10-12 PEG units (19), all of which are commercially available in bulk. A representative attachment scheme using Intermediate 2 and the 2 PEG unit diamine (17) is shown in Scheme 16, along with the structures of the two other PEG linkers (18,19).
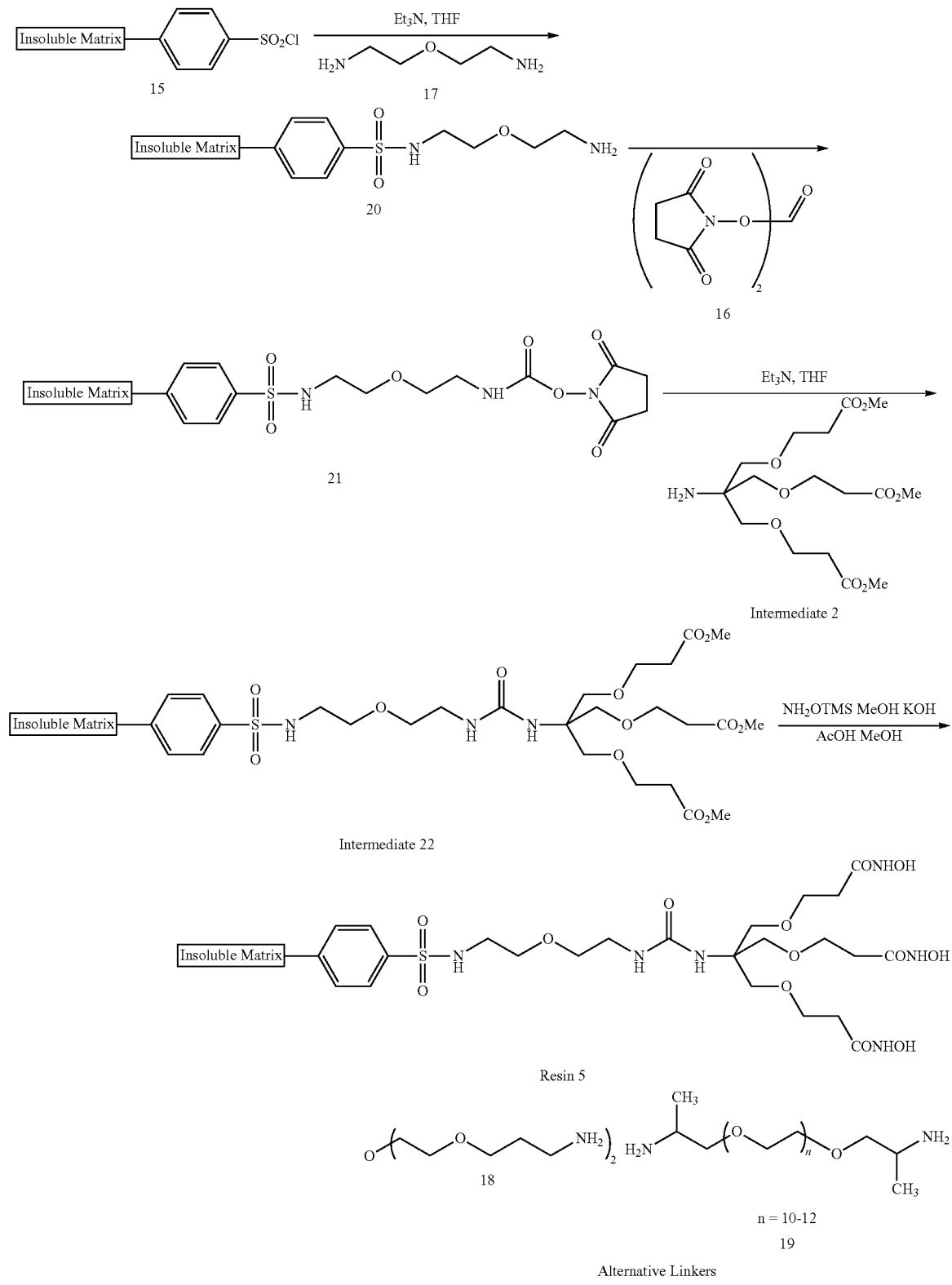

Each amine capped polyethylene glycol linker is attached to the activated resin (15) by using an excess of the diamine to ensure complete capping. The sulfonamide linked tether (20) is activated as the N-hydroxysuccinimide (NHS) with N,N'-disuccinimidyl carbonate (16) (Takeda, K., Y. Akagi, A. Saiki, T. Tsukahara, and H. Ogura, Studies on activating methods of functional groups. Part X. Convenient methods for syntheses of active carbamates, ureas, and nitroureas using N,N'-disuccinimido carbonate (DSC). Tetrahedron Letters, 1983, 24: 4569-4572.), followed by washing to remove the excess carbonate and the N-hydroxysuccinimide byproduct from the resin to produce (21). Reaction of the activated urethane with the amino-triester (Intermediate 2) provides the resin capped product Intermediate 22 which is expected to be stable to hydroxylamine and aqueous conditions. Final conversion to the trihydroxamate (Resin 5) is accomplished with O-trimethylsilyl hydroxylamine in methanol.

Example 13

Binding of Metal Ions by the Free Ligands

The acid dissociation constants for the trihydroxamate Ligand 1 and the dihydroxamate Ligand 7 have been determined by potentiometric titration of the free ligands in 0.1 M $KNO_3$ at 25° C. The overall ligand protonation constants for Ligand 1 are log $\beta_{011}$=10.26, log $\beta_{012}$=19.68, and log $\beta_{013}$=28.15. The overall ligand protonation constants for Ligand 7 are log $\beta_{011}$=9.80 and log $\beta_{012}$=18.49. These protonation constants have been used in the calculations of the metal chelate stability constants described below.

The binding of $Al^{3+}$, $Fe^{3+}$, and a series of divalent metal ions to Ligand 1 has been evaluated by potentiometric titration in 0.1 M $KNO_3$ at 25° C. For most of the metal ions, two complexes were detected. In one complex, all three of the hydroxamate groups were coordinated to the central metal one. The stability of these complexes is described by the overall binding constant $$\beta_{110} = \frac{[ML]}{[M][L]} \quad (3)$$

where L refers to the fully deprotonated, trianionic form of ligand 1, and charges on the species have been omitted for clarity.

The potentiometric analysis also detected a protonated metal chelate, designated as MHL. The position of the ligand-to-metal charge transfer band in the visible spectrum of the MHL complex of $Fe^{3+}$ indicated that in the MHL complexes, two of the hydroxamate groups are coordinated to the metal ion, while the third hydroxamate group is protonated and not bound to the metal ion. The stability of the MHL complexes is described by the overall binding constant $$\beta_{111} = \frac{[MHL]}{[M][L][H]} \quad (4)$$

The calculated binding constants for the complexes of Ligand 1 are listed in Table 2. The binding constant for $Al^{3+}$ is log $\beta_{110}$=21.44. Ligands with only two hydroxamates have binding constants of about log $\beta_{110}$~15 (Evers, A., Hancock, R. D., Martell, A. E., Motekaitis, R. J., *Metal ion recognition in ligands with negatively charged oxygen donor groups. Complexation of Fe(III), Ga(III), In(III), Al(III), and other highly charged metal ions*, Inorg. Chem. 1989, 28: 2189-2195). The larger value of log $\beta_{110}$ for Ligand 1 confirms that all three hydroxamate groups of the ligand are bound to the $Al^{3+}$.

TABLE 2

Binding constants for metal complexes of the trihydroxamate ligand, Ligand 1.

| | $Fe^{3+}$ | $Al^{3+}$ | $Cu^{2+}$ | $Ni^{2+}$ | $Zn^{2+}$ | $Mn^{2+}$ | $Ca^{2+}$ |
|---|---|---|---|---|---|---|---|
| Log $\beta_{111}$ | 27.60 | 26.27 | 23.61 | 19.10 | 19.13 | 17.06 | 13.34 |
| Log $\beta_{110}$ | 23.78 | 21.44 | — | 10.73 | 10.13 | 8.95 | 3.71 |

The data in Table 2 confirm that Ligand 1 shows very high selectivity for the binding of trivalent metal ions such as $Al^{3+}$ and $Fe^{3+}$ in preference to the binding of $Ca^{2+}$. This is a critical property, as it allows this ligand to bind trivalent metal ions in the presence of very high concentrations of $Ca^{2+}$.

Ligand 1 showed good selectivity for $Al^{3+}$ and $Fe^{3+}$ in comparison to the divalent transition metal ions $Cu^{2+}$, $Ni^{2+}$, $Zn^{2+}$, and $Mn^{2+}$. However, the binding affinities for these metal ions were still appreciable, especially for the binding of $Cu^{2+}$. Thus it is not claimed that the invention can remove $Al^{3+}$ and/or $Fe^{3+}$ from pharmaceutical solutions without also removing significant amounts of $Cu^{2+}$ and $Zn^{2+}$. The proposed process for reducing $Al^{3+}$ in total parenteral nutrition (TPN) solutions involves the removal of $Al^{3+}$ from the calcium gluconate and sodium phosphate component solutions, rather than treating the final TPN solution. Treating the final TPN solution with the invention is likely to remove a large percentage of the essential ions $Cu^{2+}$ and $Zn^{2+}$.

Example 14

Metal Binding by Ligand 7

The dihydroxamate Ligand 7 forms 1:1 complexes with all the metal ions studied in which both hydroxamate groups are coordinated to the metal ion. The stability of these complexes is characterized by the values of log $\beta_{110}$ shown in Table 3. The 1:1 complex of $Al^{3+}$, $Zn^{2+}$ and $Mn^{2+}$ hydrolyze to form the mixed-ligand hydroxo complexes ML(OH), characterized by the overall binding constant $$\beta_{11-1} = \frac{[ML(OH)][H]}{[M][L]} \quad (5)$$

Speciation calculations based on the stability constants in Table 3 indicated that the Al complex of Ligand 7 existed as a mixture of the ML and ML(OH) complexes over the pH range of 3 to 7. If an immobilized form of Ligand 7 (Resin 2) is used to remove $Al^{3+}$ from solutions within this pH range, the formation of the ML(OH) complex will stabilize the immobilized Al and facilitate removal of $Al^{3+}$ from the solution.

TABLE 3

Binding Constants for Metal Complexes of Ligand 7

| | $Al^{3+}$ | $Cu^{2+}$ | $Ni^{2+}$ | $Zn^{2+}$ | $Mn^{2+}$ |
|---|---|---|---|---|---|
| $\beta_{110}$ | 16.07 | 13.97 | 9.02 | 9.18 | 7.15 |
| $\beta_{11-1}$ | 11.06 | | | 0.35 | −0.1 |

Example 15

Binding of Al to Resin 1

The compounds and compositions of the present invention are useful in a method of removing a trivalent metal ion such as $Al^{3+}$ from an aqueous solution. This is performed by treating the aqueous solution with an effective amount of the compound or composition of the present invention. In the most preferred embodiment, the invention consists of a resin to which the chelating agent is attached by a covalent bond to form a chelating resin.

In one method of use, the resin is stirred in a solution. After the metal ions from the solution bind to the resin, the metal-depleted solution and the metal-laden resin are separated by filtration or decantation.

In a second method of use, the resin is packed in a column, and the metal-containing solution is passed through the column. The metal ions are retained on the column, while the metal-depleted solution exits from the outlet of the column.

In one possible application, the invention would be used to reduce the amount of $Al^{3+}$ contained in total parenteral nutrition solutions, particularly for TPN solutions given to neonates. The binding constants shown in Tables 1 and 2 indicate that treatment of the final TPN solution with the invention is likely to remove essential metal ions such as $Fe^{3+}$, $Cu^{2+}$ and $Zn^{2+}$ in addition to $Al^{3+}$. Thus the strongly preferred process is to use the invention to remove the $Al^{3+}$ from small volume parenteral (SVP) solutions that are used in the preparation of TPN solutions.

The primary "culprit" SVP solutions, which are contaminated with aluminum thereby contributing aluminum to the final TPN admixture and therefore to the patient, are calcium gluconate and sodium phosphate (Driscoll, M. and D. F. Driscoll, Am. J. Health-Syst. Pharm. 2005, 62: 312-315). It should be appreciated that removal of $Al^{3+}$ from these solutions is difficult because the anions of these salts, gluconate and phosphate, respectively, are themselves strong Al-binding agents (R. J. Motekaitis and A. E. Martell, Inorg. Chem. 1984, 23: 18-23; K. Atkari, T. Kiss, R. Bertani, and R. B. Martin, Inorg. Chem. 1996, 35: 7089-7094). Thus the invention must compete against high concentrations of these anions in order to remove $Al^{3+}$ from the solution.

In one possible application, the compositions of the present invention are loaded into a flow-through filter device such as illustrated in FIGS. 8a-8d and described in greater detail below. As the SVP solution flows through the device, the aluminum is extracted from the solution. The device is provided in-line between the container of the SVP culprit solution and the TPN bag being prepared by the automated TPN compounder. The device has on its outlet side a membrane filter with a pore size small enough to sterilize the solution by filtration, retain the resin in the device and block release of large particles from the device. A screen on the inlet side contains the resin. Leur lock or similar connectors on the inlet and outlet sides enable easy connection to standard i.v. fluid administration sets.

In another medical application, the compounds and compositions of the present invention are utilized to ensure that aluminum is not inadvertently included in the dialysis solution used in peritoneal dialysis or hemodialysis. Another example is home peritoneal dialysis, where tap water is used to prepare the dialysate. If the tap water contains significant aluminum, which might have been introduced during the water treatment process, or might enter in the raw water, and which is not adequately removed during the water treatment process, the aluminum could enter the patient. In addition the compounds and compositions of the present invention could be used on a bulk scale in industry to remove aluminum from solutions such as the solutions that go into SVP containers or any material or process that is contaminated with aluminum, such as the guanine nucleotide-binding regulatory component (G/F) of adenylate cyclase, with which aluminum binds to activate adenylate cyclase. The following experimental data support the utility of the claimed compounds and compositions.

To demonstrate the ability of Resin 1 to bind Al, 50 mg of the resin was suspended in 100 ml of a buffered (0.10 M 4-morpholineethanesulfonic acid) aqueous solution at pH 5, and 25 mcg Al was added, as an acidic solution of aluminum chloride. The free $Al^{3+}$ concentration in the sample solution was measured as a function of time by ETAAS. The results are shown in FIG. 2. The 50 mg of resin removed 94% of the $Al^{3+}$ from the solution after 94 hours and 97.4% of the $Al^{3+}$ from the solution after 287 hours (see FIG. 2 and Table 5). The removal of the $Al^{3+}$ followed first order kinetics, with a half-life of 10.5 hrs.

The $Al^{3+}$ removal experiment was repeated by adding 25 mcg of $Al^{3+}$ and 50 mg of Resin 1 to a smaller volume of only 5 ml of MES buffer at pH 5. The results are shown in FIG. 2. Under these conditions, 98% of the $Al^{3+}$ was removed from the solution within 12 hr and 99.9% after 24 hours.

The removal of $Al^{3+}$ from MES buffer was also followed by a spectrophotometric assay in which the weaker chelating agent 7-iodo-8-hydroxyquinoline-5-sulfonic acid (ferron) was used as an indicator for free $Al^{3+}$. The data are shown in FIG. 3. The starting solution contains a 1:1 ratio of 150 microMolar $Al^{3+}$ and ferron in a total volume of 3.0 ml, and the initial spectrum shows the peak at 360 nm indicative of the Al-ferron complex. A total of 25 mg of Resin 1 was added to the solution, and the removal of $Al^{3+}$ from the solution was monitored by the loss of the absorbance of the Al-ferron complex at 360 nm and the corresponding increase in the absorbance of free ferron at 440 nm. Based on a comparison to the final absorbance to that of a standard solution of free ferron, it is estimated that the resin removed approximately 80% of the $Al^{3+}$. The rate of Al removal corresponds to a half-life of approximately 90 min. The smaller percentage of Al removed reflected the competition for $Al^{3+}$ from the ferron. These data were used to estimate an equilibrium constant for the binding of $Al^{3+}$ to the Resin 1 as described below.

To determine the capacity of Resin 1 to bind Al, sequential aliquots of 100 mcg of $Al^{3+}$ were added at 8 hr intervals to 50 mg of the resin suspended in 100 ml of MES buffer at pH 5. The total amount of Al added to the solution was 6,000 ng/ml. The concentration of free Al remaining in the solution was followed by ETAAS. The results are shown in FIG. 4. Because of the slow rate of Al removal in dilute solutions, the concentration of $Al^{3+}$ accumulates to a total of approximately 4,000 ng/ml after the addition of the final aliquot of $Al^{3+}$. However, after 200 hrs the resin removed about 85% of the added $Al^{3+}$, reducing the free Al concentration to about 1,000 ng/ml. This indicates that the binding capacity of Resin 1 is at least 10,000 mcg $Al^{3+}$ per gram of resin.

The binding affinity of Resin 1 has been evaluated from four different types of experiments and the results are summarized in Table 5. Binding constants for the immobilized ligand were calculated using the speciation program HySS. A multicomponent equilibrium model was constructed for each reaction solution, in which the binding constant of Resin 1 was the only unknown binding constant. This constant was then adjusted manually until the HySS speciation model results matched the experimentally determined value for the percentage of Al bound to the resin. In all the calculations of the binding constants for the resin, the protonation constants for the immobilized ligand are assumed to be the same as those of the free ligand so that the resulting equilibrium constant can be expressed as a value of log $\beta_{110}$, rather than a pH-dependent effective binding constant.

The binding affinity of Resin 1 was determined from the final Al concentrations shown in FIG. 2 for the removal of $Al^{3+}$ from MES buffer. In these calculations, the only competitive binding agent was hydroxide ion. The calculations used hydrolysis constants for the $Al^{3+}$ for 0.1 M ionic strength taken from Mesmer and Baes (The Hydrolysis of Cation, Wiley, New York, 1976). The values of $\beta_{110}$ for the immobilized ligand of Resin 1 are listed in Table 5.

The aluminum binding constant for Resin 1 has been calculated from the spectrophotometric data shown in FIG. 3. In addition to $Al^{3+}$ hydrolysis constants, these calculations included the Al binding constants of ferron from Martell and Smith (Critical Stability Constants, Vol 3, Plenum, N.Y., 1979). The binding constant for Resin 1 is listed in Table 5.

The Al binding constant for Resin 1 has been determined by competition against the well-known hexadentate chelating agent 1,10-diaza-4,7-dioxadecane-1,1,10,10-tetraacetic acid (EGTA). A known amount of Resin 1 was allowed to equilibrate in a pH 5.7 solution containing both EGTA and $Al^{3+}$. After equilibration, the concentration of Al bound in the solution to EGTA was determined by ETAAS. Protonation constants and the Al-binding constant for EGTA were taken from Martell and Smith (Critical Stability Constants, vol 1, Plenum, N.Y., 1974). The binding constant for Resin 1 is listed in Table 5.

Aluminum binding constants for the Resin 1 were also measured by competition against gluconic acid. A 50 mg aliquot of the resin was added to 1 ml of a commercial solution of 0.23 M Ca(gluconate)$_2$. Analysis by ETAAS showed that the untreated solution contained 115 mcMolar $Al^{3+}$ as a contaminant. No other Al was added to the solution. Resin 1 removed approximately 10% of the Al from this solution. Based on the known binding constants for Al-gluconate, HySS was used to calculate the binding constant for the immobilized ligand on Resin 1. The binding constant for Resin 1 is listed in Table 5.

Competition experiments versus gluconate were repeated using samples in which the commercial Ca(gluconate)$_2$ solution was diluted with pH 5 MES buffer. These solutions contained gluconate concentrations of 0.215 M, 0.1 M, and 0.046 M gluconic acid. The results are listed in Table 5.

To determine the ability of Resin 1 to bind Al at ratios of mg resin per ml of Ca(gluconate) that more closely model conditions one expects in a filtration device, another competition experiment versus gluconate was conducted using samples in which 250 mg of Resin 1 was added to 0.50 ml of the commercial Ca(gluconate)$_2$ solution. The initial Al concentration was 9130 ng/ml. The concentration of free Al remaining in the solution was followed by ETAAS. The results are shown in FIG. 5.

TABLE 5

Summary of Experiments to Calculate the Al binding constant ($\beta_{110}$) for Resin 1

| Solution | Total Volume (ml) | pH | mg resin | Total Al (microMolar) | % Al removed | Log $\beta_{110}$ |
|---|---|---|---|---|---|---|
| 0.1M MES | 100 | 5.0 | 50 | 9.26 | 97.4 | 18.9 |
| 0.1M MES | 5 | 5.0 | 50 | 185 | 99.9 | 18.2 |

TABLE 5-continued

Summary of Experiments to Calculate the Al binding constant ($\beta_{110}$) for Resin 1

| Solution | Total Volume (ml) | pH | mg resin | Total Al (microMolar) | % Al removed | Log $\beta_{110}$ |
|---|---|---|---|---|---|---|
| 0.15 mM ferron | 3 | 5 | 25 | 150 | 78 | 19.2 |
| 10 mM EGTA | 1 | 5.7 | 50 | 14.9 | 58 | 18.8 |
| 0.23M Ca(glu)$_2$ | 1 | 5.3 | 50 | 115 | 10 | 18.5 |
| 0.108M Ca(glu)$_2$ | 1 | 5.2 | 50 | 53.8 | 18 | 18.5 |
| 0.05M Ca(glu)$_2$ | 1 | 5.4 | 50 | 25.0 | 44 | 18.7 |
| 0.023M Ca(glu)$_2$ | 1 | 5.3 | 50 | 11.5 | 72 | 18.9 |
| 0.23M Ca(glu)$_2$ | 0.5 | 4.3 | 250 | 338 | 40 | 19.0 |

The overall average binding constant for the immobilized ligand of Resin 1 from the data in Table 5 is log $\beta_{110}$=18.7±0.3. This value is about 2.7 log units less than the binding constant for free Ligand 1. Unfavorable steric interactions with the resin may be a factor, particularly when large, bulky ligands are bonded to the resin (M. Feng, L. van der Does, and A. Bantjes, J. Appl. Polymer Sci., 1995, 56: 1231-1237). The invention includes resins with longer groups linking the ligand to the polymer. It is anticipated this elongation of the linker will result in better agreement between the binding constants of the free and immobilized ligands.

It is significant that the binding constants calculated from competition with the gluconate solutions are in good agreement with the other values in Table 5. This confirms that the presence of high concentrations of $Ca^{2+}$ in the gluconate solutions has essentially no impact on the ability of the resin to remove Al from gluconate solutions.

EXPANDED DETAILED DESCRIPTION OF THE PREFERRED EMBODIMENTS OF THE INVENTION

The present invention relates to generally novel chelating agents having general formula of

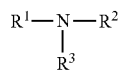

wherein $R^1$=hydrogen, sulfonamide, carbamoyl, carbamate, carboxamide, aryl or alkyl, $R^2$=hydrogen, methyl, ethyl, n-propyl, isopropyl or similar alkyl substituent and R³=

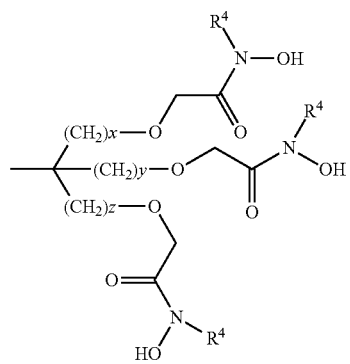
a)

wherein x, y, and z vary independently from 1 to 4, X=CH$_2$ and O, and R⁴=hydrogen, methyl, ethyl, n-propyl, isopropyl or similar alkyl substituent.

[Note: when x=y=z=1, this is the TRIS platform]

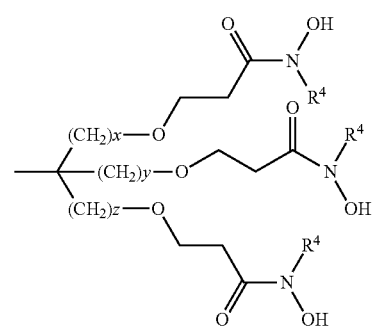
b)

wherein x, y, and z vary independently from 1 to 4, and R⁴=hydrogen, methyl, ethyl, n-propyl, isopropyl or similar alkyl substituent.

[Note: when x=y=z=1, this is the TRIS platform]

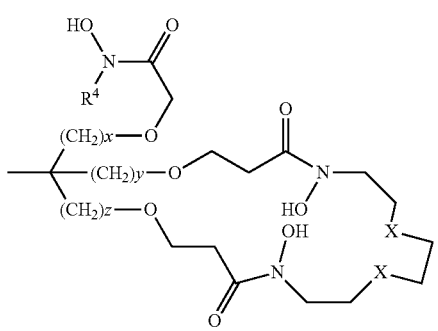
c)

wherein x and y vary independently from 1 to 4, X=CH$_2$ and O, and R⁴=hydrogen, methyl, ethyl, n-propyl, isopropyl or similar alkyl substituent.

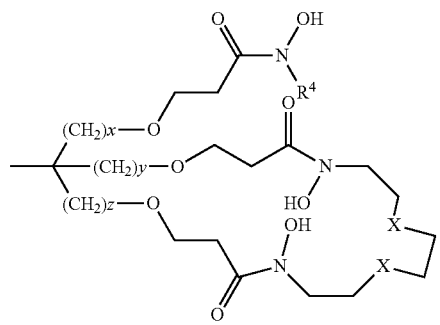
d)

wherein x and y vary independently from 1 to 4, X=CH$_2$ and O, and R⁴=hydrogen, methyl, ethyl, n-propyl, isopropyl or similar alkyl substituent.

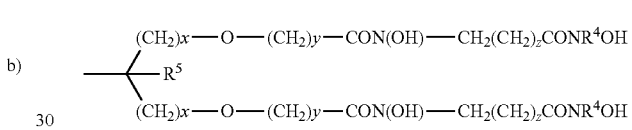
e)

wherein x varies from 1-4, y varies from 1-2, and z varies independently from 2 to 8, R⁴=hydrogen, methyl, ethyl, n-propyl, isopropyl or similar alkyl substituent, and R⁵=hydrogen, methyl, ethyl, n-propyl, isopropyl or similar alkyl substituent.

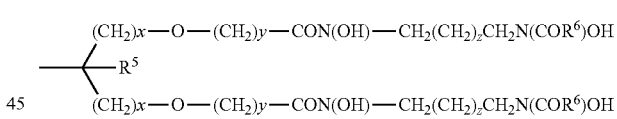
f)

wherein x varies from 1-4, y varies from 1-2, and z varies independently from 2 to 8, R⁵=hydrogen, methyl, ethyl, n-propyl, isopropyl or similar alkyl substituent, and R⁶=hydrogen, methyl, ethyl, n-propyl, isopropyl or similar alkyl substituent, or Ph or similar aryl substituent The present invention also includes generally novel tripodal triesters as precursors or useful intermediates to chelating ligands having general formula of

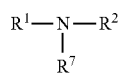

R¹ wherein R=hydrogen, sulfonamide, carbamoyl, carboxamide or benzyl, R²=hydrogen, methyl, ethyl, n-propyl, isopropyl or similar alkyl substituent and R⁷= g)

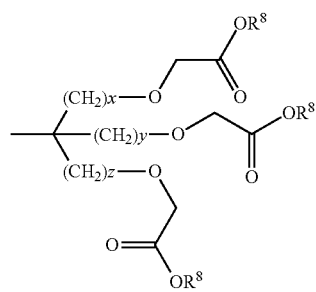

wherein x, y, and z vary independently from 1 to 4, X=CH₂ and O, and R⁸=hydrogen, methyl, ethyl, n-propyl, isopropyl or similar alkyl substituent and Ph or similar aryl substituent.

h)

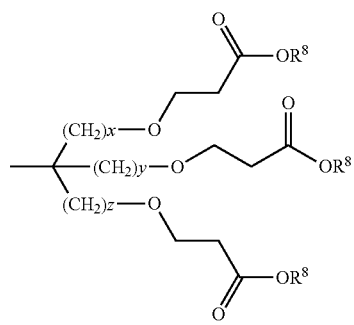

wherein x, y, and z vary independently from 1 to 4, X=CH₂ and O, and R⁸=hydrogen, methyl, ethyl, n-propyl, isopropyl or similar alkyl substituent and Ph or similar aryl substituent.

The novel compounds of the present invention are particularly useful as chelators or chelating agents. One preferred use of the free ligands would be in vivo chelation therapy to remove metal ions such as $Fe^{3+}$ and $Al^{3+}$ from the body.

The compounds include an amine functional group that allows the ligands to be easily linked to an insoluble matrix via a sulfonamide linkage, an amine linkage, an amide linkage, or a urea linkage to provide immobilized, tethered chelators. Typically, the insoluble matrix comprises a resin support. The resin support may take the form of a macro-porous polystyrene such as commercially available under the trademark XAD-4 sold by Rohm and Haas. Other polymer resins useful in the present invention include but are not limited to, polyacrylate, sepharose and silica gel.

The overall process of adding a chelating compound of the present invention to a polystyrene resin via a sulfonamide bond, where NR²H-Ligand in this and subsequent schemes refers to the free amine form ($R^1$=H; $R^2$=hydrogen, methyl, ethyl, n-propyl or isopropyl) of any of the free ligands represented by R³=a through f is shown in scheme 17.

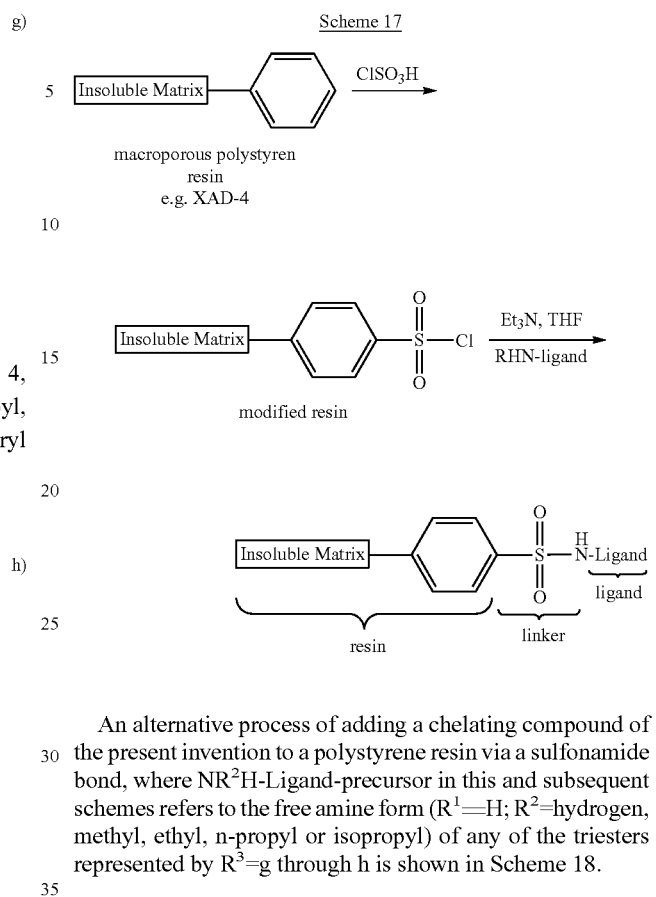

An alternative process of adding a chelating compound of the present invention to a polystyrene resin via a sulfonamide bond, where NR²H-Ligand-precursor in this and subsequent schemes refers to the free amine form ($R^1$=H; $R^2$=hydrogen, methyl, ethyl, n-propyl or isopropyl) of any of the triesters represented by R³=g through h is shown in Scheme 18.

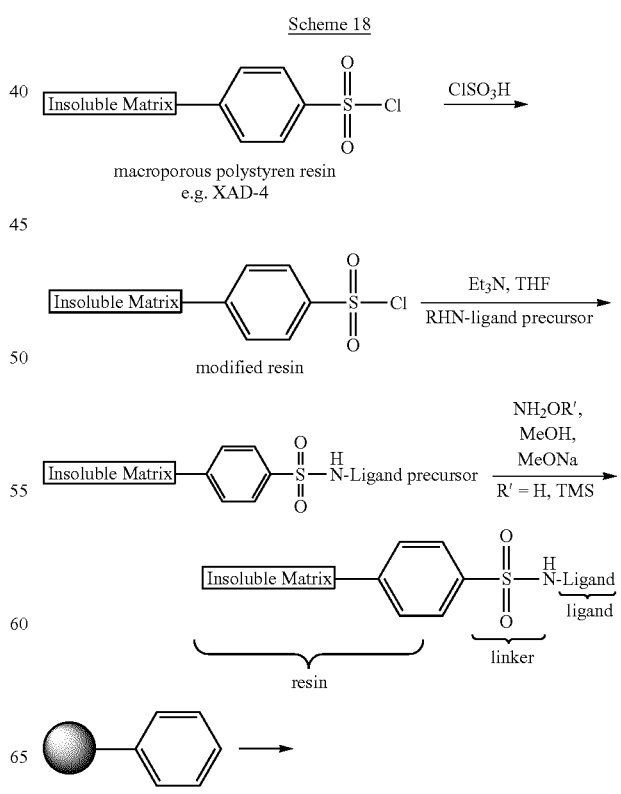

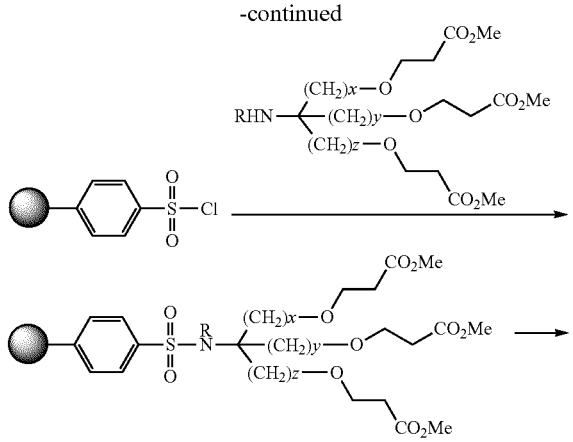
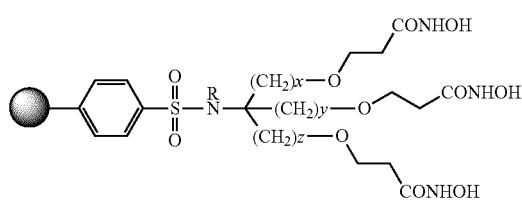
The overall process of adding a chelating compound of the present invention to a resin support by means of a urea linkage is shown in Scheme 19.
Scheme 19
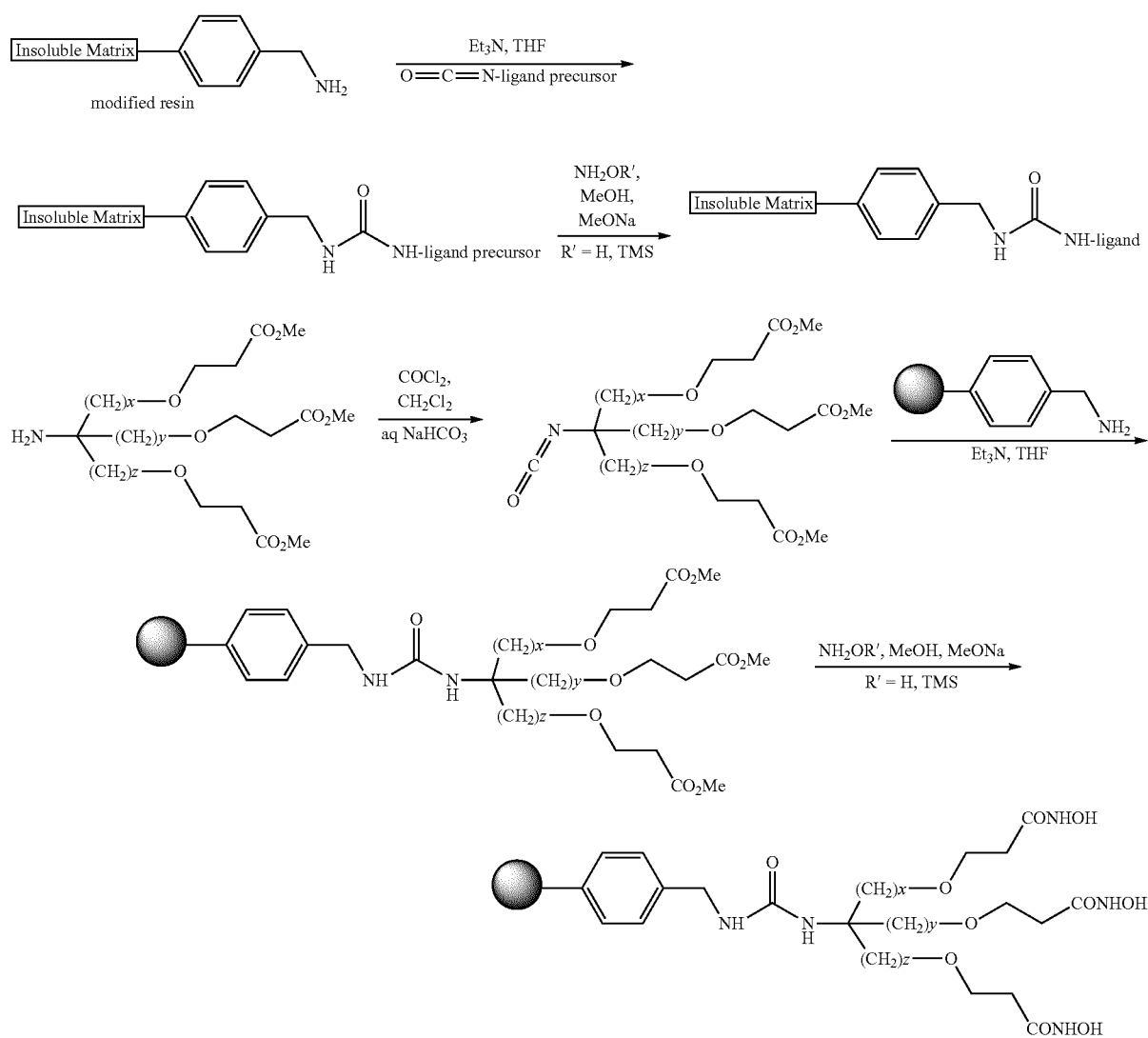
Insoluble Matrix = ⬤

An alternative process of adding a chelating compound of the present invention to a resin support by means of a urea linkage is shown in Scheme 20.
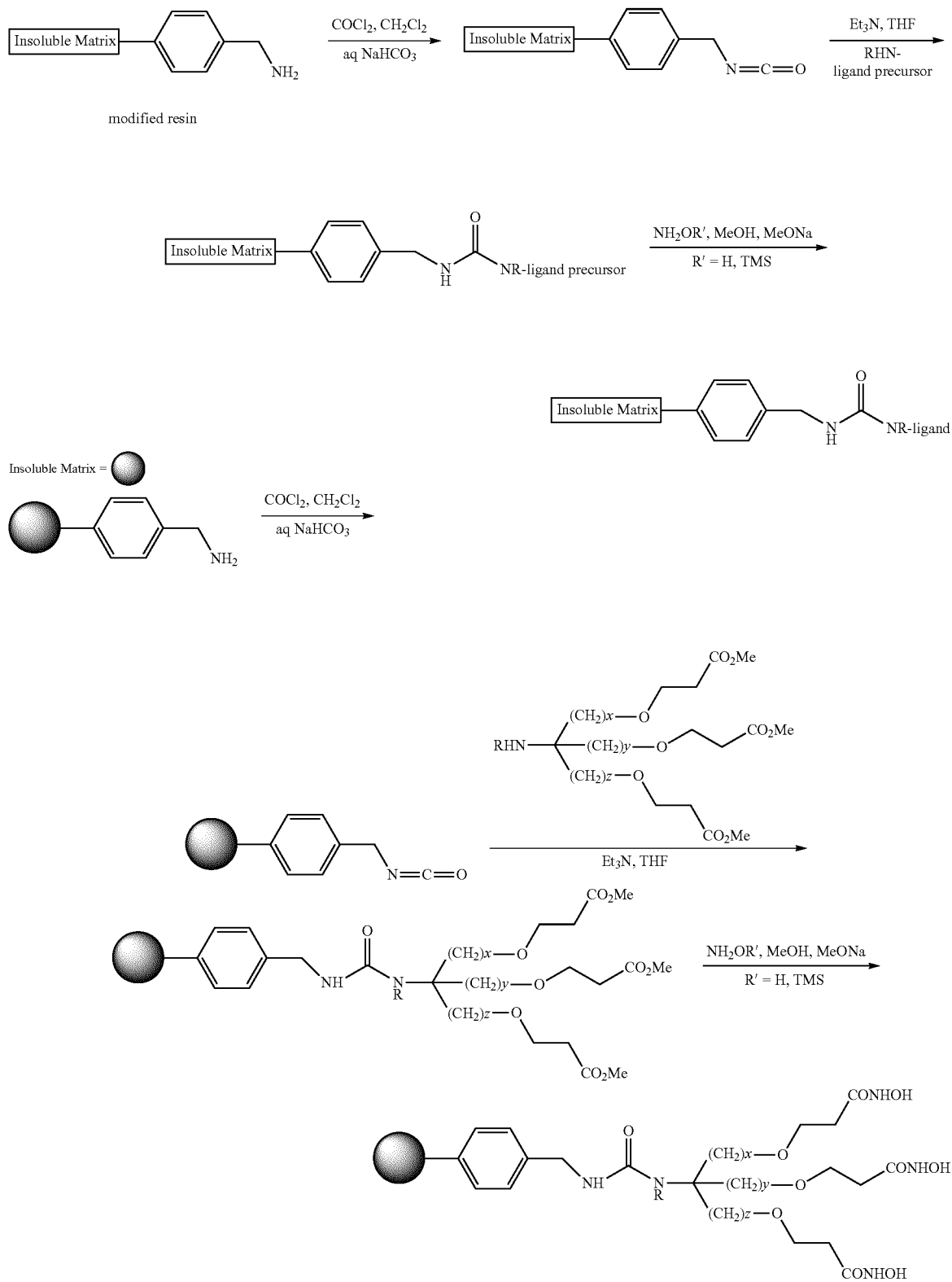
Scheme 20

The overall process of adding a chelating compound of the present invention to a resin support by means of an amine linkage is shown in Scheme 21.
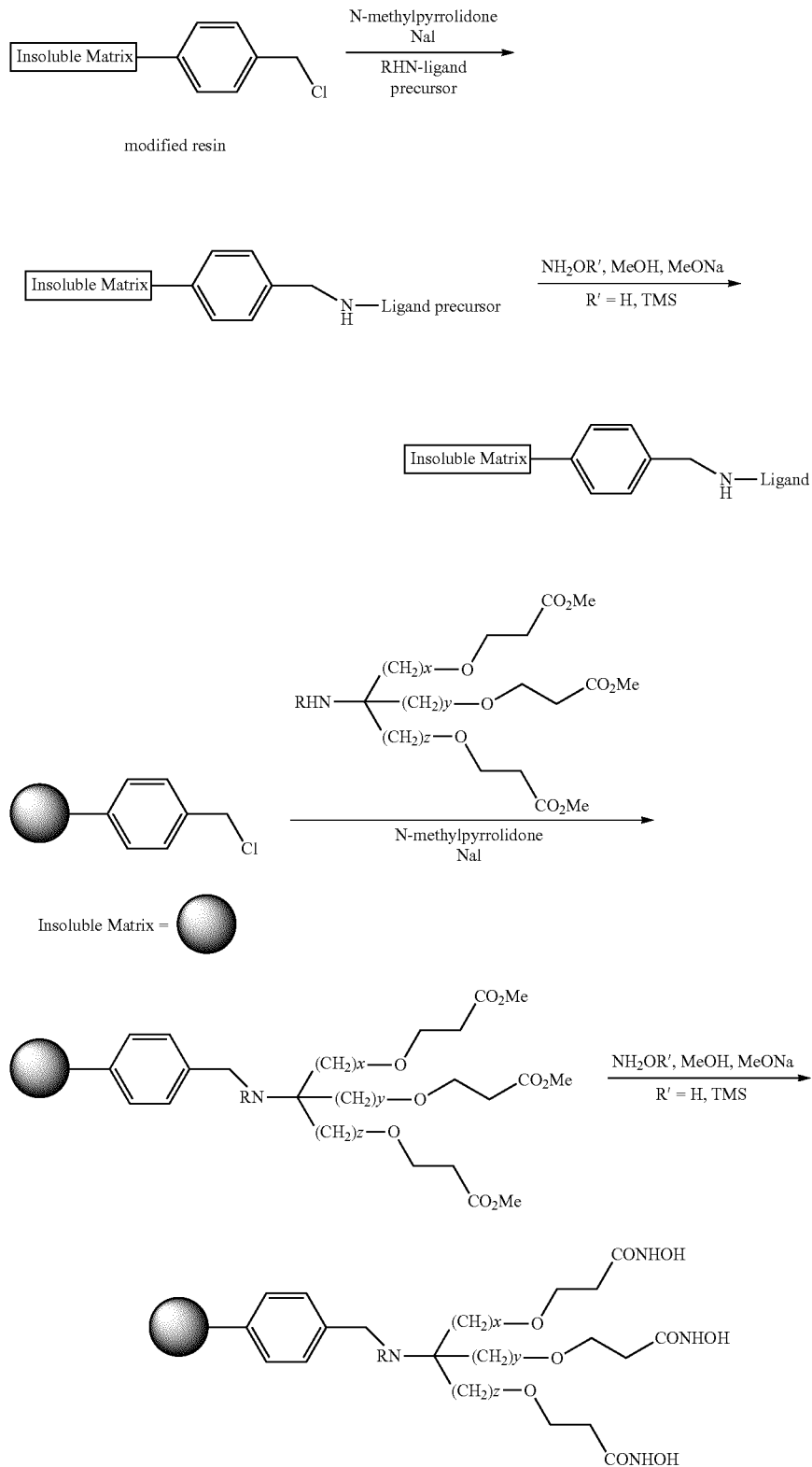

The overall process of adding a chelating compound of the present invention to a resin support by means of an amide linkage is shown in Scheme 22.

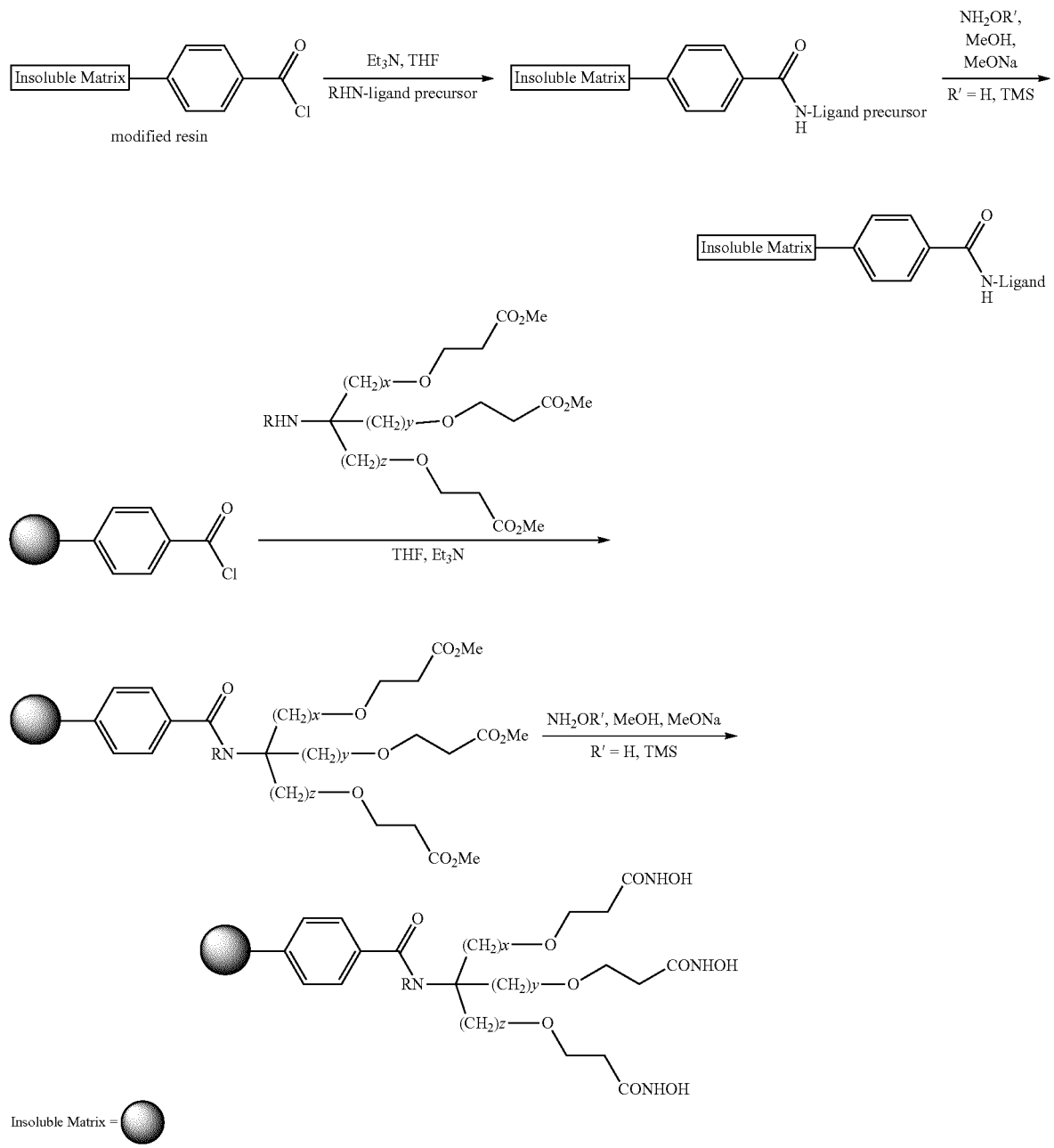

For certain applications it may be desirable to elongate the linker by adding polyethylene glycol units between the resin support and the ligand in order to increase the rate of metal binding to the resin-bound ligand. These elongated linkers are added using commercially available amine capped polyethylene glycols of variable length, with the use of a urea functional group to covalently bind the ligand and linker moieties.

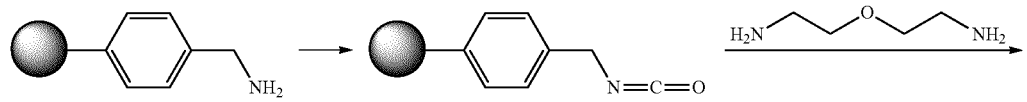

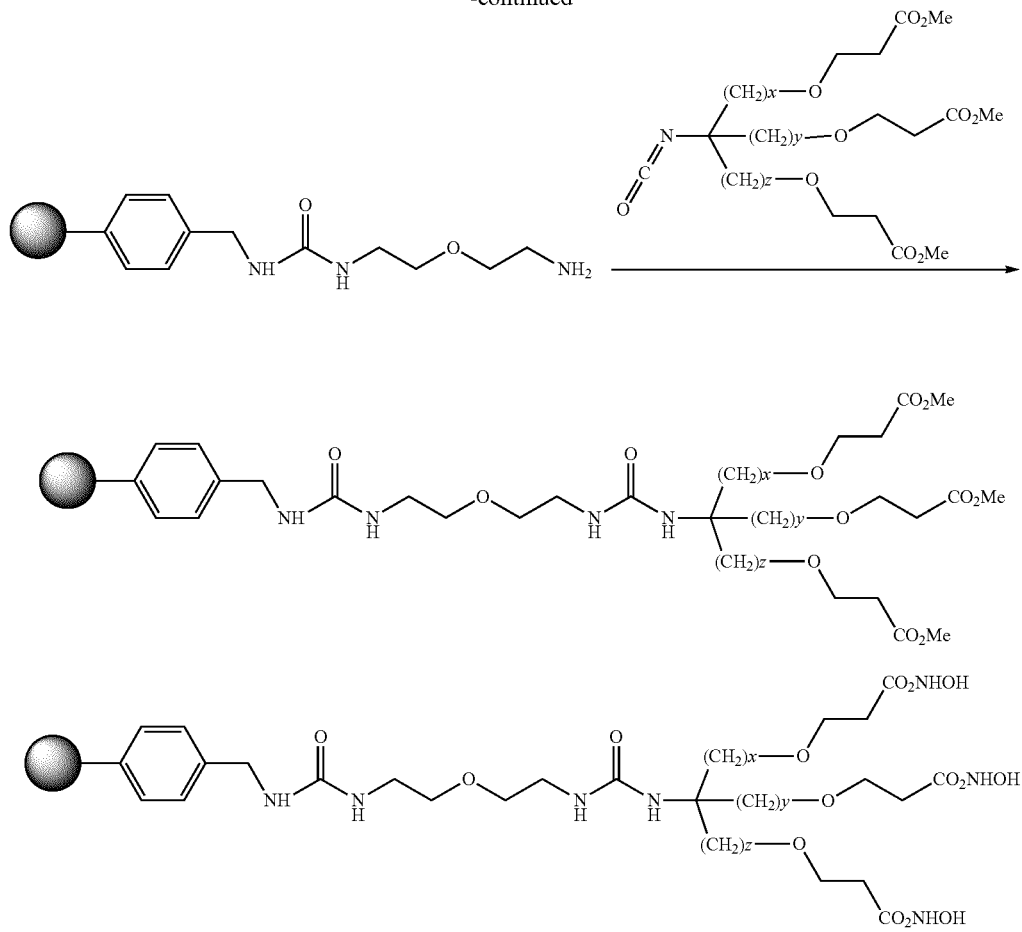

Insoluble Matrix = ⬤

Other commercially available amine-capped polyethyleneglycols include the compound

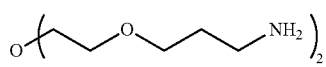

which gives chelating resins with the structures shown below

The immobilized, tethered chelators of the present invention comprise the chelating compounds identified above bound to a resin support through an appropriate linkage. The immobilized, tethered chelators of the present invention may be generally described as having the following formula:

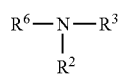

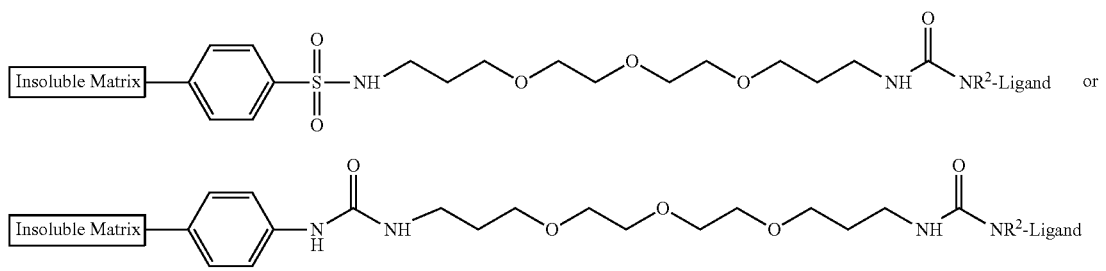

wherein R⁶=

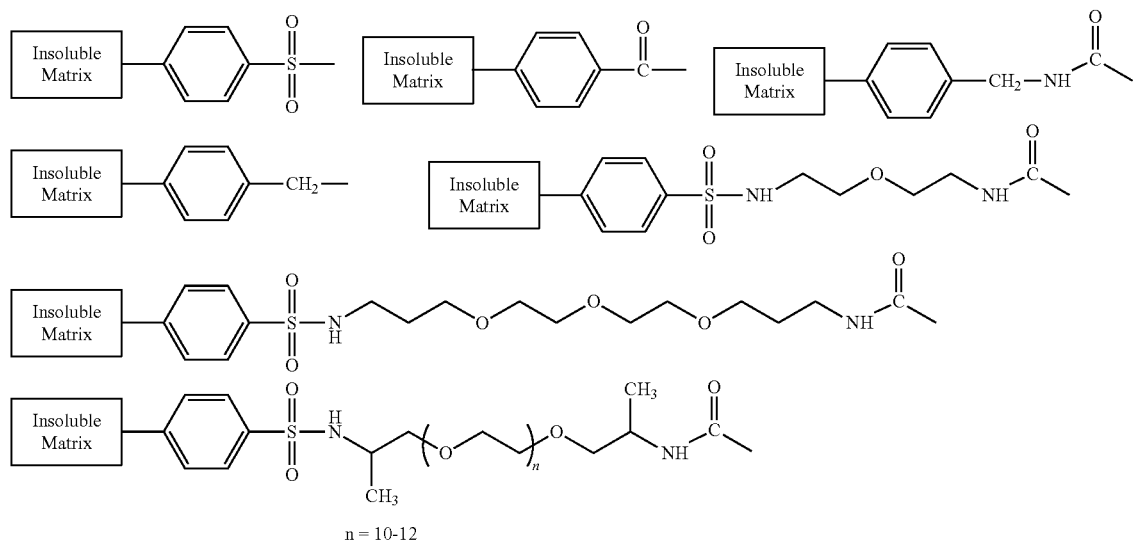

n = 10-12

$R^2$=hydrogen, methyl, ethyl; n-propyl or isopropyl and
$R^3$= a)

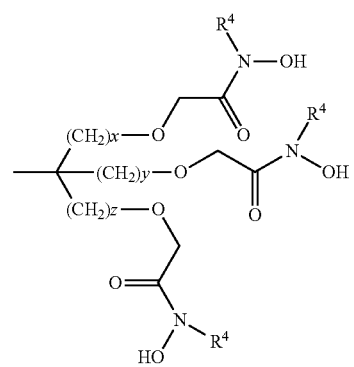

wherein x, y, and z vary independently from 1 to 4, X=CH₂ and O, and $R^4$=hydrogen, methyl, ethyl, n-propyl, isopropyl or similar alkyl substituent.

b)

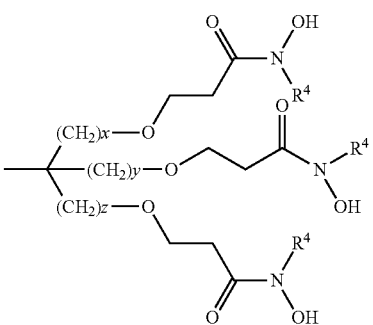

wherein x, y, and z vary independently from 1 to 4, and $R^4$=hydrogen, methyl, ethyl, n-propyl, isopropyl or similar alkyl substituent.

c)

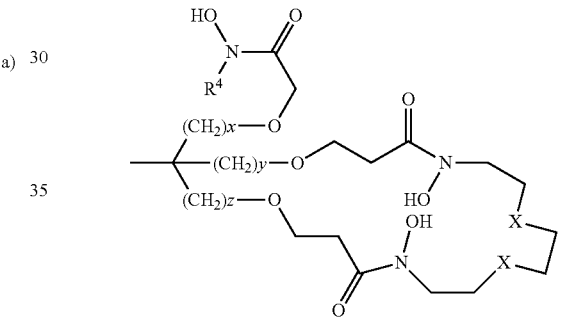

wherein x and y vary independently from 1 to 4, X=CH₂ and O, and $R^4$=hydrogen, methyl, ethyl, n-propyl, isopropyl or similar alkyl substituent.

d)

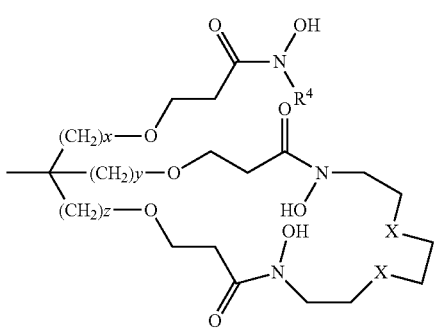

wherein x and y vary independently from 1 to 4, X=CH₂ and O, and $R^4$=hydrogen, methyl, ethyl, n-propyl, isopropyl or similar alkyl substituent.

e)

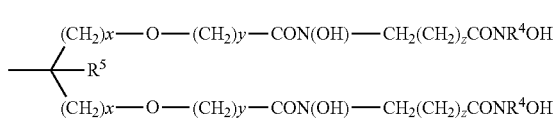

wherein x varies from 1-4, y varies from 1-2, and z varies independently from 2 to 8, $R^4$=hydrogen, methyl, ethyl, n-propyl, isopropyl or similar alkyl substituent, and $R^5$=hydrogen, methyl, ethyl, n-propyl, isopropyl or similar alkyl substituent.

Example 16

General Synthesis of Tripodal Ligands

A general approach to the amino triol scaffolds (24a-d to 27a-d) employs the chemistry of nitroalkanes. Starting with 2-nitroethanol (23a), 3-nitropropanol (23b), 4-nitrobutanol (23c) or 5-nitropentanol (23d), two identical alkenol chains can be added with 1 carbon atom (24a-d), 2 carbon atoms (25a-d), 3 carbon atoms (26a-d), or 4 carbon atoms (27a-d). In all cases, reduction of the nitro group with hydrogen over T1 Raney nickel will yield the amino compounds. Protection of the nitroalkenols (23a-d) with a TBS group (series B) will yield amino triols with one chain differentiated for further reaction.

Scheme 24

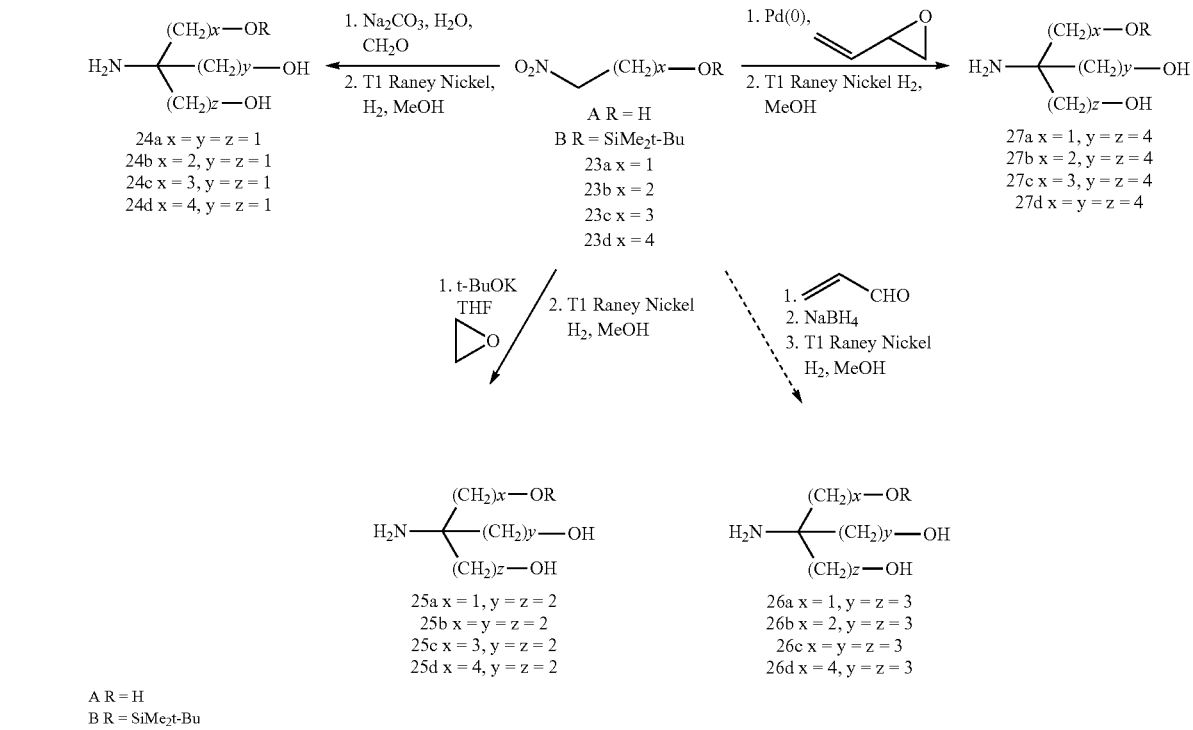

f)

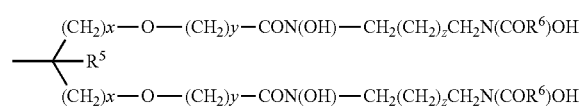

wherein x varies from 1-4, y varies from 1-2, and z varies independently from 2 to 8, $R^5$=hydrogen, methyl, ethyl, n-propyl, isopropyl or similar alkyl substituent, and $R^6$=hydrogen, methyl, ethyl, n-propyl, isopropyl or similar alkyl substituent, or Ph or similar aryl substituent The tripodal ligands with different length side arms can be prepared by the reactions of aminomethyl triol scaffolds (24-27)] with acrylonitrile then HCl/MeOH (28-31), or ethyl diazoacetate (36-39). The resulting esters (28-31 and 36-39) are converted to the hydroxamates (32-35 and 40-43) with hydroxylamine or TMSONH$_2$.

Scheme 25

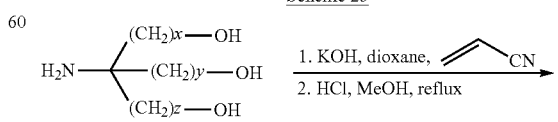

Series A
23a-d to 27a-d

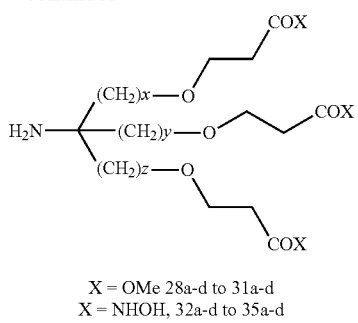

X = OMe 28a-d to 31a-d
X = NHOH, 32a-d to 35a-d

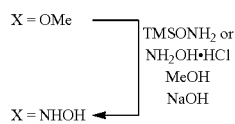

Scheme 26

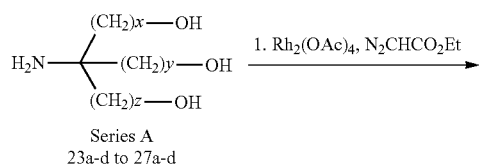

Series A
23a-d to 27a-d

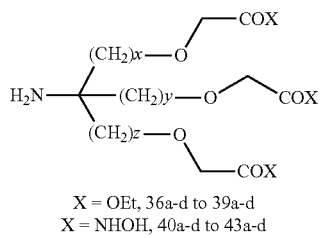

X = OEt, 36a-d to 39a-d
X = NHOH, 40a-d to 43a-d

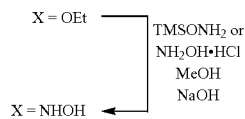

Example 17

Synthesis of Ligand 8

Scheme 27

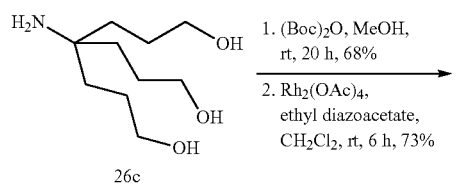

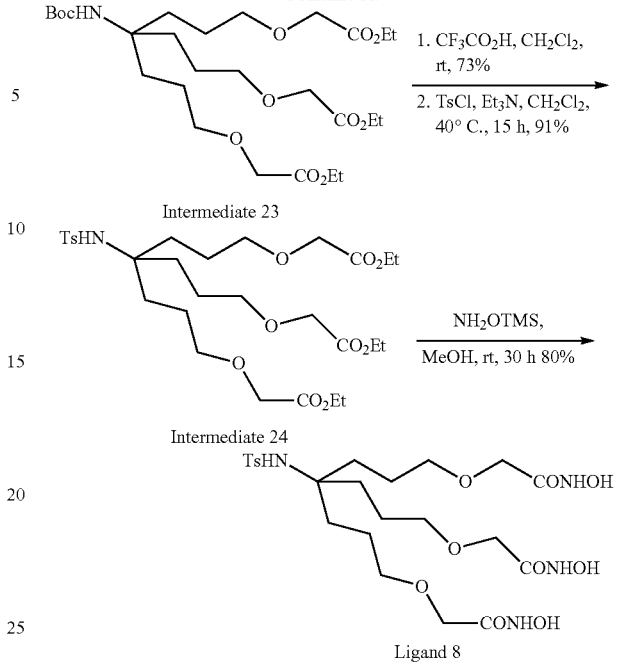

Ligand 8

Boc-protection of the amino group of amino triol 26c followed by rhodium acetate catalyzed alkylation of hydroxyl groups with ethyl diazoacetate gave intermediate 23. Boc-deprotection and reprotection of the amine by a tosyl group proceeded smoothly to give intermediate 24. Reaction of tri-ester (Intermediate 24) with O-trimethylsilyl hydroxylamine produced the ligand 8. The ligand 8 is a colorless solid and was purified by recrystallization from ethanol/isopropanol mixture (1:1) and its structure was determined by x-ray crystallography.

To a stirred solution of aminotriol 26c (1.65 g, 8.06 mmol) in dry MeOH (33 mL) was added (Boc)$_2$O (1.86 g, 8.5 mmol) and the mixture was stirred at room temperature for 20 h. The solvent was evaporated under reduced pressure and the residue was purified by column chromatography (SiO$_2$, CH$_2$Cl$_2$/MeOH gradient) to give the product (1.681 g, 68%) which was crystallized from CH$_2$Cl$_2$ as white crystals: IR (neat) 3453, 3400, 3307, 3228, 2947, 2872, 1689 cm$^{-1}$; $^1$H NMR (MeOD) δ (ppm) 3.43 (t, J=6.6 Hz, 6H), 1.57-1.51 (m, 6H), 1.42-1.35 (m, 6H), 1.32 (s, 9H); $^{13}$C (MeOD) δ (ppm) 156.5, 79.3, 63.4, 57.9, 32.4, 28.8, 27.5.

To a stirred solution of Boc protected amino triol (0.6 g, 1.96 mmol) and Rh$_2$(OAc)$_4$ (0.043 g, 0.098 mmol) in CH$_2$Cl$_2$ (6 mL) was added a solution of ethyl diazoacetate (1.05 ml, 9.98 mmol) in CH$_2$Cl$_2$ (50 ml) over a period of 1 h (syringe pump). After the addition was complete, the mixture was stirred for 5 h at room temperature. The solvent was removed under reduced pressure and the crude product was purified by column chromatography (SiO$_2$, hexane/EtOAc gradient) to give intermediate 23 (0.8 g, 73%): IR (neat) 3356, 2952, 2875, 1749, 1729, 1640 cm$^{-1}$; $^1$H NMR (CDCl$_3$) δ (ppm) 4.20 (q, J=7.1 Hz, 6H), 4.05 (s, 6H), 3.49 (t, J=6.3 Hz, 6H), 1.63-1.57 (m, 12H), 1.39 (s, 9H), 1.27 (t, J=7.1 Hz, 9H); $^{13}$C (CDCl$_3$) δ (ppm) 170.6, 154.3 78.7 72.1, 68.5, 60.9, 56.9, 31.8, 28.6, 23.7, 14.4; HRMS (FAB) calcd for C$_{27}$H$_{49}$NO$_{11}$Na [M+Na]$^+$: 586.32037. Found: 586.31950.

Intermediate 23 (1.147 g, 2.03 mmol) was in a 1:1 mixture of CF$_3$CO$_2$H (2.3 mL, 31 mmol) and CH$_2$Cl$_2$ (2.3 mL) and the resulting solution was stirred at room temperature. The reaction was monitored by TLC (50% EtOAc in hexane). When the reaction was complete, the solvent was evaporated under reduced pressure. The residue was dissolved in $CH_2Cl_2$ (10 mL) and a saturated solution of $Na_2CO_3$ was added dropwise while cautiously shaking the flask until $CO_2$ evolution ceased. The layers were separated and the aqueous layer was extracted with twice more with $CH_2Cl_2$ (2×20 mL). The combined organic layers were dried over $Na_2SO_4$ and evaporated under reduced pressure to give the crude product, which was purified by column chromatography ($SiO_2$, $CH_2Cl_2$/MeOH gradient) to give the free amine as a colorless oil (0.683 g, 73%): IR (neat) 3436, 2945, 2864, 1744, 1634, $cm^{-1}$; $^1H$ NMR ($CDCl_3$) δ (ppm) 4.19 (q, J=7.1 Hz, 6H), 4.05 (s, 6H), 3.52 (t, J=5.7 Hz, 6H), 1.65-1.54 (m, 12H), 1.24 (t, J=7.1 Hz, 9H); $^{13}C$ ($CDCl_3$) δ (ppm) 170.6, 72.1, 68.5, 61.0, 54.7, 35.2, 23.7, 14.3.

To the stirred solution of the free amine (0.68 g, 1.46 mmol) and tosyl chloride (0.66 g, 3.5 mmol) in $CH_2Cl_2$ (13 ml) was added $Et_3N$ (0.40 mL, 2.87 mmol) and the mixture was heated at 40° C. for 17 h. The solvent was evaporated under reduced pressure and the residue was dissolved in $CH_2Cl_2$ (25 ml) and washed with water (2×25 mL). The aqueous layer was extracted with $CH_2Cl_2$ (2×25 mL) and the combined organic layers was dried over $Na_2SO_4$ and concentrated under reduced pressure. The residue was purified by column chromatography ($SiO_2$, hexane/EtOAc gradient) to give intermediate 24 as a gummy solid (0.826 g, 91%): IR (neat) 3278, 2948, 2877, 1747 $cm^{-1}$; $^1H$ NMR ($CDCl_3$) δ (ppm) 7.68 (d, J=8.2 Hz, 2H), 7.17 (d, J=8.2 Hz, 2H), 4.10 (q, J=7.1 Hz, 6H), 3.88 (s, 6H), 3.24 (t, J=5.9 Hz, 6H), 2.31 (s, 3H), 1.48-1.38 (m, 12H), 1.18 (t, J=7.1 Hz, 9H); $^{13}C$ ($CDCl_3$) δ (ppm) 170.3, 142.6, 140.7, 129.3, 126.7, 72.4, 68.1, 61.9, 61.0, 32.7, 23.2, 21.3, 14.1; HRMS (FAB) calcd for $C_{29}H_{47}NO_{11}SNa$ $[M+Na]^+$: 640.27673. Found: 640.27700.

To a solution of the triester (intermediate 24) (0.54 g, 1.46 mmol) in MeOH (6 mL) was added $NH_2OTMS$ (1.00 mL, 8.17 mmol) and the mixture was stirred at room temperature for 30 h. The solvent was evaporated under reduced pressure to give a foamy solid. Recrystallization from a 1:1 mixture of EtOH and iPrOH yielded ligand 8 as a white crystalline solid (0.55 g, 80%): IR (neat) 3256, 2953, 2872, 1642 $cm^{-1}$; $^1H$ NMR ($D_2O$) δ (ppm) 7.81 (d, J=8.3 Hz, 2H), 7.44 (d, J=8.3 Hz, 2H), 3.99 (s, 6H), 3.35 (t, J=5.9 Hz, 6H), 2.43 (s, 3H), 1.52 (m, 12H); $^{13}C$ (MeOD) δ (ppm) 169.2, 144.4, 142.7, 130.7, 128.0, 72.9, 70.1, 63.0, 33.7, 24.2, 21.5; HRMS (FAB) calcd for $C_{23}H_{39}N_4O_{11}S$ $[M+H]^+$: 579.23358. Found: 579.23320. The product structure was confirmed X-ray crystallography.

Example 18

Synthesis of Ligand 9

Scheme 28

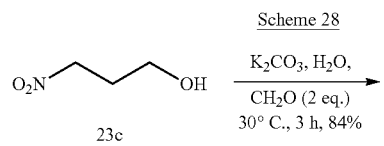

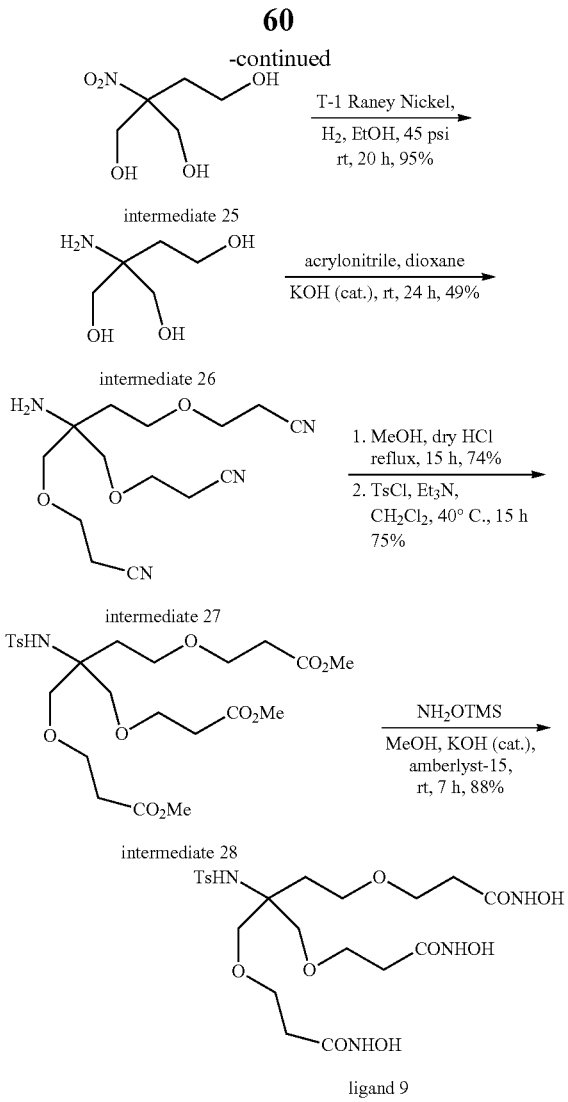

ligand 9

The base catalyzed addition of two equivalents of formaldehyde to 3-nitropropanol (Griesser, H.; Ohrlein, R.; Ehrler, R.; Jager, V. *Synthesis* 1999, 77, 236) 23c gave intermediate 25. The nitro group was reduced to an amine by hydrogenation using T-1 Raney nickel as a catalyst and hydrogen at 45 psi. The amino triol intermediate 26 was alkylated with acrylonitrile to give trinitrile. Treatment with HCl in methanol at reflux gave the aminotriester, which protected by tosylation to give intermediate 28. Reaction of intermediate 28 with O-trimethylsilyl hydroxylamine produced the ligand 9.

To a solution of 3-nitropropanol (6.70 g, 63.7 mmol) (Griesser, H.; Ohrlein, R.; Ehrler, R.; Jager, V. *Synthesis* 1999, 77, 236) in $H_2O$ (7 mL) were added 37 weight % formaldehyde solution (10 mL, 128 mmol) and solid $K_2CO_3.3/2H_2O$ (21.0 g, 127 mmol) and the mixture was stirred at room temperature for 1 h (reaction was exothermic) and then at 30° C. for 1 h. The reaction was monitored by TLC (10% MeOH in $CHCl_3$). 20% aqueous HCl solution was added drop wise with stirring until the effervescence of $CO_2$ ceased. The resulting mixture was washed with $CH_2Cl_2$ (2×30 mL) to remove some impurities and the aqueous layer was evaporated under reduced pressure. The residue was triturated with hot EtOH (3×50 mL) and the EtOH was filtered and evaporated under reduced pressure to yield intermediate 25 as a thick oil (8.85 g, 84%). IR (neat) 3378, 2949, 2888 $cm^{-1}$; $^1H$ NMR (D$_2$O) δ (ppm) 4.05 (ABq, Δδ=22.2 Hz, J=12.4 Hz, 4H) 3.73 (t, J=6.6 Hz, 2H), 2.26 (t, J=6.6 Hz, 2H); $^{13}$C NMR (D$_2$O) δ (ppm) 93.9, 62.1, 57.0, 33.3.

Freshly prepared T-1 Raney nickel (3.6 g) was transferred to a Parr hydrogenation flask as a slurry in absolute EtOH (45 mL). Intermediate 25 (4.80 g, 29.1 mmol) was dissolved in absolute EtOH (45 mL) and transferred to the hydrogenation flask. The resulting mixture was shaken on a Parr hydrogenator under 45 psi of H$_2$ at room temperature for 20 h. The flask was removed from the hydrogenator and flushed with argon for 20 min. The catalyst (pyrophoric when dry) was then filtered through a short pad of celite, which was never allowed to dry. The celite was washed with EtOH (3×30 mL). The EtOH was evaporated to give intermediate 26 a viscous brown gel (traces of EtOH was always present) (3.7 g, 95%) which was used in the next step without further purification. IR (neat) 2931, 2875 cm$^{-1}$; $^1$H NMR (D$_2$O) δ (ppm) 3.72 (t, J=7.2 Hz, 2H), 3.47 (s, 4H), 1.65 (t, J=7.2 Hz, 2H); $^{13}$C NMR (D$_2$O) δ (ppm) 64.7, 56.9, 54.8, 35.2

To a stirred solution of intermediate 26 (3.65 g, 27.0 mmol) and KOH pellets (0.4 g) in 1,4-dioxane (13 mL) was added acrylonitrile (6.3 mL, 94 mmol) drop wise over a period of 1 h. Once the addition was complete, the mixture was stirred at room temperature for 24 h. The solvent was evaporated under reduced pressure to yield thick liquid residue which was dissolved in CH$_2$Cl$_2$ (50 mL) and washed with H$_2$O (50 mL). The aqueous layer was re-extracted with additional portions of CH$_2$Cl$_2$ (2×30 mL). The combined CH$_2$Cl$_2$ fractions were dried over Na$_2$SO$_4$ and evaporated under reduced pressure and the residue was purified by column chromatography (SiO$_2$, 5% EtOH in EtOAc) to give intermediate 27 as a thick brown oil (3.89 g, 49%): IR (neat) 3371, 3307, 2873, 2245 cm$^{-1}$; $^1$H NMR (CDCl$_3$) δ (ppm) 3.68 (t, J=6.0 Hz, 4H), 3.65 (t, J=6.1 Hz, 2H), 3.62 (t, J=6.2 Hz, 2H), 3.41 (ABq, Δδ=19.5 Hz, J=8.7 Hz, 4H), 3.28 (t, J=6.0 Hz, 4H), 2.59 (t, J=6.0 Hz, 2H), 1.72 (t, J=6.1 Hz, 2H); $^{13}$C NMR (CDCl$_3$) δ (ppm) 118.2, 75.1, 67.5, 66.0, 65.8, 54.7, 34.6, 19.1, 19.0; HRMS (FAB) C$_{14}$H$_{23}$N$_4$O$_3$ [M+H]$^+$ calcd 295.17703. found 295.17720.

Dry HCl gas was bubbled into a solution of intermediate 27 (1.43 g, 4.86 mmol) in MeOH (12 ml) until it was saturated. The resulting mixture was heated at reflux for 10 h. Saturated Na$_2$CO$_3$ was added drop wise while stirring the mixture until CO$_2$ effervescence ceased. The solution was extracted with EtOAc (3×30 mL). The combined organic layers were washed with brine, dried over Na$_2$SO$_4$ and evaporated to obtain the amino triester as a liquid (1.41 g, 74%), which was used in the next step without further purification. IR (neat) 2951, 2875, 1732 cm$^{-1}$; $^1$H NMR (CDCl$_3$) δ (ppm) 3.74-3.63 (m, 15H), 3.53 (t, J=6.5 Hz, 2H), 3.26 (ABq, Δδ=13.8 Hz, J=8.9 Hz, 4H), 2.55 (t, J=6.3 Hz, 6H), 2.03 (br s, 2H), 1.62 (t, J=6.4 Hz, 2H); $^{13}$C NMR (CDCl$_3$) δ (ppm) 172.3, 172.2, 75.1, 67.4, 66.8, 66.3, 54.7, 51.8, 51.7, 35.1, 35.0, 34.5; HRMS (FAB) C$_{17}$H$_{32}$NO$_9$ [M+H]$^+$ calcd 394.20770. found 394.20860.

To a stirred solution of the amino triester (1.40 g, 3.56 mmol) and TsCl (1.60 g, 8.40 mmol) in CH$_2$Cl$_2$ (32 mL) was slowly added Et$_3$N (1.0 mL, 7.2 mmol) and the resulting mixture was heated at reflux for 20 h. The solvent was evaporated under reduced pressure and the residue was dissolved in CH$_2$Cl$_2$ (50 mL), washed with water (2×25 mL), dried over Na$_2$SO$_4$ and concentrated under reduced pressure. The crude product was purified by column chromatography (SiO$_2$, hexanes/EtOAc gradient) to give intermediate 28 as a thick oil (1.42 g, 74%): IR (neat) 3287, 2953, 2876, 1732 cm$^{-1}$; $^1$H NMR (CDCl$_3$) δ (ppm) 7.73 (d, J=8.3 Hz, 2H), 7.24 (d, J=8.3 Hz, 2H), 5.58 (s, 1H), 3.67 (s, 3H), 3.64 (s, 6H), 3.58 (t, J=6.3 Hz, 2H), 3.50-3.36 (m, 10H), 2.52 (t, J=6.3 Hz, 2H), 2.39 (t, J=6.3 Hz, 4H), 2.38 (s, 3H), 1.88 (t, J=6.0 Hz, 2H); $^{13}$C NMR (CDCl$_3$) δ (ppm) 172.1, 172.0, 142.8, 140.6, 129.3, 126.9, 72.1, 66.9, 66.5, 66.2, 61.6, 51.8, 51.7, 34.8, 34.6, 32.6, 21.5; HRMS (FAB) C$_{24}$H$_{38}$NO$_{11}$S [M+H]$^+$ calcd 548.21655. found 548.21570.

To a solution of intermediate 28 (0.5 g, 0.91 mmol) in dry MeOH (5.5 mL) was added NH$_2$OTMS (0.67 mL, 5.48 mmol) and the resulting solution was stirred at room temperature. The reaction was monitored by TLC (50% EtOAc in hexanes). No reaction was observed after 3 h. KOH (0.3 g) was added and stirring was continued for an additional 45 min. Amberlyst-15 (2.6 g, washed with dry MeOH) was added to the reaction mixture and stirring was continued for 1 h. The mixture was filtered and the filtrate was evaporated under reduced pressure to obtain ligand 9 as a solid (0.44 g, 88%): IR (neat) 3215, 2876, 1638 cm$^{-1}$; $^1$H NMR (D$_2$O) δ (ppm) 7.80 (d, J=8.2 Hz, 2H), 7.47 (d, J=8.2 Hz, 2H), 3.64 (t, J=6.0 Hz, 2H), 3.48-3.52 (m, 6H), 3.39 (s, 4H), 2.44 (s, 3H), 2.40 (t, J=6.0 Hz, 2H), 2.32 (t, J=5.8 Hz, 4H), 1.85 (t, J=6.7 Hz, 2H); $^{13}$C NMR (MeOD) δ (ppm) 171.0, 170.9, 144.4, 141.9, 123.5, 127.9, 72.5, 67.6, 67.3, 62.5, 54.9, 34.4, 33.3, 21.5; HRMS (FAB) C$_{21}$H$_{35}$N$_4$O$_{11}$S [M+H]$^+$ calcd 551.20227. found 551.20260.

Example 19

General Synthesis of Macrocyclic Ligands

A general approach to macrocyclic ligands begins with mono protected aminotriols (series B, 24ad-27ad). The free hydroxyls are alkylated with t-butyl acrylate under basic conditions. The hydroxyl protecting is removed and the hydroxyl is alkylated methyl acrylate. Finally, the amine is protected with a Cbz group to give compounds 44a-d to 47a-d. The t-butyl groups are removed selectively with TFA and the resulting diacids are converted into the acid chlorides using oxalyl chloride. Macrocycles are prepared by reaction of diacid chlorides with benzyl protected hydroxylamines under high dilution conditions. The remaining methyl is reacted with O-benzyl hydroxylamine and then benzyl groups are removed via hydrogenolysis to yield the hydroxamic acids 50a-d to 53a-d.

Scheme 29.

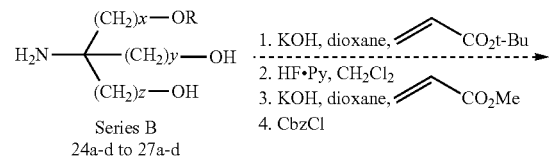

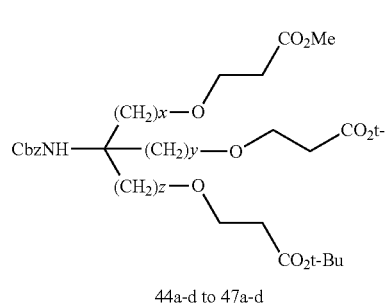
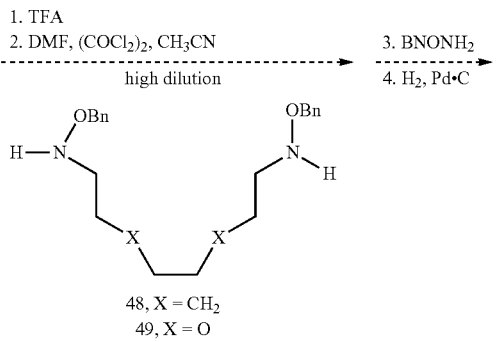

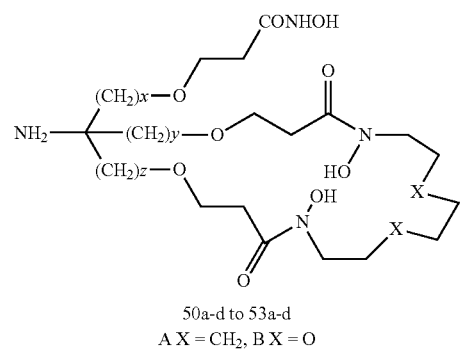

Example 20

General Synthesis of Tetrahydroxamic Acids Type A

Tetrahydroxamates, designed to mimic the structure of DFO-B, can be prepared from protected amino diacids. The amino diol scaffold for the diacids are prepared using chemistry similar to that for the aminotriols (para 00199). Starting with nitroalkanes (54), two identical alkenol chains can be added with 1 carbon atom (55), 2 carbon atoms (56), 3 carbon atoms (57), or 4 carbon atoms (58). In all cases, reduction of the nitro group with hydrogen over T1 Raney nickel will yield the amino compounds.

Scheme 30

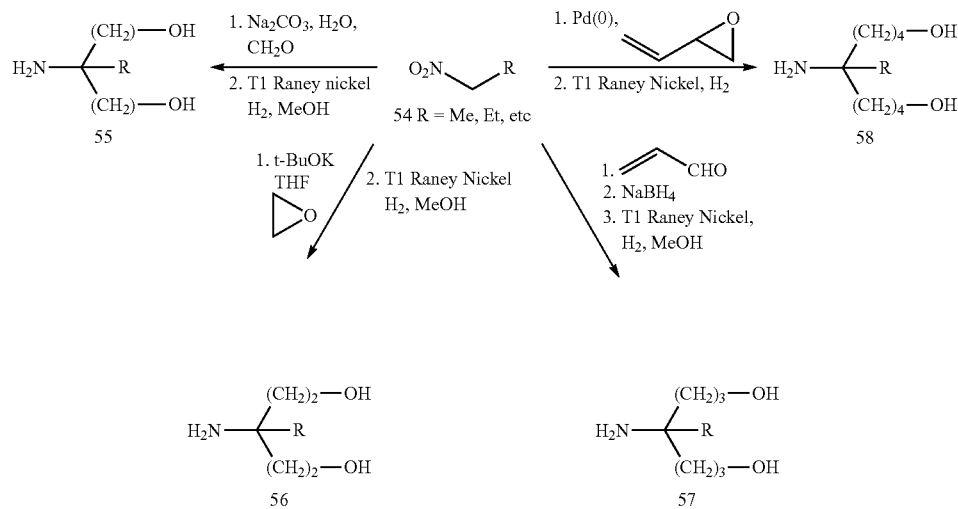

The diesters with different length side arms can be prepared by the reactions of aminodiol scaffolds (55-58)] with acrylonitrile then HCl/MeOH (59-62) or diazoacetate (67-70). The resulting esters (59-62 and 67-70) are converted to the acids (63-66 and 71-74) by hydrolysis with lithium hydroxide.

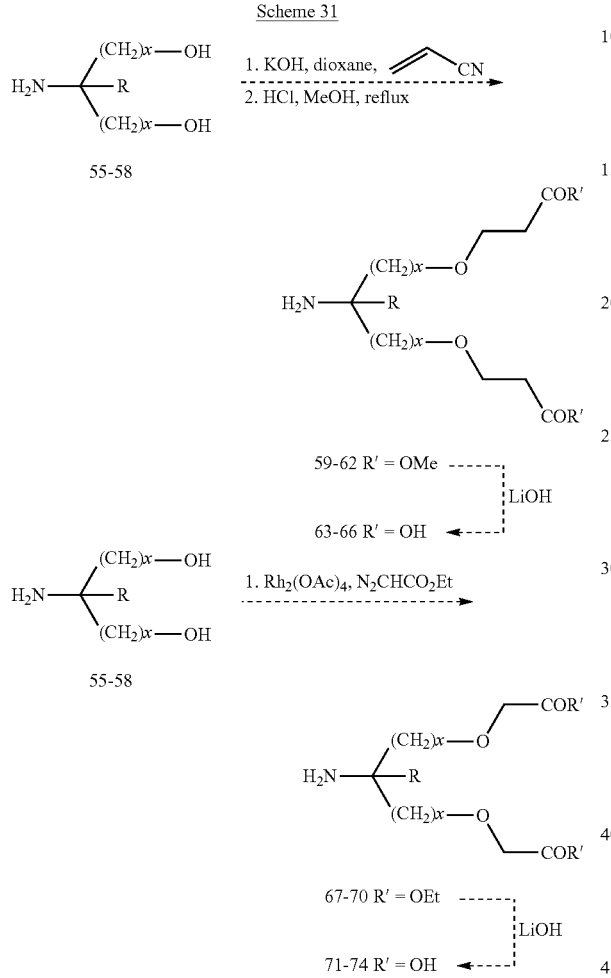

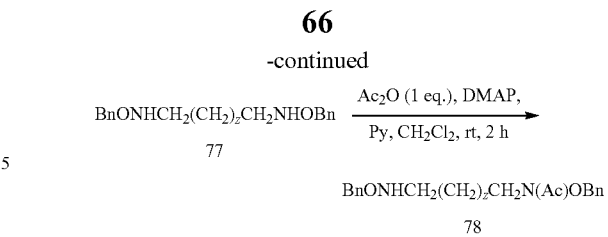

The acids are coupled with two equivalents of protected monoacyl dihydroxylamine (78) using dicyclohexyl carbodiimide (DCC) and then the benzyl groups are removed via hydrogenolysis to give the tetrahydroxamic acids 79

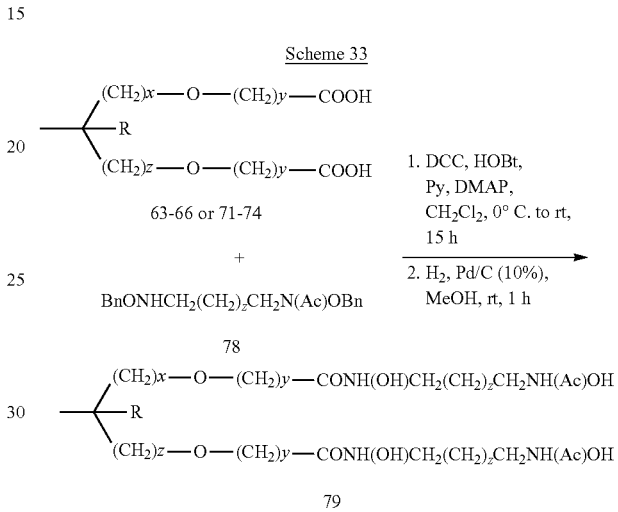

For series A, the acids are coupled with a protected monoacyl dihydroxylamine (78). The oximes are made by oxidizing diols to dialdehydes and condensing with O benzyl (or other protected) hydroxylamine to give an oxime. Reduction of the oxime with sodium cyanoborohydride under acidic conditions give the protected dihydroxylamine which is monoacylated with one equivalent acetic anhydride.

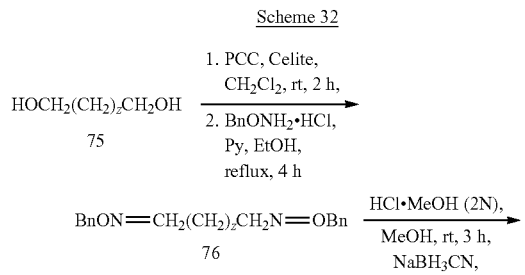

Example 21

(Type A) Tetrahydroxamate Ligand 10

PCC oxidation of 1,9-nonanediol gave nonanedial, which was reacted with O-benzylhydroxylamine hydrochloride and pyridine in refluxing ethanol to produce the dioxime intermediate 29 Sodium cyanoborohydride reduction of dioxime gave benzyl protected bis-hydroxylamine intermediate 30. Acetylation of one of the hydroxylamine nitrogen using one equivalent of acetic anhydride led to the formation of intermediate 31.

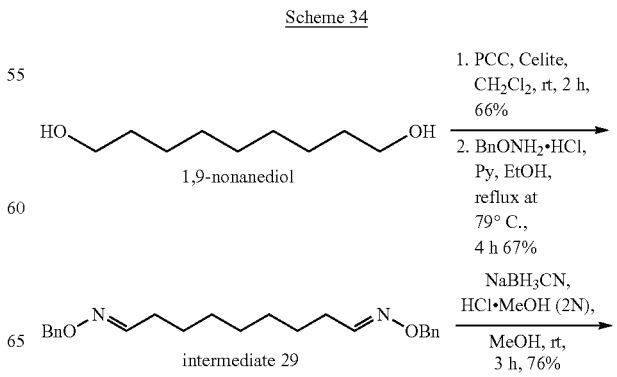

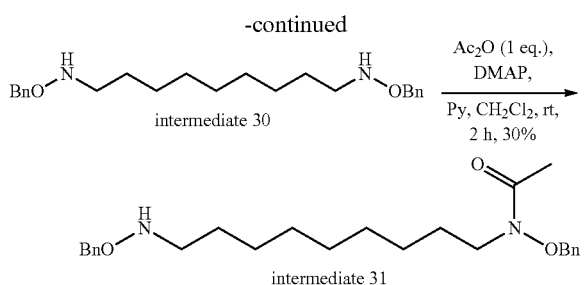

The dicarboxylic acid (intermediate 32) was prepared (Scheme 35) by the base catalyzed hydrolysis of intermediate 17 (R. A. Yokel, W. R. Harris, C. D. Spilling and C.-G. Zhan (2011) U.S. Pat. No. 7,932,326).

Scheme 35

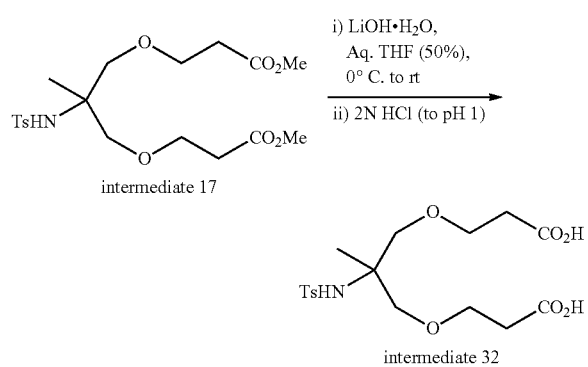

Finally, the two partners 32 and 31 were coupled using DCC (Scheme 36) and deprotected by hydrogenation with $H_2$ over 10% Pd on C to obtain ligand 10.

To a solution of PCC (32.33 g, 150.0 mmol) and with a suspension of celite (11.0 g) in $CH_2Cl_2$ (300 mL) was added 1,9-nonanediol (10.0 g, 62.4 mmol). This solution was stirred at room temperature and the reaction was monitored by TLC (1:1 hexanes/EtOAc). After 2 h the reaction was complete. The reaction mixture was passed through a short column of silica and celite, which was washed with $CH_2Cl_2$ (5×50 mL). The solvent evaporated under reduced pressure and the residue was purified by column chromatography ($SiO_2$ hexanes/EtOAc gradient) to give the dialdehyde (A. Ozane, L Pouysegu, D. Depernet, B. Francois, S. Quideau Organic Letter 2003, 5, 2903-2906) as a colorless liquid (6.4 g, 66%): $^1$H NMR ($CDCl_3$) δ (ppm) 9.73 (t, J=1.8 Hz, 2H), 2.40 (td, J=7.3, 1.8 Hz, 4H), 1.58 (m, 4H), 1.32 (br s, 6H); $^{13}$C NMR ($CDCl_3$) δ (ppm) 202.8, 43.9, 29.2, 29.0, 22.0.

To a solution of nonanedial (5.60 g, 35.8 mmol) and O-benzylhydroxylamine hydrochloride (15.0 g, 94.0 mmol) in EtOH (120 mL) was added pyridine (7.6 mL, 94 mmol) drop wise. The resulting solution was heated at reflux for 4 h. The solvent was evaporated under reduced pressure and the residue was dissolved in $CH_2Cl_2$ (200 mL) and washed with water (3×100 mL). The aqueous layer was re-extracted with $CH_2Cl_2$ (2×100 mL). The combined organic layers were dried over $Na_2SO_4$, evaporated under reduced pressure, and the residue was purified by column chromatography ($SiO_2$ hexanes) to give intermediate 29 as a colorless liquid (8.01 g, 61%) as a 1.5:1 mixture of geometric isomers. IR (neat) 3030, 2925, 2856 cm$^{-1}$; $^1$H NMR ($CDCl_3$) δ (ppm) 7.46 (t, J=6.2 Hz, 0.6H), 7.39-7.31 (m, 5H), 6.69 (t, J=5.4 Hz, 0.4H), 5.13 (s, 0.8H), 5.08 (s, 1.2H), 2.39 (app q, 0.8H), 2.20 (app q, 1.2H), 1.48 (m, 2H), 1.32 (m, 3H); $^{13}$C NMR ($CDCl_3$) δ (ppm) 152.6, 151.7, 138.3, 137.8, 128.5 (×2), 128.3, 128.0, 127.9, 127.8, 75.8, 75.6, 29.6, 29.3, 29.1, 29.0, 26.7, 26.2, 25.9; HRMS (FAB) $C_{23}H_{31}N_2O_2$ [M+H]$^+$ calcd 367.23856. found 367.23830. One of the isomers was isolated and characterized completely. $^1$H NMR ($CDCl_3$) δ (ppm) 7.39 (t, J=6.2 Hz, 2H), 7.31-7.24 (m, 10H), 5.00 (s, 4H), 2.13 (app q,

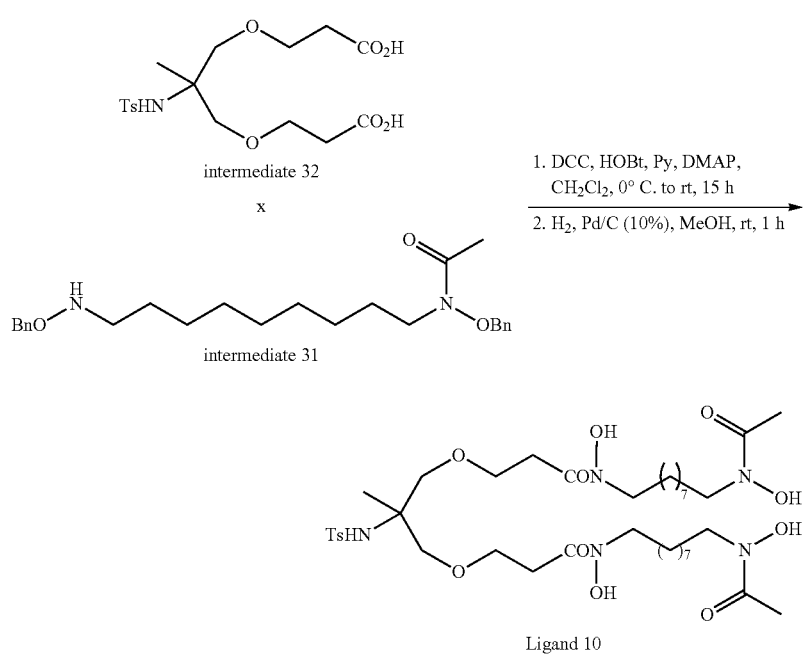

Ligand 10

4H), 1.41 (quin, J=6.8 Hz, 4H), 1.25 (m, 6H); $^{13}$C NMR (CDCl$_3$) δ (ppm) 151.7, 137.9, 128.5, 128.4, 128.0, 127.9, 75.6, 29.6, 29.1, 29.0, 26.7.

To a solution of intermediate 29 (0.11 g, 0.3 mmol) and NaCNBH$_3$ (0.042 g, 0.66 mmol) in MeOH (2 mL) was added 2N HCl in MeOH drop wise until the solution pH was between 3 and 4. The resulting mixture was stirred for 3 h at room temperature. The solvent was evaporated under reduced pressure and the solid residue was dissolved in water (2 mL) and 6 N KOH solution was added drop wise to adjust the solution pH to >9. The aqueous solution was extracted with CH$_2$Cl$_2$ (3×10 ml), and combined organic extracts were washed with brine (20 mL), dried over Na$_2$SO$_4$ and evaporated under reduced pressure. The residue was purified by column chromatography (SiO$_2$ hexanes/EtOAc gradient) to give the intermediate 30 as a colorless liquid (0.083 g, 76%): IR (neat) 3028, 2924, 2852, 1453, 1363 cm$^{-1}$; $^1$H NMR (CDCl$_3$) δ (ppm) 7.30-7.38 (m, 10H), 4.73 (s, 4H), 2.94 (t, J=7.0 Hz, 4H), 1.52 (app quin, J=6.7 Hz, 4H), 1.30 (br s, 10H); $^{13}$C NMR (CDCl$_3$) δ (ppm) 138.2, 128.5 (×2), 127.9, 76.3, 52.3, 29.6, 27.4, 27.3.

To a solution of intermediate 30 (0.40 g, 1.08 mmol) in CH$_2$Cl$_2$ (15 mL) was added DMAP (0.13 g, 1.06 mmol), pyridine (0.18 mL, 2.22 mmol), and Ac$_2$O (0.102 mL, 1.08 mmol) sequentially and the resulting mixture was stirred at room temperature for 2 h. The mixture was diluted with CH$_2$Cl$_2$ (20 mL) was added and washed with saturated NaHCO$_3$ (20 mL). Organic layer was dried over Na$_2$SO$_4$ and evaporated under reduced pressure and the solid residue was purified by column chromatography (SiO$_2$, hexanes/EtOAc gradient) to give intermediate 31 as a colorless liquid (0.120 g, 30%): IR (neat) 3031, 2927, 2854, 1660 cm$^{-1}$; $^1$H NMR (CDCl$_3$) δ (ppm) 7.31-7.39 (m, 10H), 5.56 (br s, 1H), 4.82 (s, 2H), 4.71 (s, 2H), 3.63 (t, J=6.9 Hz, 2H), 2.93 (t, J=7.1 Hz, 2H), 2.10 (s, 3H), 1.64 (m, 2H), 1.50 (m, 2H), 1.29 (br s, 10H); $^{13}$C NMR (CDCl$_3$) δ (ppm) 154.2, 138.2, 134.7, 129.3, 129.0, 128.9, 128.5 (×2), 127.9, 76.4, 76.3, 52.3, 29.6, 29.4, 27.5, 27.3, 27.0, 26.9, 20.7; HRMS (FAB) C$_{25}$H$_{37}$N$_2$O$_3$ [M+H]$^+$ calcd 413.28040. found 413.2776.

To a solution of intermediate 17 (3.00 g, 6.96 mmol) in aqueous THF (1:1, 30 ml) at 0° C., was added LiOH·H$_2$O (1.17 g, 27.9 mmol) and the resulting mixture was stirred for 1 h. After 1 h, the flask was allowed to warm to room temperature while stirring was continued. When all starting material was consumed (TLC 1:1 EtOAc/hexanes), the reaction was quenched with 2N HCl and solution pH was adjusted to 1. The mixture was filtered (to remove LiCl) and extracted with CH$_2$Cl$_2$ (3×50 mL). The combined organic extracts were washed with brine, dried over Na$_2$SO$_4$ and evaporated under reduced pressure to give the diacid as a white powder (2.67 g, 95%) which was used in the next step without further purification. IR (neat) 3300, 3051, 2925, 2875, 1697 cm$^{-1}$; $^1$H NMR (D$_2$O) δ (ppm) 7.84 (d, J=8.3 Hz, 2H), 7.45 (d, J=8.3 Hz, 2H), 3.60-3.53 (m, 4H), 3.37 (ABq, Δδ=22.8 Hz, J=10 Hz, 4H), 2.53 (t, J=6.0 Hz, 4H), 2.44 (s, 3H), 1.14 (s, 3H); $^{13}$C NMR (MeOD) δ (ppm) 175.6, 144.3, 142.5, 130.5, 128.0, 74.8, 68.0, 60.1, 35.7, 21.5, 19.4; HRMS (FAB) C$_{17}$H$_{26}$NO$_8$S [M+H]$^+$ calcd 404.13790. found 404.13880.

Ligand 10. To a solution of intermediate 31 (0.40 g, 0.97 mmol) and DMAP (0.16 g, 1.31 mmol) in CH$_2$Cl$_2$ (10 mL) and pyridine (0.11 mL, 1.4 mmol) was added a solution of intermediate 32 (0.18 g, 0.45 mmol) and HOBt (0.14 g, 1.03 mmol) in CH$_2$Cl$_2$ (10 mL) and the mixture was cooled to 0° C. DCC (0.2 g, 0.97 mmol) was added and the mixture was stirred for 1 h at 0° C., then it was allowed to warm to room temperature and was stirred for an additional 15 h. The solvent was evaporated under reduced pressure and the residue was purified by column chromatography (SiO$_2$, hexanes/EtOAc gradient) to give the tetrabenzyl tetrahydroxamate as a thick colorless oil (0.342 g, 65%): IR (neat) 3033, 2930, 2856, 1650, 1601 cm$^{-1}$; $^1$H NMR (CDCl$_3$) δ (ppm) 7.75 (d, J=8.2 Hz, 2H), 7.45-7.33 (m, 20H), 7.17 (d, J=8.2 Hz, 2H), 5.74 (s, 1H), 4.78 (s, 4H), 4.76 (s, 4H), 3.63-3.59 (m, 12H), 3.30 (ABq, Δδ=52.5 Hz, J=9.2 Hz, 4H), 2.66-2.55 (m, 4H), 2.25 (s, 3H), 2.04 (s, 6H), 1.58 (m, 8H), 1.23 (br s, 20H), 1.08 (s, 3H); $^{13}$C NMR (CDCl$_3$) δ (ppm) 172.2, 172.0, 142.4, 140.8, 134.4, 134.3, 129.9, 129.3, 129.2, 129.0, 128.7, 128.6, 128.5, 127.0, 126.7, 126.2, 77.6, 76.2, 76.0, 73.7, 66.7, 58.6, 45.2, 32.5, 29.2, 29.0, 26.7, 26.5, 21.3, 20.4, 18.1; HRMS (FAB) C$_{67}$H$_{94}$N$_5$O$_{12}$S [M+H]$^+$ calcd 1192.66199. found 1192.66110.

To a solution of tetrabenzyl tetrahydroxamate (0.34 g, 0.28 mmol) in MeOH (11 mL) was added 10% Pd/C (0.074 g). Flask was then evacuated and flushed with H$_2$ from two balloons and the mixture was stirred under H, at room temperature until the starting material was consumed (TLC, 70% EtOAc in hexanes). The reaction flask was purged with Ar and the mixture was filtered. The filtrate was evaporated under reduced pressure to give ligand 10 as a foamy solid (0.22 g, 91%): IR (neat) 3360, 3060, 2928, 2857, 1611 cm$^{-1}$; $^1$H NMR (MeOD) δ (ppm) 7.68 (d, J=8.2 Hz, 2H), 7.23 (d, J=8.2 Hz, 2H), 3.52-3.46 (m, 12H), 3.27-3.17 (m, 4H overlapping with MeOH peak), 2.58 (t, J=6.0 Hz, 4H), 2.31 (s, 3H), 1.99 (s, 6H), 1.51 (br s, 8H), 1.21 (br s, 20H), 1.00 (s, 3H); $^{13}$C NMR (MeOD) δ (ppm) 173.6, 173.5, 144.2, 142.6, 130.5, 128.0, 75.0, 68.0, 60.1, 48.9, 33.9, 30.6, 30.4, 27.8, 21.6, 20.3, 19.5; HRMS (FAB) C$_{39}$H$_{70}$N$_5$O$_{12}$S [M+H]$^+$ calcd 832.4742. found 832.4725.

Example 22

Tetrahydroxamate ligand 11

Ligand 11 is prepared from amino diester intermediate 17. The amine is protected with Cbz to give intermediate 33. Hydrolysis with lithium hydroxide yields diacid intermediate 34 which is coupled with intermediate 31 using DCC. Global deprotection of the Cbz and benzyl protecting groups gives ligand 11.

Scheme 37

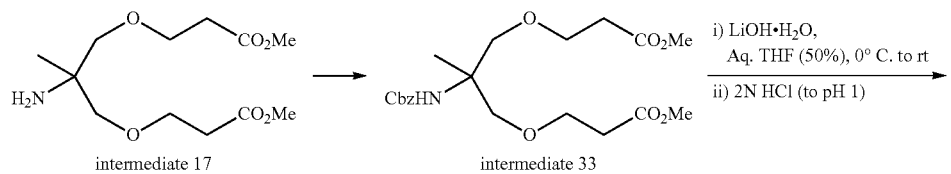

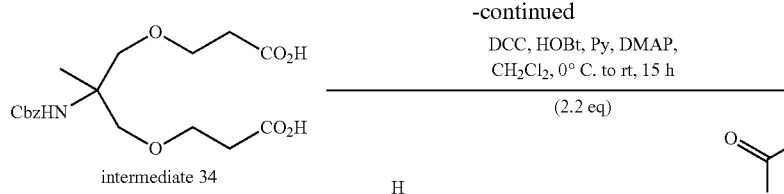

intermediate 34

-continued

DCC, HOBt, Py, DMAP,
CH$_2$Cl$_2$, 0° C. to rt, 15 h
(2.2 eq)

H$_2$, Pd/C (10%),
MeOH, rt, 1 h

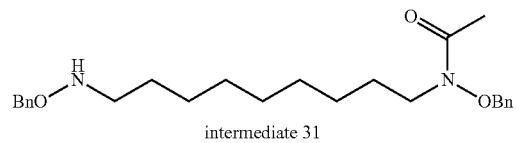

intermediate 31

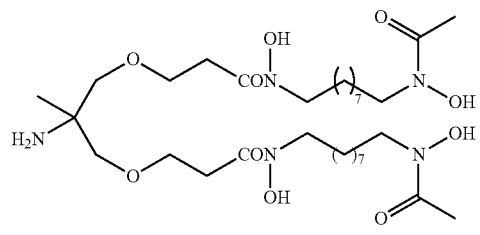

Ligand 11

To a stirred solution of intermediate 17 (R. A. Yokel, W. R. Harris, C. D. Spilling and C.-G. Zhan (2011) U.S. Pat. No. 7,932,326) (2.0 g, 7.2 mmol) in THF (57 mL) was added 10% aqueous Na$_2$CO$_3$ (57.0 mL, 53.7 mmol). After 15 minutes at room temperature CbzCl (1.13 mL, 7.93 mmol) was added and stirring was continued for an additional 5 h. The layers were separated and the aq. layer was extracted with EtOAc (2×30 mL). The combined organic extracts were washed with water and brine, dried over Na$_2$SO$_4$ and evaporated under reduced pressure. The residue was purified by column chromatography (SiO$_2$, hexane/EtOAc gradient) to give intermediate 33 as a colorless oil (1.9 g, 65%): IR (neat) 3366, 2951, 2875, 1731 cm$^{-1}$; $^1$H NMR (300 MHz, CDCl$_3$) δ (ppm) 7.33-7.31 (m, 5H), 5.28 (s, 1H), 5.01 (s, 2H), 3.67 (t, J=6.2 Hz, 4H), 3.64 (s, 6H), 3.47 (ABq, Δδ=42.9 Hz, J=9.0 Hz, 4H), 2.53 (t, J=6.2 Hz, 4H), 1.29 (s, 3H); $^{13}$C NMR (300 MHz, CDCl$_3$) δ (ppm) 172.0, 155.1, 137.4, 128.5, 128.0, 72.9, 66.8, 66.1, 55.7, 51.7, 34.8, 19.8; HRMS (FAB) C$_{20}$H$_{30}$NO$_8$ [M+H]$^+$ calcd 412.19714. found 412.19750.

To a solution of intermediate 33 (7.40 g, 18.0 mmol) in 50% aqueous THF (75 mL) was added LiOH (1.68 g, 70.1 mmol) at 0° C. and the resulting mixture was stirred for 1 h. After 1 h, the flask was allowed to warm to room temperature with continued stirring. Once the starting material was consumed (TLC 1:1 EtOAc/hexanes), the reaction was quenched with 2N HCl to adjust the solution pH to 2. The mixture was extracted with CH$_2$Cl$_2$ (3×100 mL) and the combined extracts were washed with brine, dried over Na$_2$SO$_4$, and evaporated under reduced pressure to give intermediate 34 as a colorless gel (6.8 g, quant) which was used in the next step without further purification. IR (neat) 3033, 2939, 2878, 1709 cm$^{-1}$; $^1$H NMR (300 MHz, CDCl$_3$) δ (ppm) 10.28 (br s, 2H), 7.35-7.29 (m, 5H), 5.34 (br s, 1H), 5.04 (s, 2H), 3.68 (t, J=6.2 Hz, 4H), 3.49 (ABq, Δδ=39.6 Hz, J=8.9 Hz, 4H), 2.57 (t, J=6.2 Hz, 4H), 1.31 (s, 3H); $^{13}$C NMR (300 MHz, CDCl$_3$) δ (ppm) 177.3, 155.3, 136.5, 128.5 (×2), 128.3, 128.1, 128.0, 77.3, 72.8, 66.4, 55.7, 34.6, 19.0; HRMS (FAB) C$_{18}$H$_{26}$NO$_8$ [M+H]$^+$ calcd 384.1658. found 384.1648.

To a solution of intermediate 31 (1.1 g, 2.66 mmol) and DMAP (0.44 g, 3.60 mmol) in CH$_2$Cl$_2$ (50 mL) and pyridine (0.29 mL 3.58 mmol), was added intermediate 34 (0.47 g, 1.22 mmol) and HOBt (0.37 g, 2.71 mmol) in CH$_2$Cl$_2$ (50 mL). The mixture was cooled to 0° C. and DCC (0.58 g, 2.81 mmol) was added. The mixture was stirred for 1 h at 0° C., then allowed to warm to room temperature and stirred for additional 15 h. The solvent was concentrated under reduced pressure and the solids were removed by filtration (DCC urea) and washed with CH$_2$Cl$_2$. The filtrate was evaporated under reduced pressure and the residue was purified by column chromatography (SiO$_2$, EtOAc/hexanes gradient) to give the Cbz tetrabenzyl tetrahydroxylamine as a white solid product (0.80 g, 56%): IR (neat) 3029, 2930, 2856, 1719, 1649 cm$^{-1}$; $^1$H NMR (300 MHz, CDCl$_3$) δ (ppm) 7.36-7.25 (m, 5H), 5.49 (s, 1H), 5.00 (s, 2H), 4.79 (s, 4H), 4.78 (s, 4H), 3.71 (t, J=6.2 Hz, 4H), 3.60-3.55 (m, 8H), 3.49 (ABq, Δδ=45.8 Hz, J=9.1 Hz, 4H), 2.64 (t, J=5.9 Hz, 4H), 2.07 (s, 6H), 1.60-1.58 (m, 8H), 1.32 (s, 3H), 1.24 (s, 20H); $^{13}$C NMR (300 MHz, CDCl$_3$) δ (ppm) 172.4, 172.2, 155.1, 136.8, 134.5, 129.1 (×2), 128.9, 128.8, 128.7, 128.4, 127.9, 127.8, 77.4, 76.3, 76.2, 73.2, 67.1, 65.9, 55.7, 45.3, 33.9, 32.7, 29.4, 29.3, 29.2, 29.1, 26.8, 26.7, 26.6, 20.5, 19.0; HRMS (FAB) C$_{68}$H$_{94}$N$_5$O$_{12}$ [M+H]$^+$ calcd 1172.68994. found 1172.68620.

To a solution of Cbz tetrabenzyl tetrahydroxylamine (0.50 g, 0.43 mmol) in MeOH (16 mL) was added 10% Pd/C (0.11 g) under argon. The flask was evacuated and flushed with H$_2$ (balloons) and then mixture was stirred under H$_2$ at room temperature until the starting material was consumed (TLC analysis 70% EtOAc in hexanes). The reaction mixture was then flushed with Ar and filtered. The filtrate was evaporated under reduced pressure to obtain ligand 11 as a sticky solid (0.29 g, quant): IR (neat) 3133 (broad), 2927, 2854, 1607 cm$^{-1}$; $^1$H NMR (300 MHz, MeOD) δ (ppm) 3.52 (t, J=6.1 Hz, 4H), 3.37 (t, J=7.1 Hz, 4H), 3.35 (t, J=7.1 Hz, 4H), 3.18 (ABq, Δδ=26.4 Hz, J=9.6 Hz, 4H), 2.53 (t, J=6.1 Hz, 4H), 1.85 (s, 6H), 1.38 (m, 8H), 1.09 (m, 20H), 0.92 (s, 3H); $^{13}$C NMR (300 MHz, MeOD) δ (ppm) 173.5, 173.4, 74.9, 68.3, 56.5, 48.9, 34.8, 33.8, 30.7, 30.4, 27.8, 26.8, 26.2, 20.4 (×2); HRMS (FAB) C$_{32}$H$_{64}$N$_5$O$_{10}$ [M+H]$^+$ calcd 678.46533. found 678.46620.

Example 23

General Synthesis of Tetrahydroxamic Acids Type B

The synthesis of type B tetrahydroxamate ligands begins with selective reduction of α,ω diacid mono esters 80 (Z>4) using borane in THF to give the hydroxy esters, which are reoxidized to give the ester aldehydes 81. The aldehydes are condensed with O-benzyl (or other protected) hydroxylamine to give oximes 82. Reduction with sodium cyanoborohydride under acidic conditions will yield the hydroxylamine esters 83.

Scheme 38

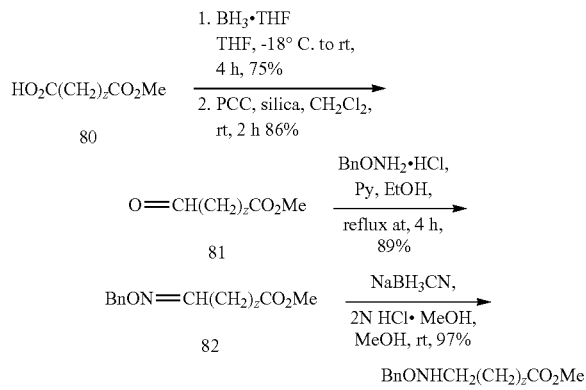

The hydroxylamine esters 83 are condensed with diacids (63-66 or 71-74) to benzyl protected dihydroxamic acids 84. Reaction of the ester with O-trimethylsilyl hydroxylamine in MeOH and removal of the benzyl groups via hydrogenolysis will yield the type B tetrahydroxamates 85.

Scheme 39

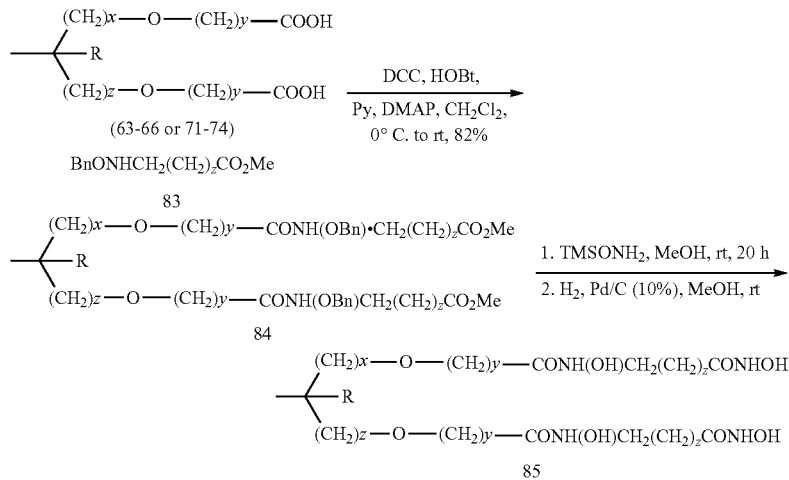

Example 24

(Series B) Tetrahydroxamte Ligand 12

The acid group of monomethyl azelate was selectively reduced with $BH_3$ to give an alcohol (Scheme 40), which was reoxidized with PCC to form the aldehyde intermediate 35. The aldehyde was reacted with O-benzylhydroxylamine hydrochloride in the refluxing ethanol to obtain the oxime ester intermediate 36, which was reduced to the benzyl protected hydroxylamine ester intermediate 37.

Scheme 40

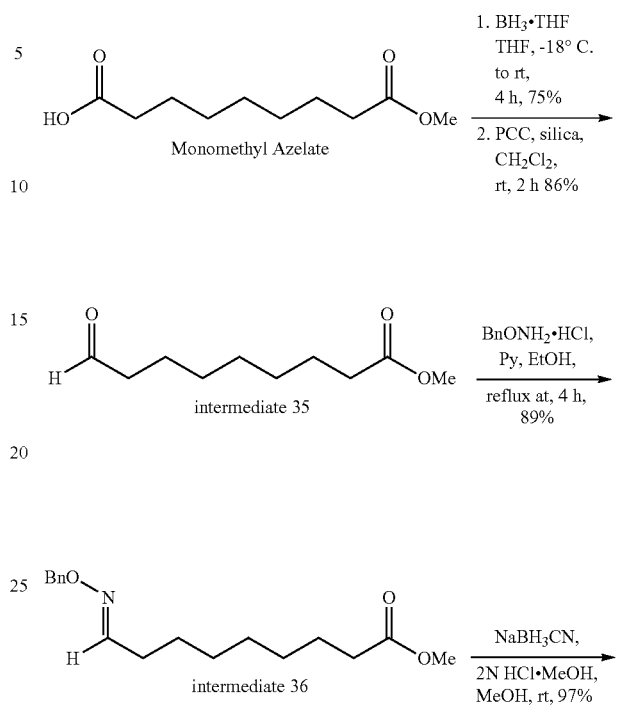

-continued

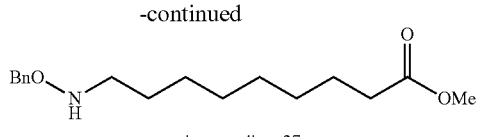

DCC mediated coupling of dicarboxylic acid intermediate 17 with intermediate 37 produced the benzyl protected hydroxamic acid intermediate 38 (Scheme 41), which was purified by chromatography. The ester groups were then converted to the hydroxamic acids by reaction with O-trimethylsilyl hydroxylamine. The benzyl protected hydroxamic acid groups were deprotected using hydrogenolysis to give ligand 12.

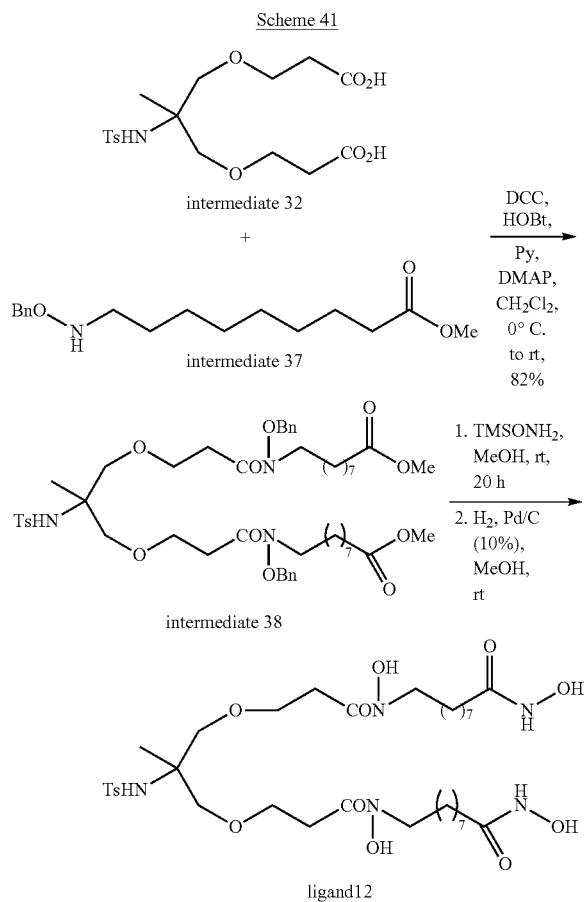

To a solution of intermediate 35 (Kai, K.; Takeuchi, J.; Kataoka, T.; Yokoyama, M.; Watanabe, N. *Tetrahedron* 2008, 64, 6760) (3.40 g, 18.2 mmol) and O-benzylhydroxylamine hydrochloride (3.79 g, 23.7 mmol) in EtOH (73 mL) was added pyridine (3.84 mL, 47.4 mmol) drop wise. The resulting solution was heated at reflux for 3 h. The solvent was evaporated under reduced pressure and the residue was triturated with EtOAc (5×20 mL). The EtOAc fractions were combined and filtered, then evaporated under reduced pressure. The residue was purified by column chromatography (SiO$_2$ hexanes/EtOAc gradient) to give intermediate 36 as a thick colorless liquid (4.7 g, 89%) as the mixture of two geometric isomers: IR (neat) 3027, 2929, 2856, 1736, cm$^{-1}$; $^1$H NMR (CDCl$_3$) δ (ppm) 7.44 (t, J=6.2 Hz, 0.6H), 7.37-7.27 (m, 5H), 6.67 (t, J=5.5 Hz, 0.4H), 5.11 (s, 0.8H), 5.06 (s, 1.2H), 3.67 (s, 3H), 2.37 (m, 0.6H), 2.31 (m, 2H), 2.17 (m, 1.4H), 1.62 (m, 2H), 1.47 (m, 2H), 1.31 (m, 6H); $^{13}$C NMR (CDCl$_3$) δ (ppm) 174.4, 152.6, 151.7, 138.3, 137.8, 128.5 (×2), 128.4, 128.0, 127.9 (×2), 75.8, 75.6, 51.6, 34.2, 29.6, 29.3, 29.1, 29.0, 26.7, 26.3, 25.9, 25.0.

One of the isomers was isolated and characterized, but isomerized soon on standing: $^1$H NMR (CDCl$_3$) δ (ppm) 7.44 (t, J=6.2 Hz, 1H), 7.37-7.27 (m, 5H), 5.06 (s, 2H), 3.67 (s, 3H), 2.30 (t, J=7.4 Hz, 2H), 2.17 (app q, J=6.4 Hz, 2H), 1.62 (m, 2H), 1.47 (m, 2H), 1.31 (br s, 6H).

To a solution of intermediate 36 (4.70 g, 16.1 mmol) and NaCNBH$_3$ (1.12 g, 17.8 mmol) in MeOH (100 mL) was added 2N HCl in MeOH drop wise at room temperature until the solution pH (checked by universal indicator) was adjusted to 3-4, then the solution was stirred for 3 h at room temperature. The solvent was evaporated under reduced pressure to give solid residue, which was dissolved in water (100 mL). 6 N KOH solution was added drop wise to adjust the solution the pH to >9. The aqueous solution was extracted with CH$_2$Cl$_2$ (3×100 mL). The combined organic layers were washed with brine, dried over Na$_2$SO$_4$ and evaporated under reduced pressure. The residue was purified by column chromatography (SiO$_2$ 2% EtOAc in hexanes) to give the hydroxylamine intermediate 37 as a colorless liquid (4.6 g, quant): IR (neat) 3022, 2928, 2854, 1736 cm$^{-1}$; $^1$H NMR (CDCl$_3$) δ (ppm) 7.36-7.27 (m, 5H), 4.71 (s, 2H), 3.67 (s, 3H), 2.92 (t, J=7.0 Hz, 2H), 2.30 (t, J=7.4 Hz, 2H), 1.62 (m, 2H), 1.50 (m, 2H), 1.30 (br s, 8H); $^{13}$C NMR (CDCl$_3$) δ (ppm) 174.5, 138.1, 128.5, 127.9, 76.3, 52.3, 51.6, 34.2, 29.4, 29.3, 29.2, 27.4, 27.2, 25.1; HRMS (FAB) C$_{17}$H$_{28}$NO$_3$ [M+H]$^+$ calcd 294.20691. found 294.20750.

To a solution of intermediate 37 (0.10 g, 0.34 mmol) and DMAP (0.06 g, 0.49 mmol) in CH$_2$Cl$_2$ (4 mL) and pyridine (0.04 mL, 0.49 mmol) was added intermediate 32 (0.06 g, 0.15 mmol) and HOBt (0.05 g, 0.37 mmol) in CH$_2$Cl$_2$ (4 mL). The mixture was cooled to 0° C. and DCC (0.07 g, 0.34 mmol) was added. The mixture was stirred for 1 h at 0° C., then it allowed to warm to room temperature and stirred for additional 20 h. The solvent was evaporated under reduced pressure and the liquid residue was purified by column chromatography (SiO$_2$ hexanes/EtoAc gradient) to give intermediate 38 as a thick colorless oil (0.142 g, 60%): IR (neat) 3269, 3028, 2930, 2857, 1734, 1653 cm$^{-1}$; $^1$H NMR (CDCl$_3$) δ (ppm) 7.77 (d, J=8.2 Hz, 2H), 7.41-7.36 (m, 10H), 7.22 (d, J=8.2 Hz, 2H), 5.65 (s, 1H), 4.82 (s, 4H), 3.66-3.63 (m, 14H), 3.34 (ABq, Δδ=87 Hz, J=9.2 Hz, 4H), 2.67-2.57 (m, 4H), 2.38 (s, 3H), 2.28 (t, J=7.5 Hz, 4H), 1.62-1.57 (m, 8H), 1.28 (m, 16H), 1.09 (s, 3H); $^{13}$C NMR (CDCl$_3$) δ (ppm) 174.4, 172.5, 142.8, 141.0, 134.6, 129.5, 129.3, 129.1, 128.9, 127.0, 76.5, 74.0, 76.1, 58.9, 51.6, 45.6, 34.2, 34.8, 29.3, 29.2, 26.8, 25.0, 21.6, 18.3; HRMS (FAB) C$_{51}$H$_{76}$N$_3$O$_{12}$S [M+H]$^+$ calcd 954.51495. found 954.51690.

To a solution of intermediate 38 (2.03 g, 2.13 mmol) in dry MeOH (45 mL) was added KOH (0.80 g, 14.3 mmol), NH$_2$OTMS (1.22 mL, 9.38 mmol) and the resulting solution was stirred at room temperature for 15 h. Amberlyst-15 (6 g, washed with dry MeOH) was added to the reaction mixture and stirred for additional 1 h. The mixture was filtered and the filtrate was evaporated under reduced pressure to obtain the dibenzyl tetrhydroxamate as a white foamy solid (2.01 g, quant.) which was used without further purification in the next step: IR (neat): 3258, 2927, 2857, 1632, 1454, 1110 cm$^{-1}$; $^1$H NMR (MeOD) δ (ppm) 7.63 (d, J=8.2 Hz, 2H), 7.15 (d, J=8.2 Hz, 2H), 4.76 (s, 4H), 3.55 (app t, J=5.9 Hz, 4H), 3.42 (app t, J=5.8 Hz, 4H), 3.23-3.12 (ABq, 4H overlaps with MeOD), 2.47 (app t, J=5.8 Hz, 4H), 2.24 (s, 3H), 2.13 (t, J=7.4 Hz, 1.4H), 1.94 (t, J=7.3 Hz, 2.3H), 1.48 (m, 8H), 1.17 (m, 16H), 0.95 (s, 3H); HRMS (FAB) C$_{49}$H$_{74}$N$_5$O$_{12}$S [M+H]$^+$ calcd 956.50543. found 956.50500.

To a solution of dibenzyl tetrahydroxamate (2.0 g, 2.1 mmol) in MeOH (100 mL) under argon was added 10% Pd/C (0.22 g). The flask was then evacuated, flushed with H$_2$ (balloons) and the mixture was stirred under H$_2$ at room temperature for 3 h. The reaction mixture was filtered and the filtrate was evaporated under reduced pressure to give ligand 12 as a foamy solid (1.3 g, 81%): IR (neat) 3500-2600 (broad), 2927, 2856, 1613 cm$^{-1}$; $^1$H NMR (MeOD) δ 7.58 (d, J=8.0 Hz, 2H), 7.14 (d, J=8.0 Hz, 2H), 3.44-3.36 (m, 8H), 3.16-3.09 (m, 4H, overlaps with CD$_3$OD), 2.47 (t, J=5.7 Hz, 4H), 2.21 (s, 3H), 1.89 (t, J=7.2 Hz, 4H), 1.41 (br. S, 8H), 1.12 (br. S, 16H), 0.89 (s, 3H); $^{13}$C NMR (MeOD) δ 173.6, 173.1, 144.3, 142.5, 130.5, 128.0, 74.9, 68.0, 60.1, 52.1, 34.9, 33.8, 30.3, 30.1, 27.8, 27.7, 26.8, 26.1, 21.6, 19.4; HRMS (FAB) $C_{35}H_{62}N_5O_{12}S$ [M+H]$^+$ calcd 776.41150. found 776.41130.

Example 25

Preparation of Urea-Linked Tris Hydroxamic Acid Resin 6 phase was separated. The aqueous layer was extracted twice with $CH_2Cl_2$, combined organic extracts dried and concentrated to afford intermediate 39 (12.2 g, 93%) as a clear, dark oil: IR(ATR) 2955, 2878, 2245 (NCO), 1733 (C=O), 1437; $^1$H NMR (CDCl$_3$, 300 MHz) δ 2.52 (t, 3H, 6.3 Hz), 3.39 (s, 6H), 3.62 (s, 9H), 3.68 (t, 3H, 6.3 Hz); $^{13}$C NMR (CDCl$_3$, 75 MHz) δ 34.7, 51.6, 63.7, 67.0, 71.1, 127.2 (CNO), 171.8.

To 2 g (4.4 mmol) of aminomethyl resin (Aldrich 564095; Macroporous 30-60 mesh, 2.2 meq/g) was added 10 mL of $CH_2Cl_2$ followed by 2.3 mL of diisopropylethyl amine (DIEA). The mixture was treated with 5.3 g (13.2 mmol) of

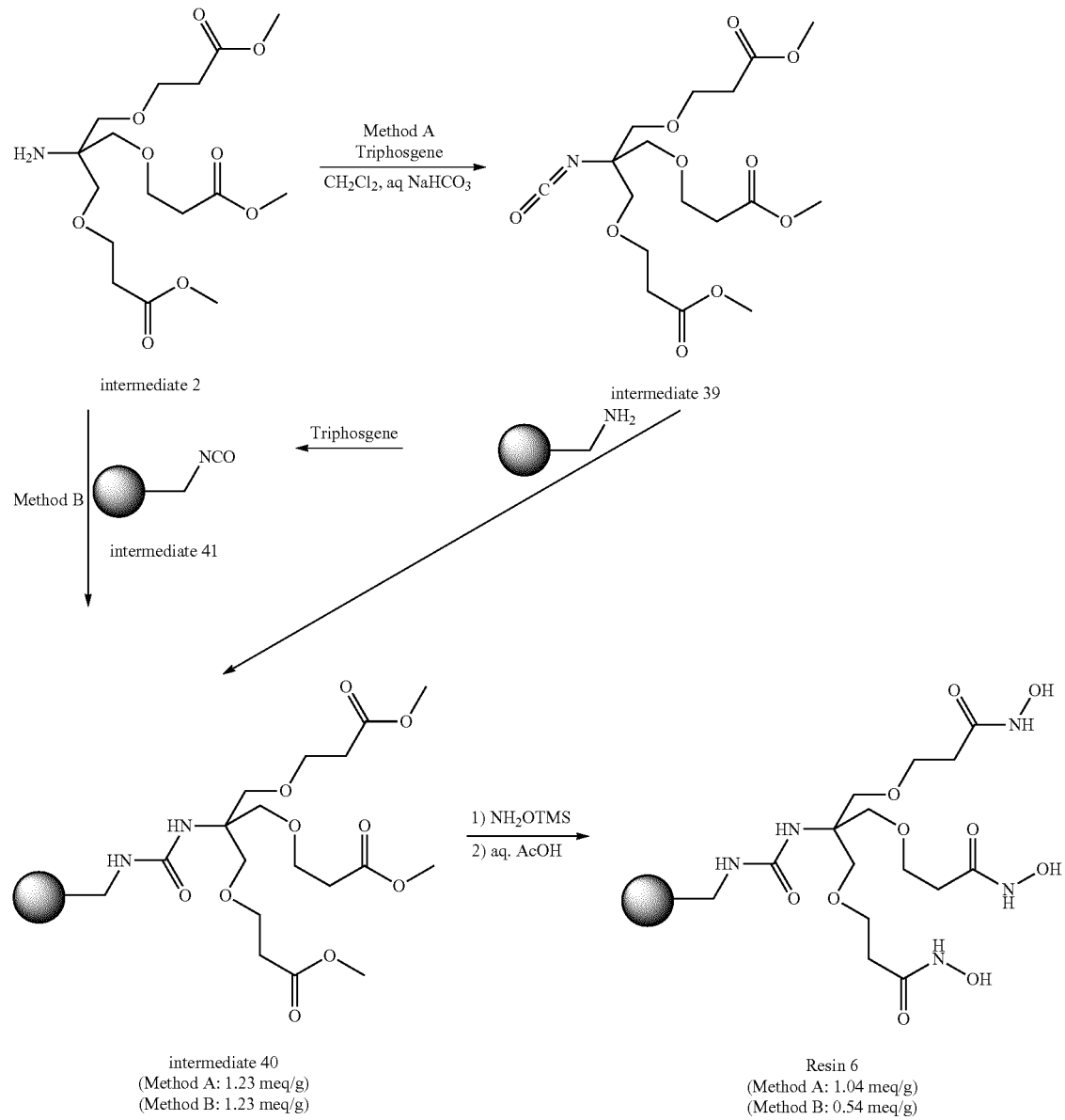

Scheme 42

Method A—Amine resin and TRIS Isocyanate Route

To 12.26 g (32.3 mmol) of the free amine intermediate 2 in 130 mL of $CH_2Cl_2$ was added 130 mL of saturated NaHCO$_3$. The stirred mixture was treated PORTIONWISE with 3.2 g (10.8 mmol) of triphosgene. This reaction is fast and results in a lot of gas formation. After stirring for 15 min, the organic intermediate 39 and allowed to agitate at rt overnight. The resin was subsequently filtered and washed three times each with $CH_2Cl_2$, MeOH, $H_2O$, saturated NaHCO$_3$, $H_2O$, MeOH and $Et_2O$. After filtration the resin was dried under reduced pressure overnight at rt to afford 3.11 g of a light tan resin intermediate 40 IR(ATR) 3382 (br), 3023, 2924, 1737

(C=O), 1680; Elemental Analysis: C, 74.31; H, 7.53; N, 3.44; EA shows loading of 1.23 meq/g based on N analysis.

A suspension of 2.74 g (3.37 mmol) of urea-triester resin intermediate 40 in 17 mL of MeOH was prepared in the 60 mL peptide reactor. The mixture was treated with 3.02 mL of $NH_2OTMS$ followed by 1.34 g of KOH in 10 mL of MeOH. The mixture was allowed to agitate by rocking overnight. The mixture was filtered and washed three times each with MeOH, $H_2O$, MeOH and $H_2O$. The resin was treated with 10% aq. acetic acid and allowed to agitate for one hour. The resin was filtered, washed three times each with MeOH, $H_2O$, $Et_2O$ and dried under reduced pressure to give 2.85 g of the trihydroxamic acid resin 6 IR(ATR) 3205, 2919, 1636, 1550. Elemental Analysis: C, 66.02; H, 7.08; N, 7.28; EA shows loading of 1.04 meq/g based on N analysis.

Method B—Isocyanate Resin and Tris Amine Route

To 2 g (4.4 mmol) of aminomethyl resin (Aldrich 564095; macroporous 30-60 mesh, 2.2 meq/g) was added 10 mL of $CH_2Cl_2$ followed by 770 uL of DIEA and 1.3 g (4.4 mmol) of triphosgene. The mixture was allowed to rock in a peptide reactor for 15 min and subsequently filtered and washed with $CH_2Cl_2$. The resin was suspended in 10 mL treated with 2.31 mL of DIEA and 5.0 g (13.2 mmol) of aminetriester intermediate 2 and allowed to rock overnight. Filtration followed by washing three times each with $CH_2Cl_2$, MeOH, $H_2O$, satr $NaHCO_3$, $H_2O$, MeOH and $Et_2O$ afforded intermediate 40. The product was dried in vacuo at rt overnight to give 2.35 g of an off-white resin: IR(ATR) 3300 (br, weak), 3025, 2923, 2260 (very weak, residual isocyanate), 1738, 1679, 1601. Elemental Analysis: C, 81.06; H, 7.62; N, 3.41; EA shows loading of 1.23 meq/g based on N analysis.

A suspension of 2.2 g (2.7 mmol) of urea-triester resin intermediate 40 in 10 mL of MeOH was prepared in the 60 mL peptide reactor. The mixture was treated with 1.2 mL of $NH_2OTMS$ followed by 0.56 g of KOH in 8 mL of MeOH. The mixture was allowed to rock overnight. The mixture was filtered and washed three times each with MeOH and $H_2O$. The resin was treated with 10% aq. acetic acid and allowed to rock for one hour. The resin was filtered, washed three times each with $H_2O$, MeOH, $Et_2O$ and dried under reduced pressure to give 2.2 g of the trihydroxamic acid resin 6: IR(ATR) 3311, 3023, 2920, 1651, 1600. Elemental Analysis: C, 80.46; H, 7.51; N, 3.75; Elemental analysis shows loading of 0.54 meq/g based on N analysis.

Example 26

Preparation of Polyalkoxy Tether-Linked Tris Hydroxamic Acid Resin 7

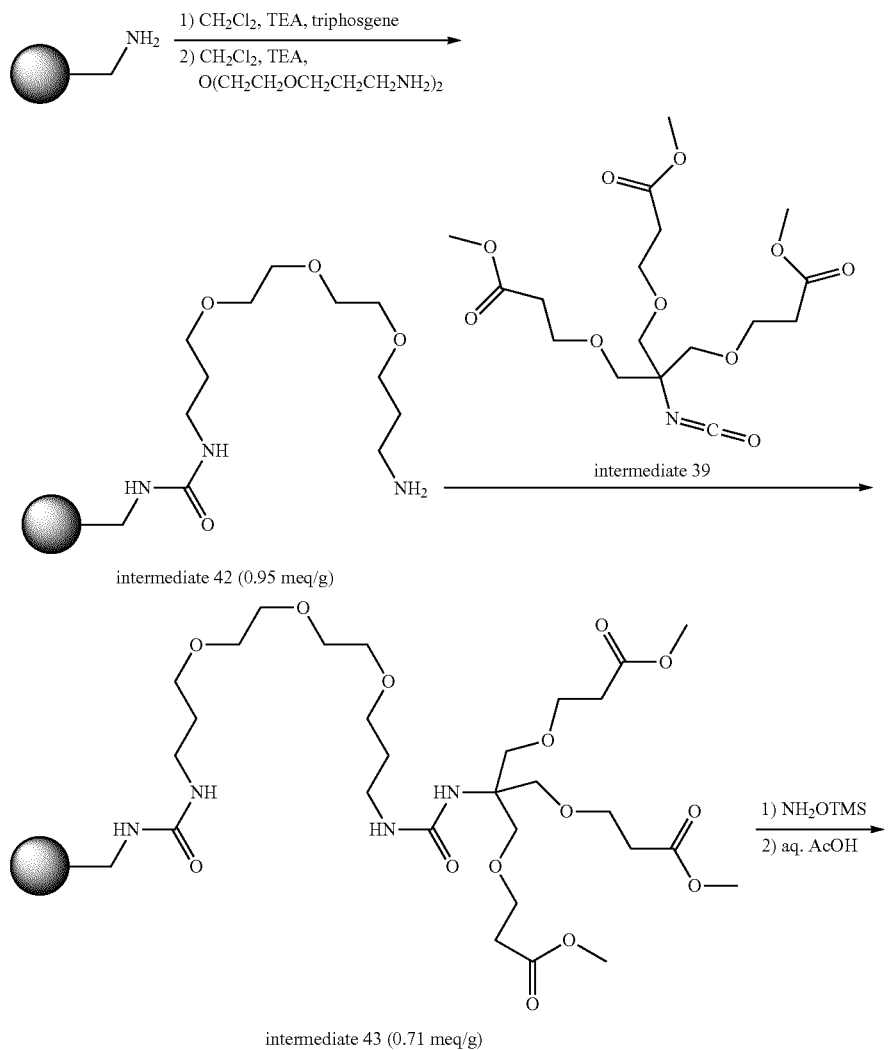

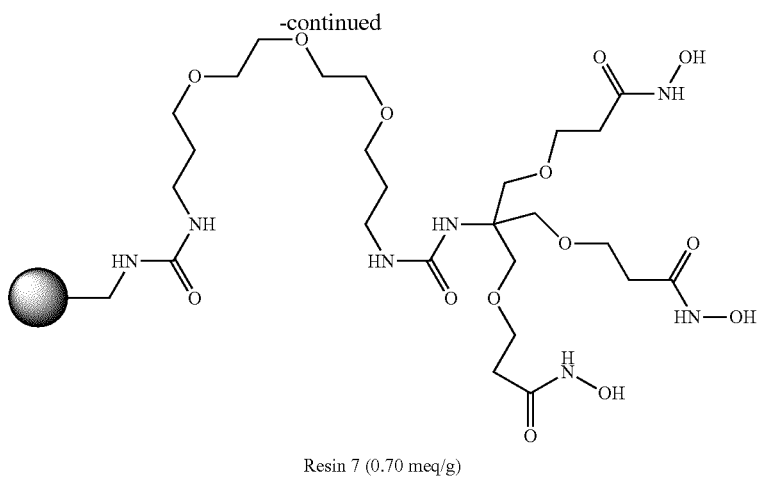

Resin 7 (0.70 meq/g)

To 5 g (11 mmol) of aminomethyl resin (Sigma-Aldrich cat#564095; 2.2 meq/g) in 25 mL CH$_2$Cl$_2$ in the 60 mL peptide reactor was added 1.53 mL of triethylamine. The mixture was treated portionwise with 3.26 g (11 mmol) of triphosgene. After 15 min the mixture was filtered and washed three times with CH$_2$Cl$_2$. The resin was suspended in 25 mL CH$_2$Cl$_2$ and treated with 4.6 mL TEA and 7.23 mL of 4,7,10-trioxa-1,13-tridecanediamine. After rocking for two days, the mixture was filtered and washed three times each with CH$_2$Cl$_2$, MeOH, H$_2$O, MeOH, Et$_2$O and allowed to dry under a stream of N$_2$ for 1 h. The resin was dried overnight in vacuo at rt to afford 6.177 g of an off-white resin intermediate 42. IR (ATR) 3560 (br, weak), 2920, 2880, 1655. Elemental Analysis: C, 80.14; H, 8.18; N, 4.01; EA shows loading of 0.95 meq/g based on N analysis.

To 6.14 g of resin intermediate 42 (5.8 mmol) was added 30 mL of CH$_2$Cl$_2$ followed by 2.3 mL of diisopropylethylamine (DIEA). The mixture was treated with 5.3 g of isocyanate intermediate 39 and allowed to agitate by rocking for 2 days at rt. The resin was filtered and washed three times each with CH$_2$Cl$_2$, MeOH, H$_2$O, satr NaHCO$_3$, H$_2$O, MeOH and Et$_2$O. After filtration the resin was dried in vacuo overnight at rt to afford 5.5 g of a light tan resin intermediate 43: IR(ATR) 3322 (br), 3023, 2920, 2865, 1736 (C=O), 1685, 1655. Elemental Analysis: C, 78.52; H, 7.84; N, 3.99; EA shows loading of 0.71 meq/g based on N analysis.

A suspension of 5.5 g of triester resin intermediate 43 (3.8 mmol) in 15 mL of MeOH was prepared in a 60 mL peptide reactor. The mixture was treated with 4.2 mL of NH$_2$OTMS followed by a solution of 1.92 g of KOH in 20 mL of MeOH. The mixture was allowed to rock overnight at rt. The mixture was subsequently filtered and washed three times each with MeOH and H$_2$O. The resin was treated with 10% aq. acetic acid and allowed to rock for one hour. The resin was filtered, washed three times each with H$_2$O, MeOH, Et$_2$O and dried in vacuo at rt to give 5.96 g of the trihydroxamic acid resin 7: IR(ATR) 3200, 2915, 1670, 1650, 1552. Elemental Analysis: C, 76.24; H, 7.77; N, 4.68; EA shows loading of 0.67 meq/g based on N analysis.

Example 27

A Urea Linked Unsymmetrical Resin 8

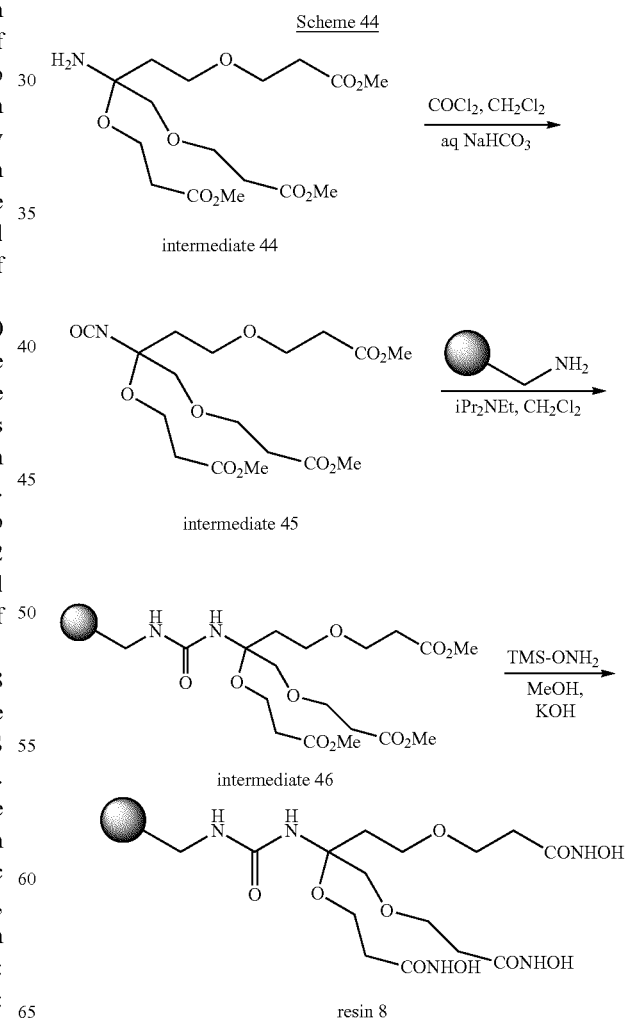

resin 8

To a vigorously stirred solution of amine triester intermediate 44 (12.0 g, 30.5 mmol) in $CH_2Cl_2$ (100 mL) and saturated $NaHCO_3$ (100 mL) was added triphosgene (3.08 g, 36.0 mmol) in small portions. Once the addition was complete, the mixture was stirred for an additional 15 min., then the layers were separated and the aqueous layer was extracted with $CH_2Cl_2$ (2×100 mL). The combined organic extracts were dried over $Na_2SO_4$, evaporated under reduced pressure, and the residue was purified by column chromatography ($SiO_2$, hexanes/EtOAc gradient) to give the isocyanate intermediate 45 as a colorless oil (5.14 g, 41%): IR (neat) 2957, 2874, 2244, 1733 cm$^{-1}$; $^1$H NMR (300 MHz, CDCl$_3$) δ 3.70 (t, J=6.3 Hz, 4H), 3.64 (s, 9H), 3.63 (t, J=6.3 Hz, 2H), 3.50 (t, J=6.3 Hz, 2H), 3.39 (s, 4H), 2.54 (t, J=6.2 Hz, 4H), 2.52 (t, J=6.2 Hz, 2H), 1.72 (t, J=6.4 Hz, 2H); $^{13}$C NMR (300 MHz, CDCl$_3$) δ 172.1, 171.9, 126.6, 73.4, 66.8, 66.7, 66.2, 62.7, 51.8, 51.7, 34.9, 34.8, 33.8; HRMS (FAB) calcd for $C_{18}H_{30}NO_{10}$ [M+H]$^+$: 420.1870. Found 420.1885.

To a suspension of aminomethyl resin (Aldrich 564095, macroporous 30-60 mesh) (1.84 g, 2.2 meq/g, 4.05 mmol of —NH$_2$), in $CH_2Cl_2$ (15 mL) was added diisopropylethyl amine (2.12 ml, 12.2 mmol) followed by the isocyanate intermediate 45 (5.10 g, 12.2 mmol). The suspension was shaken using orbital shaker overnight at room temperature. The resin was filtered and washed 3 times each with $CH_2Cl_2$, MeOH, $H_2O$, saturated $NaHCO_3$, $H_2O$, MeOH and $Et_2O$. It was dried under reduced pressure to obtain pale yellow resin intermediate 46 (2.86 g). Wt. added to the resin=1.02 g; IR (ATR): 3393, 3026, 2912, 2869, 1736 (C=O), 1673 cm$^{-1}$; Elemental analysis C=75.50%; H=7.59%; N=3.35%; loading=0.87 meq/g (based on % N); % C indicates 76% conversion of available NH$_2$ groups of the resin.

A suspension of the urea triester resin intermediate 46 (2.68 g, 1.14 meq/g—maximum loading, 3.06 mmol) in MeOH (20 mL) was shaken for 15 minutes. A solution of KOH (1.54 g, 27.59 mmol) in MeOH (5 mL) was added followed by NH$_2$OTMS (3.37 mL, 27.6 mmol) and the mixture was shaken for 20 h using orbital shaker. The resin was filtered and washed 3 times each with MeOH, H$_2$O. The resin was then suspended in 10% aqueous AcOH (20 mL) and for shaken for 30 minutes. The resin was filtered and washed 3 times with 10% aqueous $CH_3CO_2H$, $H_2O$, MeOH and $Et_2O$ and dried under reduced pressure to give a light yellow colored resin 8 (2.7 g). Wt. gained by the resin=0.02 g; IR (ATR): 3221, 3025, 2920, 1641 (C=O hydroxamate, sharp), 1551 cm$^{-1}$; Elemental analysis C=71.48%; H=7.36%; N=4.65%; loading=0.58 meq/g (based on % N).

Example 28

Scheme 45

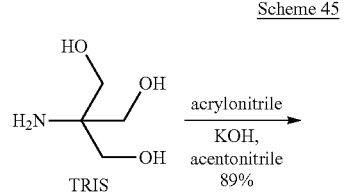

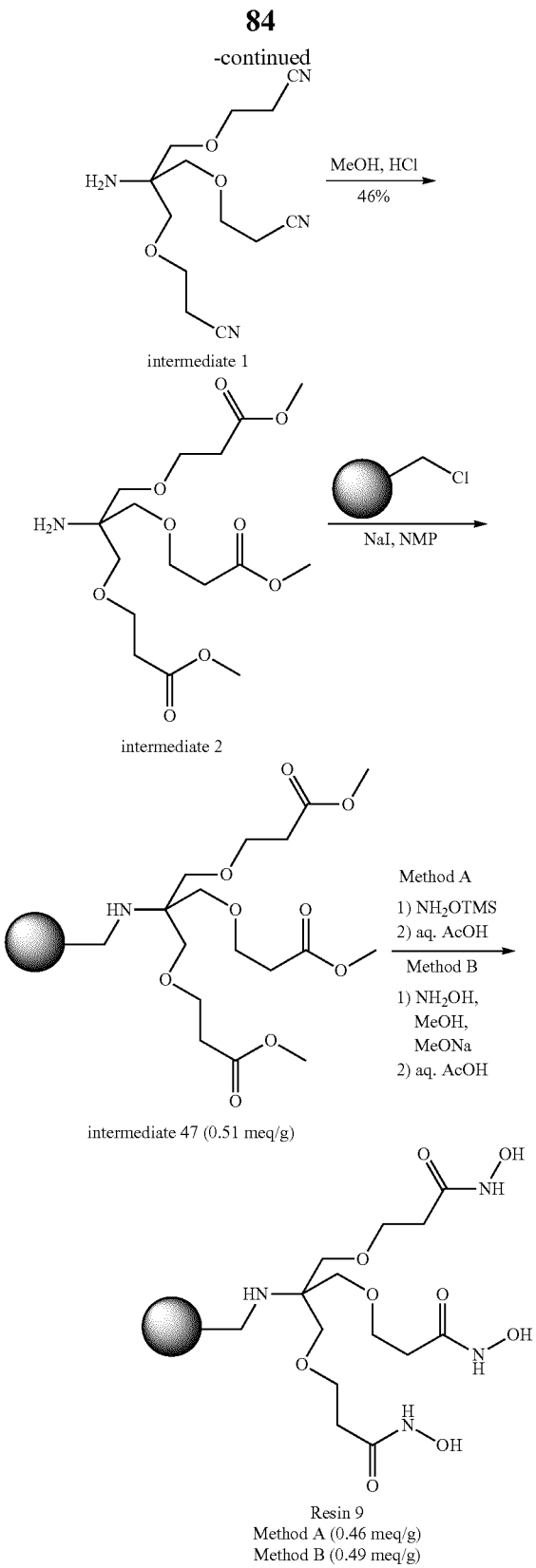

Tris[2-(cyanoethoxy)methyl]methylamine (Intermediate 1) by an Improved Method

A stirred suspension of tris-(hydroxymethyl)aminomethane (127.0 g) in acetonitrile (500 mL) in a 2 L round bottom flask equipped with an overhead stirrer was treated with KOH (5.0 g). Acrylonitrile (207 mL) was added to the stirred suspension over a few minutes. After 1 h, an exotherm was observed to 36° C. After 3 h, the mixture was a homogeneous, slightly orange solution and showed complete conversion based on $^1$H NMR analysis. After a total of 4 h, the mixture was concentrated under reduced pressure to afford intermediate 1 (237.8 g, 89%) as a light tan oil. IR(neat) 3504, 3288, 2857, 2250 (CN); $\eta_D^{23}$=1.4687 $^1$H NMR (CDCl$_3$, 300 MHz) δ1.45 (brs, 2H), 2.53 (t, 6.0 Hz, 6H), 3.34 (s, 6H), 3.59 (t, 6.0 Hz, 6H); $^{13}$C NMR (CDCl$_3$, 75 MHz) δ18.8, 56.0, 65.7, 72.5, 188.1. This compound has been previously prepared, however the yield appears to be improved with acetonitrile solvent.

A 10 mL oven dried peptide reactor was charged with Merrifield resin (2.0 g) (Marcroporous, 100-200 mesh, 150-75 um, 1.2 mmol/g, SigmaAldrich 564087, Lot #05629MC, washed and dried) and anhydrous NaI (400 mg). The mixture was suspended in a solution of intermediate 2 (2.93 g) in of anhydrous NMP (12 mL) and agitated for 7 days at rt. The mixture was sampled at regular intervals and the reaction progress monitored by IR (ATR). After a total of 7 days the reaction was complete. The product was collected by filtration and washed sequentially three times each with DMA, H$_2$O, MeOH and Et$_2$O to give a light, tan resin intermediate 47: IR(ATR) 3026, 2921, 1739 (C=O), 1602; Elemental Analysis: C, 83.03; H, 7.59; N, 0.72; EA shows loading of 0.51 meq/g (53% conversion of benzylchloride groups). The resin was kept in the peptide reactor and used directly in the next step.

Preparation of Trishydroxamic Acid Resin 9 using Method A.

A suspension of the ester resin intermediate 47 in anhydrous MeOH (5 mL) was treated with NH$_2$OTMS (2.42 mL), followed by a solution of KOH (1.11 g) in anhydrous MeOH (5 mL). The mixture was agitated overnight, then the resin was washed three times each with MeOH and H$_2$O, treated with 10% aq. AcOH and agitated for 1 h. The mixture was filtered and treated a 2nd time with 10% AcOH for 30 min. The resin was filtered, washed three times each with MeOH, H$_7$O, Et$_2$O and dried under reduced pressure to give of the trihydroxamic acid resin 9 (1.84 g): IR(ATR) 3210, 3026, 2921, 1652, 1602, 1493; Elemental Analysis: C, 80.33; H, 7.46; N, 2.55; EA shows loading of 0.46 meq/g.

Preparation of Trishydroxamic Acid Resin 9 using Method B.

A mixture of 900 mg of hydroxylamine hydrochloride in 30 mL of 0.5 M sodium methoxide in methanol was stirred at rt for 15 min. The mixture was filtered to remove NaCl salts and added directly to 2.0 g of triester resin intermediate 47 (1.24 mmol) in a flask equipped with an overhead stirrer, heating mantle and kept under nitrogen. The stirred mixture was heated to 45° C. and allowed to stir for 3 days. After filtration the resin was washed three times each with methanol, 10% aq. acetic acid, H$_7$O, methanol, and ethyl ether. The resin was dried in vacuo overnight to afford an amber resin 9: IR(ATR) 3210, 2921, 1652, 1602. Elemental Analysis: C, 78.95; H, 7.43; N, 2.74; EA shows loading of 0.49 meq/g based on N analysis.

Example 29

Resin Linked Tetrahydroxamic Acid

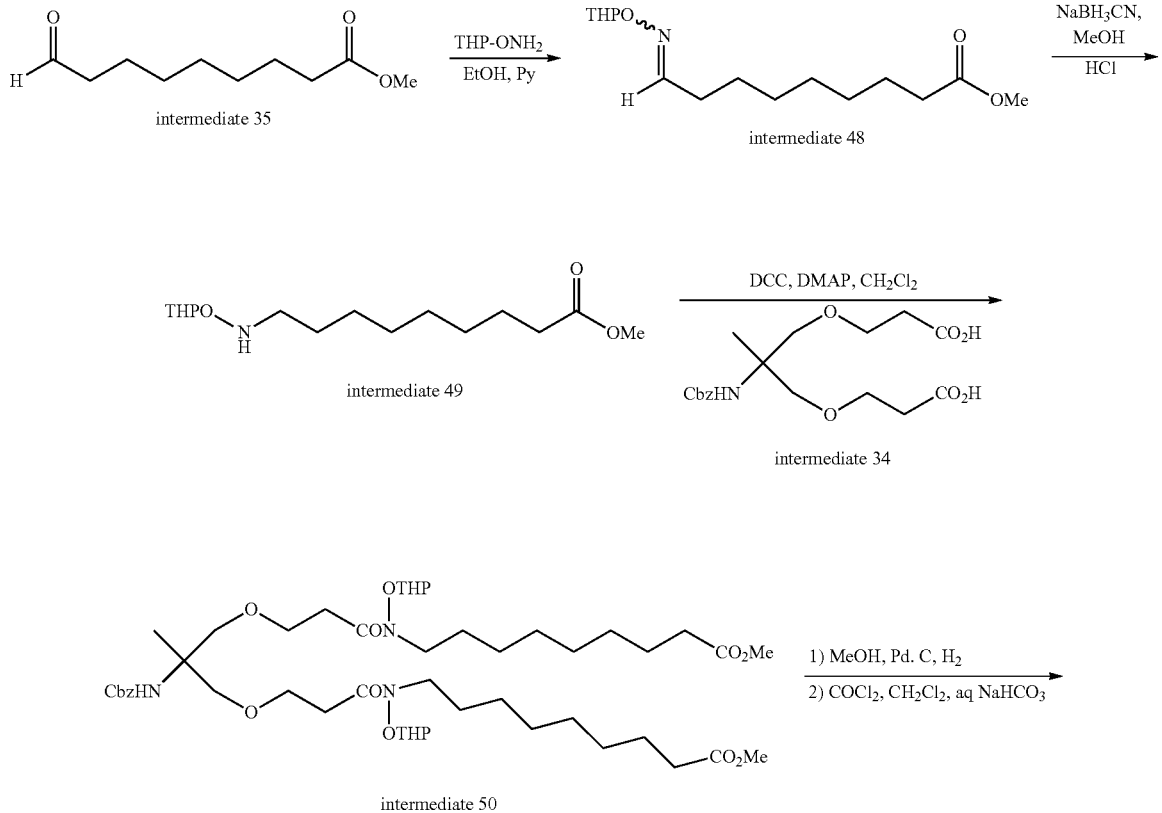

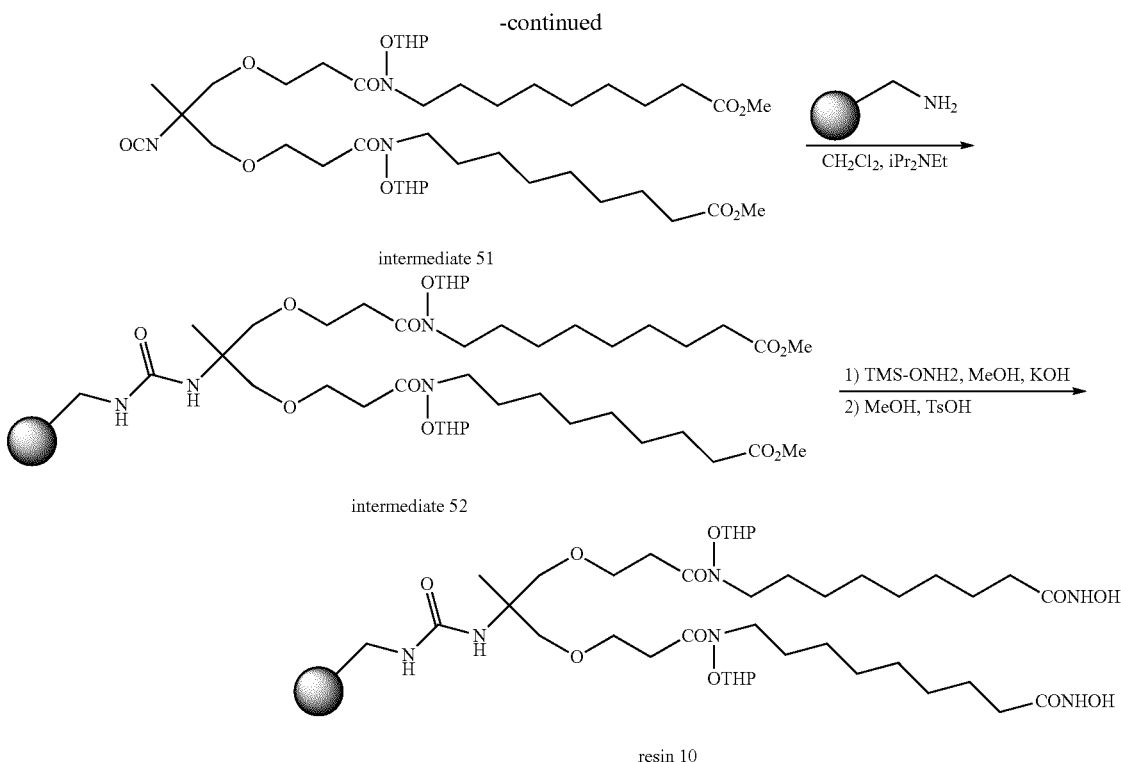

intermediate 51 intermediate 52 resin 10

To a solution of aldehyde intermediate 35 (Kai, K.; Takeuchi, J.; Kataoka, T.; Yokoyama, M.; Watanabe, N. *Tetrahedron* 2008, 64, 6760) (2.89 g, 15.5 mmol) and O-(tetrahydro-2H-pyran-2-yl)hydroxylamine (2.0 g, 17.1 mmol) in EtOH (62 mL) at room temperature was added pyridine (1.88 mL, 23.3 mmol) drop wise. The resulting solution was heated at reflux for 4 h. Solvent was evaporated under reduced pressure and the residue was dissolved in $CH_2Cl_2$ (100 mL) and washed with water (2×100 mL). The aqueous layer was re-extracted with $CH_2Cl_2$ (2×100 mL). The combined organic layers were dried over $Na_2SO_4$ and evaporated reduced pressure. The crude product was purified by column chromatography ($SiO_2$ hexanes) to give the oxime intermediate 48 as a colorless liquid (3.70 g, 84%) and as a mixture of geometric isomers: IR (neat) 2933, 2856, 1736 cm$^{-1}$; $^1$H NMR (CDCl$_3$) δ (ppm) 7.42 (t, J=6.3 Hz, 0.4H), 7.71 (t, J=5.5 Hz, 0.6H), 5.19 (m, 1.2H), 5.15 (m, 0.8H), 3.89-3.84 (m, 1H), 3.62 (s, 3H), 3.59-3.53 (m, 1H), 2.35 (m, 1.5H), 2.26 (m, 2H), 2.18 (m, 0.5H), 1.90-1.40 (m, 10H), 1.29-1.26 (m, 6H); $^{13}$C NMR (CDCl$_3$) δ (ppm) 174.2, 153.5, 152.9, 100.6, 100.5, 63.2, 63.1, 51.4, 34.0, 29.5, 29.1, 29.0, 28.9 (×3), 26.6, 26.1, 25.8, 25.2 (×2), 24.9, 20.1, 20.0; HRMS (FAB) $C_{15}H_{28}NO_4$ [M+H]$^+$ calcd 286.20184. found 286.20110.

To a solution of intermediate 48 (3.60 g, 12.31 mmol) and NaCNBH$_3$ (0.95 g, 15.1 mmol) in MeOH (100 mL) was added 2N HCl in MeOH drop wise until the solution pH was adjusted to 4 (pH was never allowed to go down from 4). The mixture was stirred for 3 h at rt. The solvent was evaporated under reduced pressure to give solid residue which was dissolved in water (100 mL) and then 6 N KOH solution was added drop wise to adjust the solution pH to >9. The aqueous mixture was extracted with $CH_2Cl_2$ (3×100 mL). The organic layers were combined and washed with brine, dried over $Na_2SO_4$ and evaporated under reduced pressure. The crude product was purified by column chromatography ($SiO_2$ hexanes/EtOAc gradient) to give intermediate 49 as a colorless liquid (2.80 g, 78%): IR (ATR, neat) 2931, 2854, 1736 cm$^{-1}$; $^1$H NMR (CDCl$_3$) δ (ppm) 5.53 (s, 1H), 4.73-4.71 (m, 1H), 3.89-3.82 (m, 1H), 3.59 (s, 3H), 3.53-3.46 (m, 1H), 2.96-2.82 (m, 2H), 2.23 (t, J=7.4 Hz, 2H), 1.75-1.39 (m, 10H), 1.25 (m, 8H); $^{13}$C NMR (CDCl$_3$) δ (ppm) 174.2, 101.4, 63.1, 52.2, 51.4, 34.0, 29.3, 29.2, 29.1, 29.0, 27.2, 27.1, 25.3, 24.9, 20.2; HRMS (FAB) $C_{15}H_{30}NO_4$ [M+H]$^+$ calcd 288.21747. found 288.21780.

To a stirred solution of intermediate 49 (2.30 g, 8.00 mmol) and DMAP (1.33 g, 10.9 mmol) in $CH_2Cl_2$ (70 mL) and pyridine (0.88 mL, 10.9 mmol) was added intermediate 34 (1.39 g, 3.63 mmol) in $CH_2Cl_2$ and the mixture was cooled to 0° C. DCC (1.65 g, 8.00 mmol) was added and the mixture was stirred for 1 h at 0° C. The mixture was then allowed to warm to room temperature and was stirred for additional 15 h. The solvent was concentrated under reduced pressure, filtered and washed with $CH_2Cl_2$. The filtrate was evaporated under reduced pressure and the residue was purified by column chromatography ($SiO_2$ hexanes/EtOAc gradient) to give intermediate 50 as a colorless oil (2.50 g, 76%): IR (neat) 3329, 2930, 2856, 1732, 1655 cm$^{-1}$; $^1$H NMR (CDCl$_3$) δ (ppm) 7.33-7.24 (m, 5H), 5.51 (s, 1H), 4.99 (s, 2H), 4.87 (s, 2H), 3.92-3.87 (m, 2H), 3.78-3.68 (m, 6H), 3.61 (s, 6H), 3.58-3.37 (m, 8H), 2.65-2.60 (m, 4H), 2.25 (t, J=7.5 Hz, 4H), 1.76-1.54 (m, 20H), 1.29 (s, 3H), 1.24 (br s, 16H); $^{13}$C NMR (CDCl$_3$) δ (ppm) 174.1, 172.7, 155.1, 136.7, 136.6, 128.3 (×2), 127.8, 127.7, 104.3, 77.4, 73.2, 73.1, 67.9, 67.0, 65.8, 63.4, 55.7, 55.6, 51.3, 50.1, 48.6, 48.1, 35.5, 33.9, 32.9, 32.5, 30.6, 29.0 (×2), 28.9, 28.8 (×2), 26.6, 26.5, 26.0, 25.6, 25.1, 19.8, 19.1; HRMS (FAB) $C_{48}H_{79}N_3O_{14}Na$ [M+Na]$^+$ calcd 944.5460. found 944.5488.

To a solution of intermediate 50 (2.50 g, 2.70 mmol) in MeOH (200 mL) under argon was added 10% Pd/C (0.275 g). The flask was evacuated then flushed with H$_2$ (balloons) and resulting the mixture was stirred under $H_2$ at room temperature until TLC analysis (75% EtOAc in hexanes) indicated that the starting material was consumed. The reaction flask was then purged with argon and filtered. The filtrate was evaporated under reduced pressure to give the amine as thick oil (2.1 g, 100%) which was used directly in the next step. To a stirred biphasic mixture of the amine (2.1 g, 2.7 mmol) in $CH_2Cl_2$ (30 mL) and saturated $NaHCO_3$ (30 mL) was added triphosgene (0.26 g, 0.89 mmol) in small portions. After 20 min after the addition of triphosgene the layers were separated and the aqueous layer was washed with $CH_2Cl_2$ (2×30 mL). The combined organic layers were dried over $Na_2SO_4$ and evaporated under reduced pressure to give the isocyanate intermediate 51 as a thick colorless oil product (1.7 g, 78%) which was found to be pure enough to use in the next step without further purification. IR (neat) 2932, 2856, 2241, 1736, 1655 $cm^{-1}$; $^1H$ NMR ($CDCl_3$) δ (ppm) 4.89 (br s, 2H), 3.96-3.89 (m, 2H), 3.81-3.72 (m, 6H), 3.62 (s, 6H), 3.60-3.53 (m, 4H), 3.41-3.32 (m, 4H), 2.68-2.61 (m, 4H), 2.26 (t, J=7.4 Hz, 4H), 1.78-1.57 (m, 20H), 1.26 (br s, 16H), 1.18 (s, 3H); $^{13}C$ NMR ($CDCl_3$) δ (ppm) 174.3, 172.7, 126.8, 104.5, 77.4, 75.3, 75.2, 75.1, 68.2, 67.3, 63.6, 61.2, 61.1, 61.0, 55.0, 51.5, 50.2, 48.3, 35.7, 34.1, 33.1, 32.6, 30.8, 29.5, 29.2, 29.1, 26.9, 26.8, 26.2, 25.5, 25.4, 22.5, 19.8; HRMS (FAB) $C_{41}H_{71}N_3O_{13}Na$ $[M+Na]^+$ calcd 836.48846. found 836.48570.

To a suspension of the aminomethyl resin (1.1 g, 2.2 meq/g, 2.42 mmol of —$NH_2$, Aldrich 564095, macroporous 30-60 mesh) in $CH_2Cl_2$ (17 mL) and diisopropyl ethyl amine (2.66 mL, 15.3 mmol) was added the isocyanate intermediate 51 (5.0 g, 6.10 mmol), and the resulting mixture was shaken on orbital shaker for 24 h at room temperature. The resin was filtered and washed 3 times each with $CH_2CH_2$, MeOH, $H_2O$, saturated $NaHCO_3$, $H_2O$, MeOH and $Et_2O$. It was then dried under reduced pressure to obtain light colored resin intermediate 52 (1.51 g). Wt. added to the resin=0.41 g. IR (ATR): 3377, 3022, 2924, 2848, 1734 (C=O ester), 1655 (C=O hydroxamate $cm^{-1}$. Elemental analysis C, 81.23%; H, 7.96%; N, 3.67%; loading=0.28 meq/g (based on % N). Change in % C indicates 43% conversion of available $NH_2$ groups of the resin.

To a suspension of the resin intermediate 52 (1.51 g, 0.30 meq/g, 0.45 mmol) in MeOH (10 mL) was added KOH (0.15 g, 2.7 mmol) and $NH_2OTMS$ (0.33 mL, 2.7 mmol) and the mixture was shaken for 20 h on an orbital shaker. The resin was isolated by filtration and washed 3 times with MeOH. The resin was re-suspended in a solution of $TsOH.H_2O$ (0.52 g, 2.7 mmol) in MeOH (10 mL) and shaken for 3 h. The resin was isolated by filtration and washed 3 times each with MeOH, $H_2O$, MeOH and $Et_2O$ and dried under reduced pressure to give the product as pale yellow colored resin 10 (1.73 g). Wt. gained by the resin=0.22 g. IR (ATR): 3382 (br), 3500-2500 (br), 3024, 2922, 2854, 1646 (C=O hydroxamate) $cm^{-1}$. Elemental analysis C, 75.74%; H, 7.51%; N, 3.68%. Loading=0.19 meq/g (based on % N).

Example 30

Binding of Al to resin 9

The compounds and compositions of the present invention are useful in a method of removing a trivalent metal ion such as $Al^{3+}$ from an aqueous solution. This is accomplished by treating the aqueous solution with the invention, which consists of a resin to which the chelating agent is attached by a covalent bond to form a chelating resin.

To demonstrate the ability of resin 9 to bind $Al^{3+}$, a 240 mg portion of the resin was suspended in three different aqueous solutions: (1) an aqueous solution buffered at pH 6.06 by 0.1 M MES (4-morpholineethanesulfonic acid); (2) a solution of gluconate that had been adjusted to pH 6.42 by the addition of tetramethylammonium hydroxide; and (3) a commercial sample of calcium(gluconate)$_2$, which had a pH of 6.07. Each solution was stirred by a magnetic overhead stirrer to keep the resin suspended in solution with significant mechanical damage as might result from use of a stir bar.

At periodic times, the stirring was stopped for 1-2 minutes to let the resin settle, and a 100 µL aliquot was removed from the sample solution. Five µL of concentrated, metal-free nitric acid was added immediately to each aliquot removed to stabilize the $Al^{3+}$ in solution. Samples were collected and subsequently analyzed by inductively coupled plasma-mass spectrometry to determine the Al concentration. FIG. 6 shows plots of the fraction of original Al concentration remaining in the extracted solutions as a function of the extraction time.

The pH of the sample solutions was measured before and immediately after the completion of the extraction experiment. The addition of the resin and the extraction produce essentially no change in the pH of any of the solutions tested.

In the extraction of $Al^{3+}$ from the MES buffer, the only competition to binding to the chelating resin is the hydrolysis of $Al^{3+}$ to a mixture of Al-hydroxide complexes. FIG. 6 shows that the concentration of $Al^{3+}$ decreases to ~0. In the case of both gluconate and calcium gluconate solutions, chelation of $Al^{3+}$ by gluconate is competitive with the binding of $Al^{3+}$ to the resin. Nevertheless, resin 9 removes approximately 90% of the Al from both of these solutions.

FIG. 7 shows the extraction of three solutions of commercial calcium(gluconate)$_2$. The figure includes data from two duplicate extractions of the calcium(gluconate)$_2$ by 240 mg portions of resin 9. The resin removes ~90% of the total Al. The rate of Al removal from the solution can be fit to a single-exponential function to give an apparent first-order rate constant for Al removal of 4.2 $hr^{-1}$, which corresponds to a half-life for Al removal of only 10 minutes. The solid line in FIG. 7 is the least squares fit of one of the two data sets to the single-exponential function.

For the purpose of comparison, another aliquot of the same commercial calcium(gluconate)$_2$ solution was extracted with the commercial chelating resin Chelex®. This resin consists of polystyrene beads to which the chelating agent iminodiacetic acid has been linked by covalent bonds. This resin is widely used in a variety of applications to remove metal ions from solution. FIG. 7 shows that the Chelex resin is not able to remove any significant fraction of $Al^{3+}$ from the calcium (gluconate)$_2$ solution. This poor extraction reflects the avidity with which gluconate binds $Al^{3+}$, and demonstrates a strong chelating agent is required to compete with gluconate to remove $Al^{3+}$ from the solution.

The Al-binding constants for gluconate have been reported (R. J. Motekaitis and A. E. Martell, Inorg. Chem. 1984, 23: 18-23). Given these binding constants for Al-gluconate, the percentage of Al remaining in a gluconate solution in equilibrium with resin-9 can be used to estimate the effective Al binding constant of the trihydroxamate chelating agent covalently bound to the resin. The removal of 90% of the Al corresponds to an $Al^{3+}$—resin binding constant of log K=20.6.

The immobilized chelating agents described in this document may be used in a number of difference devices. FIGS. 8a-8d disclose three different embodiments of cartridge 10 filled with any of the immobilized chelating agents described in this document. Each cartridge 10 contains a sealed body 12 having a first Luer Lock fitting 14 at the inlet end and a second Luer Lock fitting 16 at the outlet end. The resin 18 including the immobilized chelating agent is held in the body 12. A membrane 20 covers the outlet 22 thereby preventing any particles that might be released from the resin 18 from exiting the cartridge 10. A mesh, sieve, frit or membrane 24 covers the inlet 26 and functions to maintain the resin 18 in position in the body 12 of the cartridge 10.

The body 12 and resin 18 contained therein may have a cylindrical shape. The FIGS. 8a and 8d embodiment has a relatively intermediate length and diameter. The FIG. 8b embodiment has a relatively long length and relatively narrow diameter. The FIG. 8c embodiment has a relatively short length and a relatively large diameter.

Each of the embodiments has a different diameter and length which affects the flow characteristic of any fluid passing through the cartridge 10 and the resin 18 holding the immobilized chelating agent. The embodiment chosen for use will depend upon the application.

All of the embodiments 8a-8c provide a straight flow path from the inlet 26 to the outlet 22. While not illustrated, it should be appreciated that the cartridge 10 may be substantially any shape including non-linear, arcuate, even coiled. Further, while the illustrated cartridges 10 are all symmetrical it should be appreciated that nonsymmetrical shapes could be provided. In addition, while all the illustrated cartridges 10 are cylindrical in cross section, substantially any other shape of cross section may be provided including but not limited to frustoconical, helical, square, hexagon and T-shaped.

The cartridge 10 may be used with a continuous flow of solution passing through the cartridge or in a stop-flow mode where solution is introduced into the cartridge, stopped for a time to allow the chelating agent to act, and then expelled from the cartridge.

FIGS. 9a and 9b both show vessels 50 that hold a packet 52 containing resin beads 54 holding the immobilized chelating agent. The packet 52 is made from a semi-permeable membrane similar, for example, to the paper used in the production of tea bags.

In the FIG. 9a embodiment, the vessel 50 is opened and a solution to be treated and a packet 52 containing resin beads 54 are both introduced into the vessel. The vessel 50 is closed and the solution is agitated by magnetic stirrer (not shown) or other means to facilitate interaction and contact between the solution which freely passes through the packet 52 and the chelating agent that is immobilized on the resin beads 54 sealed in the packet.

In the embodiment illustrated in FIG. 9b, the vessel 50 includes an inlet 56 and an outlet 58. The packet 52 is placed in the open vessel 50 and the lid 60 of the vessel 50 is then closed. A pump (not shown) is then actuated to pump solution through the vessel by means of the inlet 56 and outlet 58. Solution flow may be continuous or stop-flow mode in the manner described above. Agitation of solution within the vessel 50 may also be provided. Depending on the application, the vessel 50 may be a sterile vessel.

In an alternative approach, the resin beads 54 holding the chelating agent may be placed directly in the vessel 50 without a packet (see FIG. 9c). Membranes may be provided over the inlet and outlet to insure the resin beads and any particles they might release are maintained in the vessel 50. Lure Lock fittings may also be provided at the inlet and outlet if desired.

FIG. 10 is a plot showing the mean percentage of aluminum removed from a 10% calcium gluconate injection USP as a function of flow rate using the device illustrated in FIG. 8a and the resin and immobilized chelating agent of resin 9. The device had an internal cavity diameter of 6 mm and a length of 20 mm. It held approximately 245 mg of resin and immobilized chelating agent at a loading rate of 0.55 mmoles/gram resin.

As noted above, the chelating agents described in this document are particularly useful in removing aluminum from solutions including calcium gluconate. It should be appreciated, however, that they are also very useful in a multitude of other applications involving the separation of trivalent metal ions from a solution. Such applications include but are not limited to: (1) removal of Al from dialysis fluids and biological products such as albumin and other pharmaceutical solutions in which it is a contaminant, such as phosphates; (2) treatment of metal overload of any trivalent hard or intermediate acid, according to the HSAB theory (for example iron from blood transfusions in beta-thalassemia); (3) as a complexing agent for MRI contrast enhancement (for example with gadolinium); (4) as a treatment for poisoning with tri- and tetravalent metal ions, including radioactive elements that workers may be inadvertently exposed to and are potential chemical warfare agents (dirty bomb components) (for example americium, cerium, and plutonium); (5) extraction of metal ions from solution either to isolate the pure metal or as a pre-concentration step prior to some sort of elemental analysis; (6) environmental remediation by complexing and removing toxic metals from contaminated water and/or soils; and (7) use as a complexing agent for radionuclides of metals such as Ga or In for use as diagnostic imaging agents or as therapeutic radiopharmaceuticals.

The invention has been described herein with reference to certain preferred embodiments. However, as obvious variations will become apparent to those skilled in the art, the invention is not to be considered as limited thereto.

What is claimed:

1. A compound of the formula:

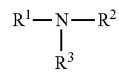

wherein $R^1$=hydrogen, sulfonamide, carbamoyl, carboxamide or benzyl, $R^2$=hydrogen, methyl, ethyl, n-propyl, isopropyl or alkyl
and $R^3$=

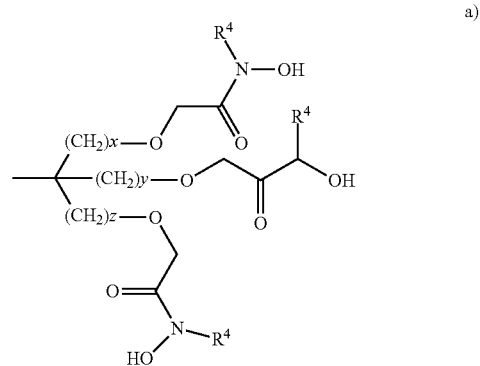

wherein x, y, and z vary independently from 1 to 4, X=$CH_2$ and O, and $R^4$=hydrogen, methyl, ethyl, n-propyl, isopropyl or alkyl;

b)

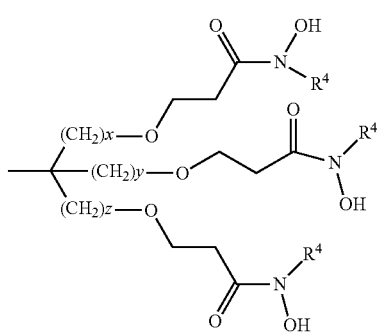

wherein x, y, and z vary independently from 1 to 4, and $R^4$=hydrogen, methyl, ethyl, n-propyl, isopropyl or alkyl;

c)

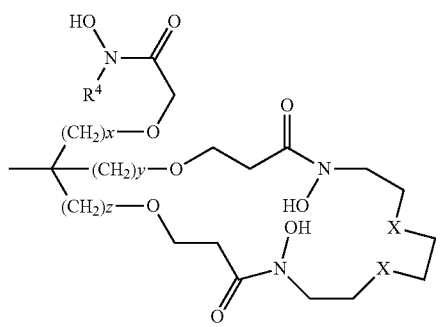

wherein x and y vary independently from 1 to 4, X=$CH_2$ and O, and $R^4$=hydrogen, methyl, ethyl, n-propyl, isopropyl or alkyl;

d)

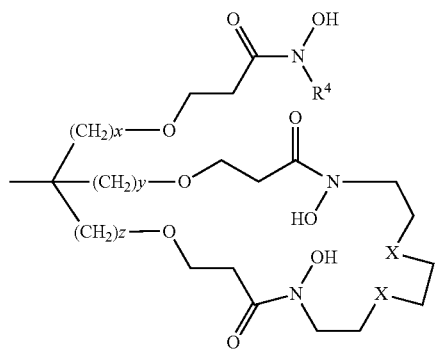

wherein x and y vary independently from 1 to 4, X=$CH_2$ and O, and $R^4$=hydrogen, methyl, ethyl, n-propyl, isopropyl or alkyl;

e)

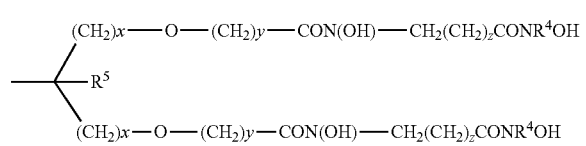

wherein x varies from 1-4, y varies from 1-2, and z varies independently from 2 to 8, $R^4$=hydrogen, methyl, ethyl, n-propyl, isopropyl or similar alkyl substituent, and $R^5$=hydrogen, methyl, ethyl, n-propyl, isopropyl or alkyl; or f)

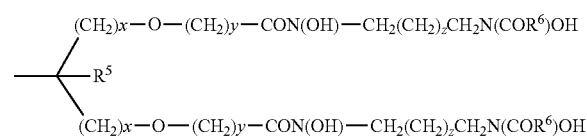

wherein x varies from 1-4, y varies from 1-2, and z varies independently from 2 to 8, $R^5$=hydrogen, methyl, ethyl, n-propyl, isopropyl or similar alkyl substituent, and $R^6$=hydrogen, methyl, ethyl, n-propyl, isopropyl or alkyl, or Ph or aryl.

2. The compound of claim 1 wherein $R^3$=

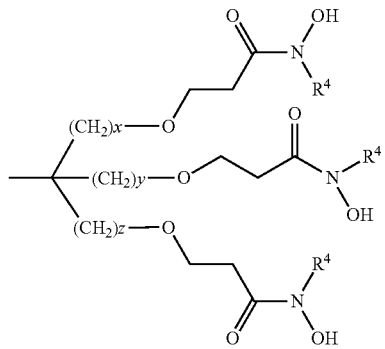

wherein x=1, y=1, z=1 and $R^4$=H.

3. A compound of the formula:

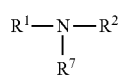

wherein $R^1$=hydrogen, sulfonamide, carbamoyl, carboxamide or benzyl, $R^2$=hydrogen, methyl, ethyl, n-propyl, isopropyl or alkyl and $R^7$= g)

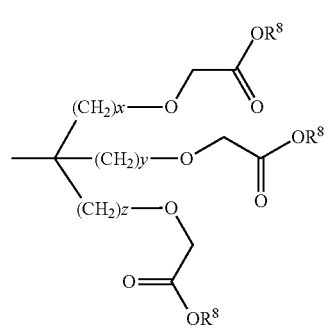

wherein x, y, and z vary independently from 1 to 4, X=$CH_2$ and O, and $R^8$=hydrogen, methyl, ethyl, n-propyl, isopropyl or alkyl and Ph or aryl; or h)

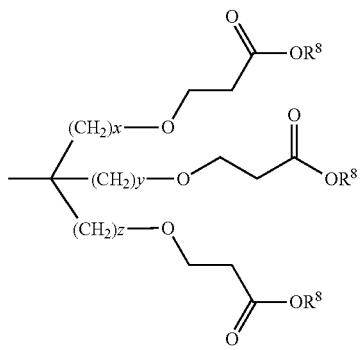

wherein x, y, and z vary independently from 1 to 4, X=CH$_2$ and O, and R$^8$=hydrogen, methyl, ethyl, n-propyl, isopropyl or alkyl and Ph or aryl.

4. A compound of the formula:

$$R^1\text{—}N(R^3)\text{—}R^2$$

where R$^1$=

R$^2$=hydrogen, methyl, ethyl; n-propyl or isopropyl and

R$^3$= a)

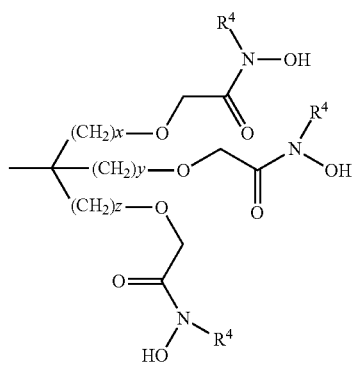

wherein x, y, and z vary independently from 1 to 4, X=CH$_2$ and O, and R$^4$=hydrogen, methyl, ethyl, n-propyl, isopropyl or alkyl;

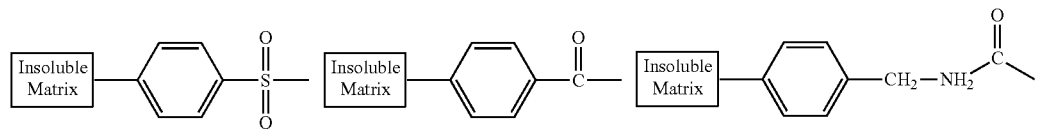

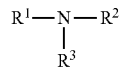

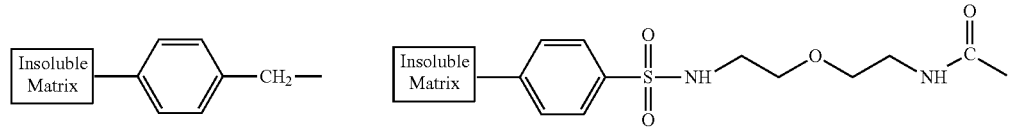

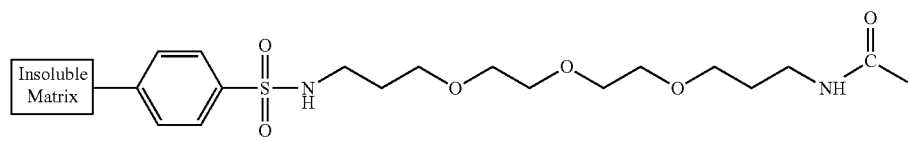

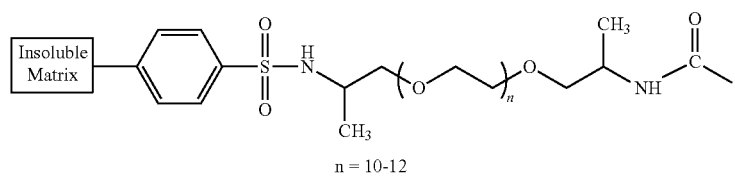

n = 10-12 b)

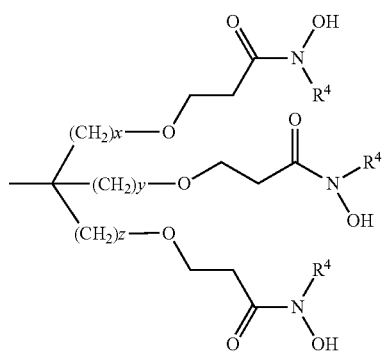

wherein x, y, and z vary independently from 1 to 4, and R⁴=hydrogen, methyl, ethyl, n-propyl, isopropyl or alkyl;

c)

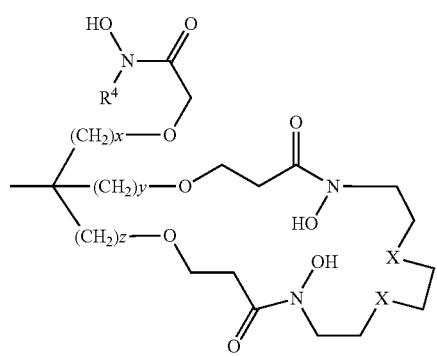

wherein x and y vary independently from 1 to 4, X=CH₂ and O, and R⁴=hydrogen, methyl, ethyl, n-propyl, isopropyl or alkyl;

d)

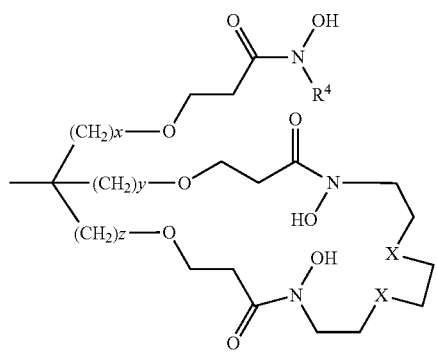

wherein x and y vary independently from 1 to 4, X=CH₂ and O, and R⁴=hydrogen, methyl, ethyl, n-propyl, isopropyl or alkyl;

e)

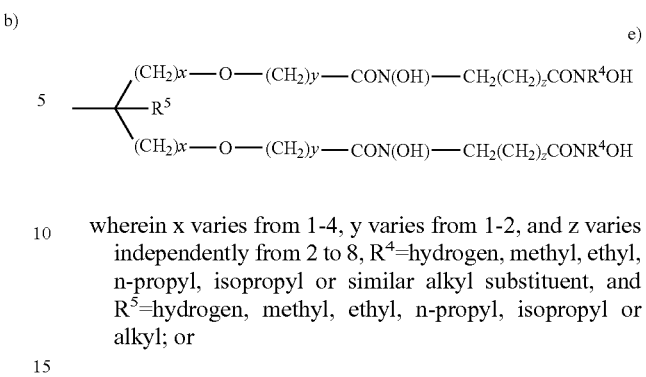

wherein x varies from 1-4, y varies from 1-2, and z varies independently from 2 to 8, R⁴=hydrogen, methyl, ethyl, n-propyl, isopropyl or similar alkyl substituent, and R⁵=hydrogen, methyl, ethyl, n-propyl, isopropyl or alkyl; or f)

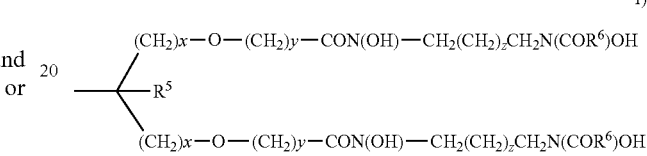

wherein x varies from 1-4, y varies from 1-2, and z varies independently from 2 to 8, R⁵=hydrogen, methyl, ethyl, n-propyl, isopropyl or similar alkyl substituent, and R⁶=hydrogen, methyl, ethyl, n-propyl, isopropyl or alkyl, or Ph or aryl.

5. A compound of the formula:

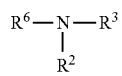

wherein R⁶=

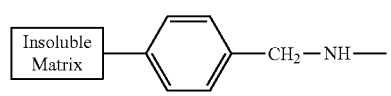

and

R²=hydrogen, methyl, ethyl; n-propyl or isopropyl and R³= a)

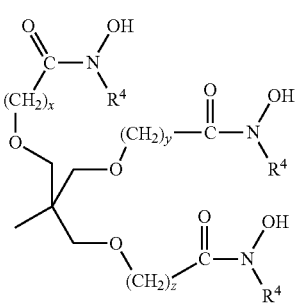

wherein x, y, and z vary independently from 2 to 4 and R⁴=hydrogen or C₁-C₁₀ straight or branched alkyl;

b.)

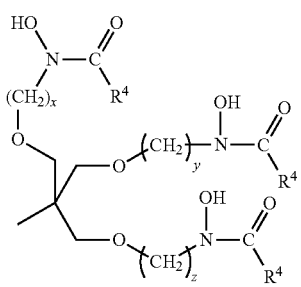

wherein x, y, and z vary independently from 2 to 4, and $R^4$=hydrogen or $C_1$-$C_{10}$ straight or branched alkyl;

c.)

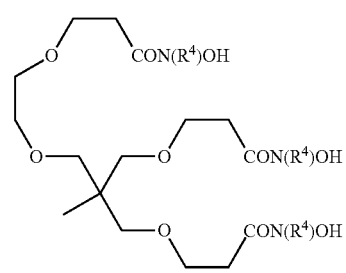

wherein $R^4$=hydrogen or $C_1$-$C_{10}$ straight or branched alkyl;

d.)

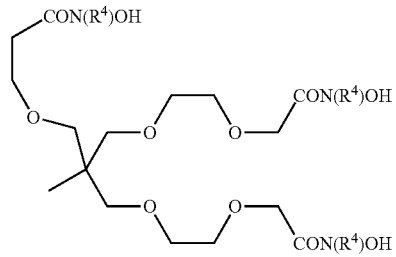

wherein $R^4$=hydrogen or $C_1$-$C_{10}$ straight or branched alkyl;

e.)

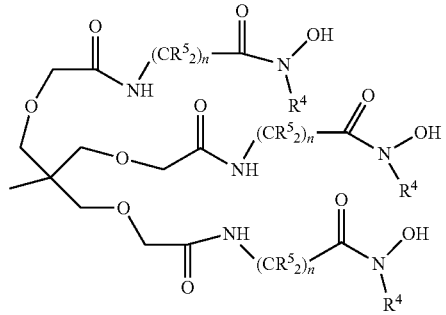

wherein n=2 or 3, $R^5$=hydrogen or methyl, and $R^4$=hydrogen or $C_1$-$C_{10}$ straight or branched alkyl;

f.)

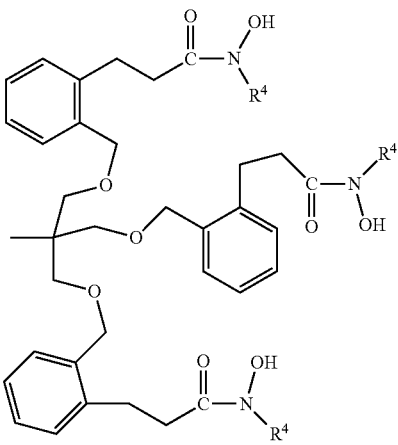

wherein $R^4$=hydrogen or $C_1$-$C_{10}$ straight or branched alkyl;

g)

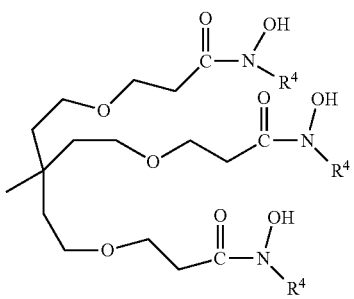

wherein $R^4$=hydrogen or $C_1$-$C_{10}$ straight or branched alkyl; or h)

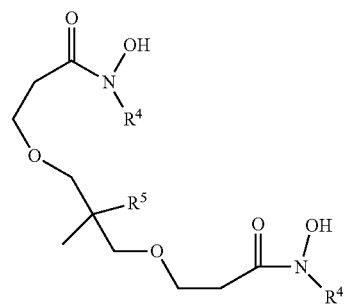

wherein $R^5$=hydrogen or methyl and $R^4$=hydrogen or $C_1$-$C_{10}$ straight or branched alkyl.

* * * * *